US011421276B2

(12) United States Patent
Xu et al.

(10) Patent No.: US 11,421,276 B2
(45) Date of Patent: Aug. 23, 2022

(54) METHODS FOR DIAGNOSING ISCHEMIA

(71) Applicant: The Regents of the University of California, Oakland, CA (US)

(72) Inventors: Huichun Xu, Davis, CA (US); Frank R. Sharp, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/454,755

(22) Filed: Jun. 27, 2019

(65) Prior Publication Data

US 2020/0157624 A1 May 21, 2020

Related U.S. Application Data

(60) Continuation of application No. 15/092,599, filed on Apr. 6, 2016, now abandoned, which is a division of application No. 12/598,107, filed as application No. PCT/US2008/062064 on Apr. 30, 2008, now abandoned.

(60) Provisional application No. 60/915,366, filed on May 1, 2007.

(51) Int. Cl.
*C12Q 1/6883* (2018.01)

(52) U.S. Cl.
CPC ...... *C12Q 1/6883* (2013.01); *C12Q 2600/112* (2013.01); *C12Q 2600/118* (2013.01); *C12Q 2600/136* (2013.01); *C12Q 2600/158* (2013.01)

(58) Field of Classification Search
CPC combination set(s) only.
See application file for complete search history.

(56) References Cited

U.S. PATENT DOCUMENTS

| | | |
|---|---|---|
| 9,057,109 B2 | 6/2015 | Chang |
| 9,200,322 B2 | 12/2015 | Barr et al. |
| 9,410,204 B2 | 8/2016 | Sharp et al. |
| 9,803,243 B2 | 10/2017 | Sharp et al. |
| 10,047,396 B2 | 8/2018 | Sharp et al. |
| 10,196,690 B2 | 2/2019 | Sharp et al. |
| 2001/0053519 A1 | 12/2001 | Fodor et al. |
| 2002/0115120 A1 | 8/2002 | Kapeller-Libermann et al. |
| 2003/0119064 A1 | 6/2003 | Valkirs et al. |
| 2003/0199000 A1 | 10/2003 | Valkirs et al. |
| 2004/0191783 A1 | 9/2004 | Leclercq et al. |
| 2004/0203083 A1 | 10/2004 | Buechler et al. |
| 2006/0046259 A1 | 3/2006 | Baird et al. |
| 2006/0078882 A1 | 4/2006 | Zetter et al. |
| 2007/0042425 A1 | 2/2007 | Hochstrasser et al. |
| 2007/0050146 A1 | 3/2007 | Bentwich et al. |
| 2007/0280917 A1 | 12/2007 | Helgadottir et al. |
| 2009/0148933 A1 | 6/2009 | Battrell et al. |
| 2009/0197774 A1 | 8/2009 | Kozian et al. |
| 2010/0105046 A1 | 4/2010 | Epstein et al. |
| 2010/0197518 A1 | 8/2010 | Xu et al. |
| 2010/0216115 A1 | 8/2010 | Yan et al. |
| 2012/0015904 A1 | 1/2012 | Sharp et al. |
| 2012/0065087 A1 | 3/2012 | Sharp et al. |
| 2012/0316076 A1 | 12/2012 | Sharp et al. |
| 2015/0018234 A1 | 1/2015 | Sharp et al. |
| 2016/0237501 A1 | 8/2016 | Sharp et al. |
| 2016/0265059 A1 | 9/2016 | Sharp et al. |
| 2016/0289765 A1 | 10/2016 | Sharp et al. |
| 2017/0029891 A1 | 2/2017 | Sharp et al. |

FOREIGN PATENT DOCUMENTS

| | | |
|---|---|---|
| WO | 02/12892 | 2/2002 |
| WO | 03/016910 | 2/2003 |
| WO | 2005/116268 | 12/2005 |
| WO | 2006/036220 | 4/2006 |
| WO | 2008/137465 | 11/2008 |
| WO | 2010/012834 | 2/2010 |
| WO | 2012/009547 | 1/2012 |
| WO | 2012/009567 | 1/2012 |
| WO | 2012/121978 | 9/2012 |
| WO | 2013/103781 | 7/2013 |

OTHER PUBLICATIONS

Adams (Stroke (1993) vol. 24, pp. 35-41).*
International Application No. PCT/US2008/062064, International Preliminary Report on Patentability dated Nov. 3, 2009, 6 pages.
International Application No. PCT/US2008/062064, International Search Report and Written Opinion dated Jul. 25, 2008, 6 pages.
International Application No. PCT/US2011/044023, International Preliminary Report on Patentability dated Jan. 24, 2013, 8 pages.
International Application No. PCT/US2011/044023, International Search Report and Written Opinion dated Mar. 28, 2012, 13 pages.
International Application No. PCT/US2011/044062, International Preliminary Report on Patentability dated Jan. 24, 2013, 8 pages.
International Application No. PCT/US2011/044062, International Search Report and Written Opinion dated Mar. 28, 2012, 12 pages.
International Application No. PCT/US2012/027316, International Preliminary Report on Patentability dated Sep. 19, 2013, 7 pages.
International Application No. PCT/US2012/027316, International Search Report and Written Opinion dated Oct. 24, 2012, 11 pages.
International Application No. PCT/US2013/020240, International Preliminary Report on Patentability dated Jul. 17, 2014, 7 pages.
International Application No. PCT/US2013/020240, International Search Report and Written Opinion dated Apr. 12, 2013, 10 pages.
Affymetrix GeneChip Human Genome U133 Array Set HG-U133B, GEO Accession viewer, Mar. 11, 2002, pp. 1-4.
Affymetrix Genechip Human Genome U133 plus 2.0 Array, GEO Accession viewer, Nov. 7, 2003, pp. 1-3.
*Homo sapiens* Disabled Homolog 2, Mitogen-Responsive Phosphoprotein (*Drosophila*), mRNA (cDNA Clone MGC:1764 Image:3504380), Complete cds, Accession: BC003064.2, GI: 33870637, Available online at: https://www.ncbi.nim.nih.gov/nuccore/BC003064.2?report-girevhist, 2017, 1 page.

(Continued)

*Primary Examiner* — Steven Pohnert
(74) *Attorney, Agent, or Firm* — Kilpatrick Townsend & Stockton LLP

(57) ABSTRACT

This invention provides methods and compositions for diagnosing ischemia, ischemia reference expression profiles, and methods for identifying compounds for treating or preventing ischemia.

3 Claims, 8 Drawing Sheets

(56) References Cited

OTHER PUBLICATIONS

Preparation of Human Chromosome Spreads, BETSI Project, Biotechnology Education & Training Sequence Investment, 2008, 6 pages.
U.S. Appl. No. 15/092,599, Final Office Action dated Aug. 9, 2017, 11 pages.
U.S. Appl. No. 15/092,599, Final Office Action dated Jan. 4, 2019, 16 pages.
U.S. Appl. No. 15/092,599, Non-Final Office Action dated May 8, 2018, 17 pages.
U.S. Appl. No. 15/092,599, Non-Final Office Action dated Mar. 1, 2017, 18 pages.
Adams et al., Update to the AHA/ASA Recommendations for the Prevention of Stroke in Patients With Stroke and Transient Ischemic Attack, Stroke, vol. 39, No. 5, May 2008, pp. 1647-1652.
Barr et al., Genomic Biomarkers and Cellular Pathways of Ischemic Stroke by RNA Gene Expression Profiling, Neurology, vol. 75, 2010, pp. 1009-1014.
Benner et al.. Evolution, Language and Analogy in Functional Genomics, Trends in Genetics, vol. 17, No. 7, Jul. 2001, pp. 414-418.
Cheung et al., Natural Variation in Human Gene Expression Assessed in Lymphoblastoid Cells, Nature Genetics, vol. 33, Mar. 2003, pp. 422-425.
Cobb et al., Sepsis Gene Expression Profiling: Murine Splenic Compared with Hepatic Responses Determined by Using Complementary DNA Microarrays, Critical Care Medicine, vol. 30, No. 12, 2002, pp. 2711-2721.
Crawford et al., The Biological Importance of Measuring Individual Variation, The Journal of Experimental Biology, vol. 210, 2007, pp. 1613-1621.
Davi et al., CD40 Ligand and MCP-1 as Predictors of Cardiovascular Events in Diabetic Patients with Stroke, J Atheroscler. Thromb., vol. 16, No. 6, 2009, pp. 707-713.
European Application No. 10014221.5, Extended European Search Report dated Mar. 16, 2011, 7 pages.
European Application No. 11807519.1, Extended European Search Report dated Apr. 11, 2014, 14 pages.
European Application No. 11807532.4, Extended European Search Report dated Nov. 12, 2013, 8 pages.
Ferronato et al., Upregulated Expression of Toll-Like Receptor 4 in Peripheral Blood of Ischaemic Stroke Patients Correlates with Cyclooxygenase 2 Expression, European Journal of Vascular and Endovascular Surgery, vol. 41, No. 3, Mar. 2011, pp. 358-363.
Fung et al., A Biomarker Panel for Peripheral Arterial Disease, Vasc. Med., vol. 13, No. 3, Aug. 2008, pp. 217-224.
Greenbaum et al., Comparing Protein Abundance and mRNA Expression Levels on a Genomic Scale, Genome Biology, vol. 4, No. 117, 2003, pp. 1-8.
Haller et al., Equivalence Test in Quantitative Reverse Transcription Polymerase Chain Reaction: Confirmation of Reference Genes Suitable for Normalization, Anal. Biochem., vol. 335, 2004, pp. 1-9.
Hassan et al., Marker of Endothelial Dysfunction in Lacunar Infarction and Ischaemic Leukoaraiosis, Brain, vol. 126, 2003, pp. 424-432.
Hou et al., High-Density DNA Microarray Analysis of Gene Expression Following Transient Focal Cerebral Ischemia in Mouse, International Congress Series, vol. 1252, 2003, pp. 45-56.
Howell, Experientia, 1975, pp. 260-262.
Indian Application No. 3762/KOLNP/2009, First Examination Report, dated Dec. 12, 2016, 8 pages.
Jakobsen et al., Purification of mRNA Directly from Crude Plant Tissues in 15 Minutes Using Magnetic Oligo dT Microspheres, Nucleic Acids Research, vol. 18, No. 12, 1990, p. 3669.
Jensen et al., Potential Biomarkers for the Diagnosis of Stroke, Expert Review of Cardiovascular Therapy, vol. 7, No. 4, 2009, pp. 389-393.
Jensen et al., The Promise and Potential Pitfalls of Serum Biomarkers for Ischemic Stroke and Transient Ischemic Attack, Neurologist, vol. 14, No. 4, Jul. 2008, pp. 243-246.
Jickling et al., Biomarkers of Ischemic Stroke, US Neurology, vol. 5, No. 2, 2010, pp. 52-54.
Jickling et al., Prediction of Cardioembolic, Arterial and Lacunar Causes of Cryptogenic Stroke by Gene Expression and Infarct Location, Stroke, vol. 43, No. 8, Aug. 2012, pp. 2036-2041.
Jickling et al., Profiles of Lacunar and Non-Lacunar Stroke, Ann Neurol., vol. 70, No. 3, Sep. 2011, pp. 477-485.
Jickling et al., Signatures of Cardioembolic and Large Vessel Ischemic Stroke, Ann Neural., vol. 68, No. 5, Nov. 2010, pp. 681-692.
Karl-Olof Lovblad et al., Actual Diagnostic Approach to the Acute Stroke Patient, Neuro Eur Radial, vol. 16, Jun. 2006, pp. 1253-1269.
Laskowitz et al., Panel of Biomarkers Predicts Stroke, Ann. NY. Acad., Sci., vol. 1053, No. 30, 1 page, 2005.
Leypoldt et al., Dimethylarginine Dimethylaminohydrolase-1 Transgenic Mice are not Protected from Ischemic Stroke, PlosOne, vol. 4, No. 10, Oct. 2009, pp. e73371-e73374.
Li et al., Transcriptome Analysis Reveals Distinct Patterns of Long Noncoding RNAs in Heart and Plasma of Mice With Heart Failure, PLOS ONE, vol. 8, No. 10, Oct. 2013, 10 pages.
Lim et al., MicroRNA in Cerebral Ischemia, Translational Stroke Research, vol. 1, 2010, pp. 287-303.
Lynch et al., Novel Diagnostic Test for Acute Stroke, Stroke, vol. 35, No. 1, Jan. 2004, pp. 57-63.
May, How Many Species are There on Earth, Science, vol. 241, 1988, pp. 1441-1449.
Montaner et al., Etiologic Diagnosis of Ischemic Stroke Subtypes With Plasma Biomarkers, Stroke, vol. 39, No. 8, 2008, pp. 2280-2287.
Moore et al.. Using Peripheral Blood Mononuclear Cells to Determine a Gene Expression Profile of Acute Ischemic Stroke: a Pilot Investigation, Circulation, vol. 111, No. 2, Jan. 18, 2005, pp. 212-221.
Patel et al., Lack of Clinical Significance of Early Ischemic Changes on Computed Tomography in Acute Stroke, Jama, vol. 286, No. 22, Dec. 12, 2001, pp. 2830-2838.
Pradervand et al., Affymetrix Whole-Transcript Human Gene 1.0 ST Array is Highly Concordant With Standard 3'expression Arrays, BioTechniques, vol. 44, No. 6, May 2008, pp. 759-762.
Read et al., Stroke Genomics: Approaches to Identify, Validate, and Understand Ischemic Stroke Gene Expression, J Cereb. Blood Flow Metab., vol. 21, 2001, pp. 755-778.
Reynolds et al., Early Biomarkers of Stroke, Clinical Chemistry, vol. 49, 2003, pp. 1733-1739.
Rothwell et al., Effect of Urgent Treatment of Transient Ischaemic Attack and Minor Stroke on Early Recurrent Stroke (Express Study): A Prospective Population Based Sequential Comparison, Lancet, vol. 370, 2007, pp. 1432-1442.
Schbeck, Cardioembolic Stroke, Medscape, Available online at: https://emedicine.medscape.com/article/1160370-overview, 2015, 19 pages.
Sendera et al., Expression Profiling with Oligonucleotide Arrays: Technologies and Applications for Neurobiology, Neurochemical Research, vol. 27, No. 10, 2002, pp. 1005-1026.
Sharp et al., Genomic Profiles of Stroke in Blood, Stroke, vol. 28, 2007, pp. 691-693.
Shendure et al., Next-Generation DNA Sequencing, Nature Biotechnology, vol. 26, No. 10, Oct. 2008, pp. 1135-1145.
Slogoff et al., Does Perioperative Myocardial Ischemia Lead to Postoperative Myocardial Infarction?, Anesthesiology, vol. 62, 1985, pp. 107-114.
Stamova et al., Gene Expression Profiling of Blood for the Prediction of Ischemic Stroke, Supplementary Material, Stroke, vol. 41, No. 10, 2010, pp. 2171-2177.
Stamova et al., Identification and Validation of Suitable Endogenous Reference Genes for Gene Expression Studies in Human Peripheral Blood, BMC Medical Genomics, vol. 2, No. 49, 2009, pp. 1-13.
Stapleton et al., Prospective Comparison of Whole-Blood- and Plasma-Based Hepatitis C Virus RNA Detection Systems: Improved

(56) References Cited

OTHER PUBLICATIONS

Detection Using Whole Blood as the Source of Viral RNA, Journal of Clinical Microbiology, vol. 37, No. 3, Mar. 1999, pp. 484-489.
Swarup et al., Circulating (Cell-Free) Nucleic Acids—a Promising, Non-Invasive Tool for Early Detection of Several Human Diseases, FEBS Letters, vol. 581, Feb. 2, 2007, pp. 795-799.
Tang et al., Blood Gene Expression Profiling of Neurologic Diseases: A Pilot Microarray Study, Arch Neural., vol. 62, 2005, pp. 210-215.
Tang et al., Gene Expression in Blood Changes Rapidly in Neutrophils and Monocytes After Ischemic Stroke in Humans: a Microarray Study, Journal of Cerebral Blood Flow and Metabolism, vol. 26, No. 8, 2006, pp. 1089-1102.
Thellin et al., Housekeeping Genes as Internal Standards: Use and Limits, J. Biotechnol., vol. 75, 1999, pp. 291-295.
Tombul et al., Hemostatic Markers and Platelet Aggregation Factors as Predictive Markers for Type of Stroke and Neurological Disability Following Cerebral Infarction, Journal of Clinical Neuroscience, vol. 12, No. 4, 2005, pp. 429-434.
Veltkamp et al., Transient Focal Ischemia Increases Endothelial Nitric Oxide Synthase in Cerebral Blood Vessels, Stroke, vol. 33, No. 11, 2002, pp. 2704-2710.
Viswanathan et al., Cerebral Microhemorrhage, Stroke, Journal of the American Heart Association, vol. 37, 2006, pp. 550-555.
Whiteley et al., Blood Biomarkers in the Diagnosis of Ischemic Stroke: A Systematic Review, Stroke, vol. 39, No. 10, 2008, pp. 2902-2909.
Whiteley et al., Blood Markers for the Prognosis of Ischemic Stroke: A Systematic Review, Stroke, vol. 40, No. 5, May 2009, pp. e380-e389.
Xu et al., Gene Expression in Peripheral Blood Differs After Cardioembolic Compared With Large-Vessel Atherosclerotic Stroke: Biomarkers for the Etiology of Ischemic Stroke, J Cereb Blood Flow Metab, vol. 28, No. 7, Jul. 2008, pp. 1320-1328.
Zhan et al., Brief Focal Cerebral Ischemia That Simulates Transient Ischemic Attacks in Humans Regulates Gene Expression in Rat Peripheral Blood, Journal of Cerebral Blood Flow Metabolism, vol. 30, No. 1, 2010, pp. 110-118.
Zhan et al., Transient Ischemic Attacks Characterized by RNA Profiles in Blood, Neurology, vol. 77, No. 19, 2011, pp. 1718-1724.
Zhao et al., Differentially Expressed Genes in Asbestos-Induced Tumorigenic Human Bronchial Epithelial Cells: Implication for Mechanism, Carcinogenesis, vol. 21, Issue 11, Nov. 2000, pp. 2005-2010.
Ziegler et al., TLR2 has a Detrimental Role in Mouse Transient Focal Cerebral Ischemia, Biochemical and Biophysical Research Communication, vol. 359, 2007, pp. 574-579.

\* cited by examiner

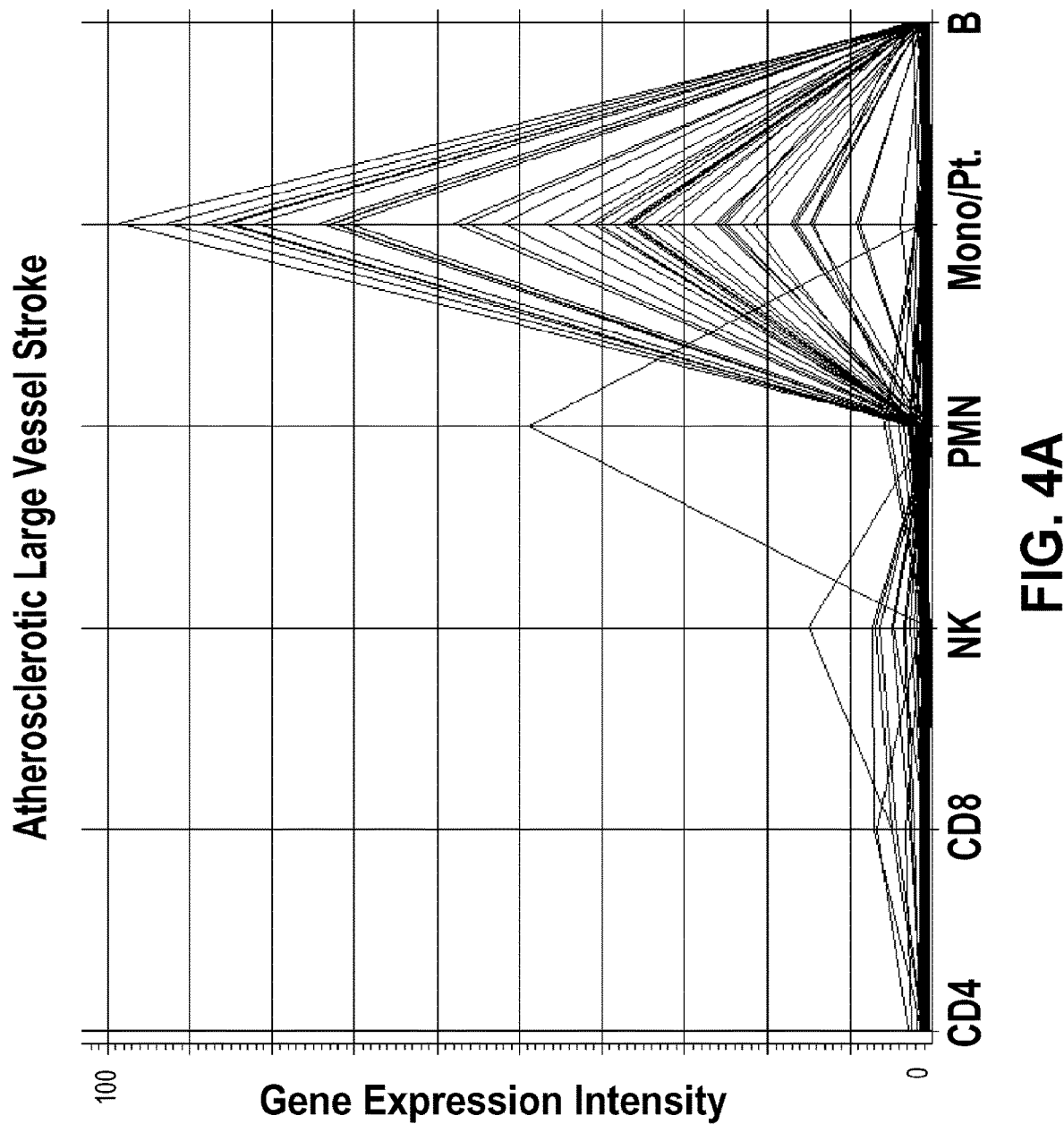

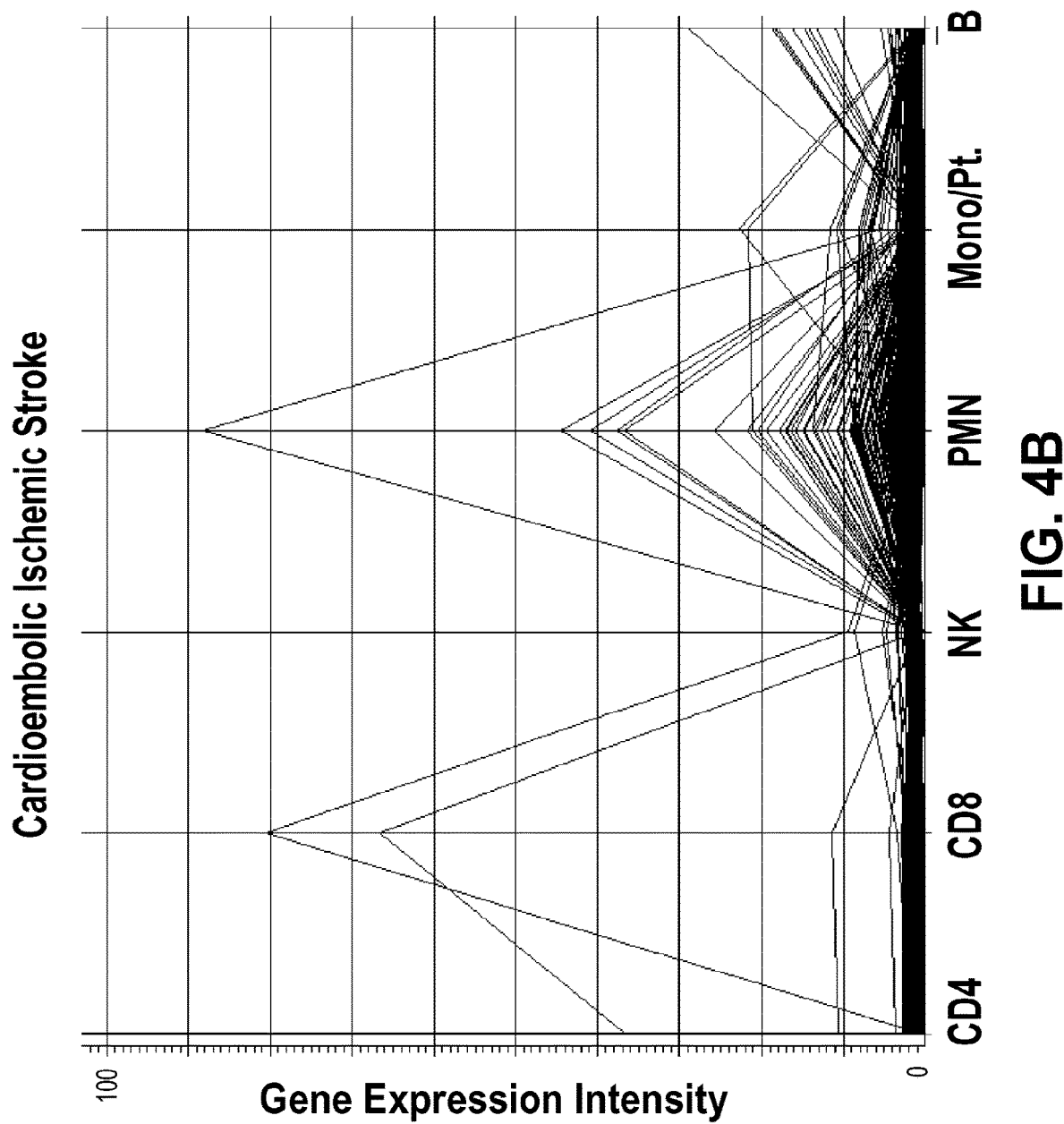

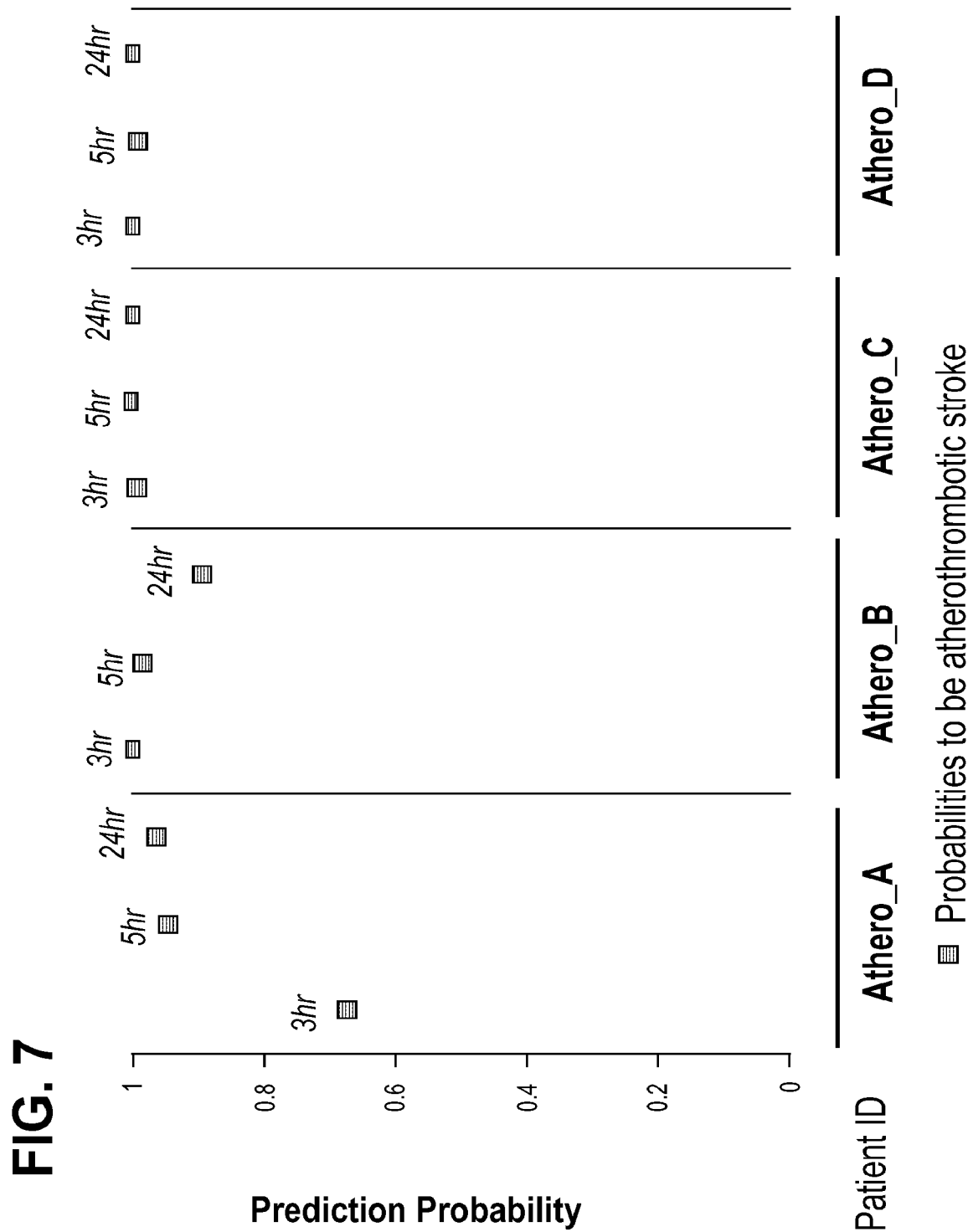

METHODS FOR DIAGNOSING ISCHEMIA

CROSS-REFERENCES TO RELATED APPLICATIONS

This application is a continuation of U.S. application Ser. No. 15/092,599, filed on Apr. 6, 2016, which is a divisional of U.S. application Ser. No. 12/598,107, filed on Mar. 25, 2010, which is the U.S. national stage entry under 35 U.S.C. § 371 of Intl. Appl. No. PCT/US2008/062064, filed on Apr. 30, 2008, which claims the benefit of U.S. Provisional Application No. 60/915,366, filed on May 1, 2007, which are hereby incorporated herein by reference in their entireties for all purposes.

STATEMENT AS TO RIGHTS TO INVENTIONS MADE UNDER FEDERALLY SPONSORED RESEARCH AND DEVELOPMENT

This invention was made with Government support under Grant Nos. NS028167, NS042774, NS043252, NS044283 and NS056302, awarded by the National Institutes of Health. The Government has certain rights in the invention.

BACKGROUND OF THE INVENTION

Ischemic events such as stroke are the third leading cause of death in America. Different subtypes of stroke have their own specific management strategy and a precise diagnosis is critical for the timely treatment of various stroke patients. Currently the gold standard for the diagnosis of acute ischemic stroke versus hemorrhagic stroke relies on imaging technology. However, so far there is no such gold standard for determining the etiology of ischemic stroke. Currently the etiology of ischemic stroke largely depends on the clinician's judgment from indirect clinical information. The main etiologies of acute ischemic stroke include atherothrombotic stroke and cardioembolic stroke. Atheroembolic stroke dictates surgery or aspirin and platelet inhibitor(s); and cardioembolic strokes require treatment with anticoagulant medications such as, e.g., coumadin.

To determine the cause of stroke, patients have magnetic resonance imaging or carotid dopplers to determine if they have atherosclerosis in the carotid and cardiac echocardiograms to determine if they have clot in the heart. The cardiac echocardiogram is very specific, but very insensitive. Even with the best of information, determining the actual cause of stroke is impossible: that is, there is no current direct test for cause. Moreover, somewhere between 30% and 50% of all subjects with transient ischemic attacks and stroke have an unknown cause of stroke.

Thus, there is a need in the art for methods for accurately diagnosing ischemic events (including e.g., stroke and transient ischemic attacks). The present invention meets these and other needs.

BRIEF SUMMARY OF THE INVENTION

The present invention provides methods for diagnosing ischemia (e.g., embolic and thrombotic stroke and transient ischemic attacks) by detecting expression levels of genes differentially expressed in ischemia.

One embodiment of the invention provides methods for diagnosing an ischemia or a predisposition for developing an ischemia. The methods comprise: determining a level of expression of a plurality of ischemia-associated genes in a biological sample from a mammalian subject, wherein a difference (i.e. increase or decrease) of said level compared to a normal control level of the genes indicates that said subject suffers from or is at risk of developing ischemia, wherein said plurality of ischemia-associated genes is selected from the genes set forth in Table 1, 2, 3, 4, 5, 6, or 7. For example, in some embodiments, the level of expression of a plurality, i.e., two or more genes, selected from Table 1 is determined, i.e., two or more of LEPROT, PCGF3, PPP3R1, PVRL2, INSR, BIRC1 (also called, NAIP///LOC728519), TSHZ3, DF (also called, CFD), FBN2, IER3, NUMB, LAK (also called, ALPK1), CD8B1, RRAS2, C21orf7, DAB2, JAM3, ITGA2B, PPBP, SYNJ2, SLC25A37, ZNF185 and C7orf41. In some embodiments, the expression level of 5 or more, 10 or more, 15 or more, 20 or more, or 23 of the genes listed in Table 1 is determined.

In some embodiments, the difference (i.e., increase or decrease) is at least about 1.3 fold, 1.4 fold, or 1.5 fold higher or lower, respectively, than a normal control level.

In some embodiments, the expression level of 2, 3, 4, 5, 6, 7, 8, 9, 10, 11, 12, 13 or 14 genes selected from LEPROT, PCGF3, PPP3R1, PVRL2, INSR, BIRC1, TSHZ3, DF, FBN2, IER3, NUMB, LAK, CD8B1 and RRAS2, identified in Tables 1, 9 and 10, is determined. In some embodiments, at least about a 1.3 fold increase in expression of the following genes: LEPROT, PCGF3, PPP3R1, PVRL2, INSR, BIRC1, TSHZ3, DF, FBN2, IER3, NUMB, and LAK when compared to the normal control level, and at least about a 1.3 fold decrease in expression of the following genes: CD8B1 and RRAS2 when compared to the normal control level indicates that the subject has experienced or is at risk for a cardioembolic stroke.

In some embodiments, the expression level of 2, 3, 4, 5, 6, 7, 8, 9 or 10 genes selected from C21orf7, DAB2, JAM3, ITGA2B, PPBP, SYNJ2, SLC25A37, ZNF185, C7orf41 and LAK, identified in Tables 1, 8 and 10, is determined. In some embodiments, at least about a 1.3 fold decrease in expression of the following genes: C21orf7, DAB2, JAM3, ITGA2B, PPBP, SYNJ2, SLC25A37, ZNF185, C7orf41 and LAK when compared to the normal control level indicates that the subject has experienced or is at risk for an atherothrombotic stroke or atheroembolic stroke. In some embodiments, the ischemia is selected from embolic stroke, thrombotic stroke, and transient ischemic attack. In some embodiments, the sample is blood. In some embodiments, the level of expression is determined by detecting hybridization of an ischemia-associated gene probe to a gene transcript of said biological sample. In some embodiments, the hybridization step is carried out on a nucleic acid array.

Another embodiment of the invention provides an ischemia reference expression profile, comprising a pattern of gene expression of a plurality of the genes set forth in Table 1, 2, 3, 4, 5, 6, or 7. In some embodiments, the ischemia reference expression profile, comprises a pattern of gene expression of a plurality of the genes set forth in Table 1. In some embodiments, at least about a 1.3 fold increase in expression of the following genes: LEPROT, PCGF3, PPP3R1, PVRL2, INSR, BIRC1, TSHZ3, DF, FBN2, IER3, NUMB, and LAK when compared to the normal control level, and at least about a 1.3 fold decrease in expression of the following genes: CD8B1 and RRAS2 when compared to the normal control level is a reference expression profile for cardioembolic stroke. In some embodiments, at least about a 1.3 fold decrease in expression of the following genes: C21orf7, DAB2, JAM3, ITGA2B, PPBP, SYNJ2, SLC25A37, ZNF185, C7orf41, and LAK when compared to the normal control level is a reference expression profile for atherothrombotic stroke or atheroembolic stroke.

Yet another embodiment of the invention provides methods of screening for a compound for treating or preventing ischemia. The methods comprise: a) contacting a candidate compound with a cell expressing one or more genes set forth in Table 1, 2, 3, 4, 5, 6, or 7; and b) selecting a compound that modulates the expression level of one or more genes set forth in Table 1, 2, 3, 4, 5, 6, or 7. In some embodiments a compound that decreases the expression of at least one gene selected from the group consisting of: LEPROT, PCGF3, PPP3R1, PVRL2, INSR, BIRC1, TSHZ3, DF, FBN2, IER3, NUMB, and LAK when compared to the normal control level, or increases the expression of at least one gene selected from the group consisting of: CD8B1 and RRAS2 relative to a control level is identified as a compound useful for treating or preventing ischemia, including, e.g., cardioembolic stroke. In some embodiments, a compound that increases the expression of at least one gene selected from the group consisting of: C21orf7, DAB2, JAM3, ITGA2B, PPBP, SYNJ2, SLC25A37, ZNF185, C7orf41, and LAK is identified as a compound useful for treating or preventing ischemia, including, e.g., atherothrombotic stroke or atheroembolic stroke.

A further embodiment of the invention provides an array comprising a plurality of polynucleotides which specifically bind (i.e., specifically hybridize) to a plurality of nucleic acid sequences set forth in Table 1, 2, 3, 4, 5, 6 or 7. In some embodiments, the invention provides an array comprising a plurality of polynucleotides which specifically bind (i.e., specifically hybridize) to a plurality of nucleic acid sequences set forth in Table 1.

Another embodiment of the invention provides a reaction mixture comprising a plurality of polynucleotides which specifically hybridize (e.g., primers) to a plurality of nucleic acid sequences set forth in Table 1, 2, 3, 4, 5, 6 or 7. In some embodiments, the invention provides a reaction mixture comprising a plurality of polynucleotides which specifically hybridize (e.g., primers) to a plurality of nucleic acid sequences set forth in Table 1. In some embodiments, the reaction mixture is a PCR mixture, for example, a multiplex PCR mixture.

These and other embodiments of the invention are further described by the detailed description that follows.

BRIEF DESCRIPTION OF THE TABLES

Table 1 sets forth a list of 23 genes differentially expressed in ischemia (e.g., cardioembolic stroke, arthero-thrombotic stroke, and transient ischemic attacks).

Table 2 sets forth a list of 77 genes differentially expressed in ischemia (e.g., cardioembolic stroke, arthero-thrombotic stroke, and transient ischemic attacks).

Table 3 sets forth a list of 95 genes differentially expressed in ischemia (e.g., cardioembolic stroke, arthero-thrombotic stroke, and transient ischemic attacks).

Table 4 sets forth a list of 133 genes differentially expressed in ischemia (e.g., cardioembolic stroke, arthero-thrombotic stroke, and transient ischemic attacks).

Table 5 sets forth a list of 259 genes differentially expressed in ischemia (e.g., cardioembolic stroke, arthero-thrombotic stroke, and transient ischemic attacks).

Table 6 sets forth a list of 466 genes differentially expressed in ischemia (e.g., cardioembolic stroke, arthero-thrombotic stroke, and transient ischemic attacks).

Table 7 sets forth a list of 706 genes differentially expressed in ischemia (e.g., cardioembolic stroke, arthero-thrombotic stroke, and transient ischemic attacks).

Table 8 sets forth relative expression levels of selected genes described in Example 1 as differentially expressed in atherothrombotic stroke relative to normal control subjects.

Table 9 sets forth relative expression levels of selected genes described in Example 1 as differentially expressed in cardioembolic stroke subjects relative to normal control subjects.

Table 10 sets forth the relative expression levels of genes listed in Table 1 in cardioembolic stroke subjects relative to normal control subjects; atheroembolic stroke subjects relative to normal control, and cardioembolic stroke subjects relative to atheroembolic stroke subjects.

BRIEF DESCRIPTION OF THE DRAWINGS

FIG. 4a illustrates expression activities of atherosclerotic stroke-specific genes across subtypes of healthy blood cells.

FIG. 4b illustrates expression activities of cardioembolic stroke-specific genes across subtypes of healthy blood cells.

FIG. 7 illustrates a 10-fold cross validation result for known atherosclerotic stroke samples with 23 genes in PAM.

DETAILED DESCRIPTION OF THE INVENTION

I. Introduction

Figure 1:
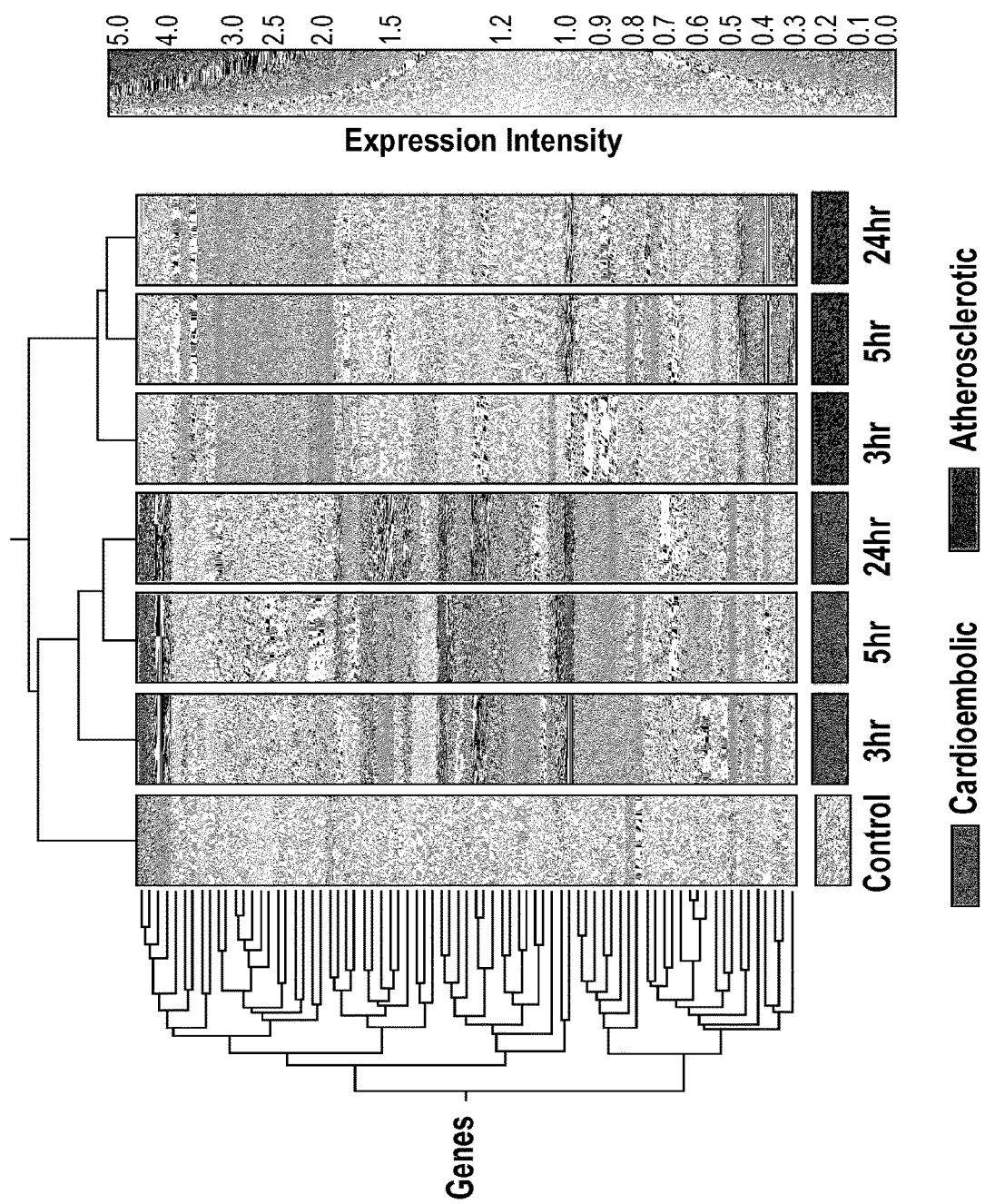
FIG. 1 illustrates an expression heatmap of genes differentially regulated between cardioembolic and atherosclerotic stroke patients with at least a 1.5 fold change.

The present invention provides methods for the diagnosis of ischemia (e.g., stroke and transient ischemic attacks ("TIA")).

The invention is based on identification of differential gene expression patterns in subjects with an ischemia (e.g., stroke and TIA). Detection of the expression patterns of a plurality of the genes set forth in Table 1, 2, 3, 4, 5, 6, or 7 leads to a definitive diagnosis of the type of ischemia that a subject has developed or is at risk for developing. Therefore, this invention provides the first direct method for determining the causes of ischemia (stroke and TIA).

The gene expression patterns described herein can conveniently be used to diagnose, monitor and prognose ischemia (e.g., stroke and TIA). For example, the gene expression patterns can be detected to definitively classify the type of ischemic event that a subject has developed or has a predisposition for developing. In some embodiments, the gene expression patterns can also be used as ischemic reference profiles. In other embodiments, the gene expression patterns can be used to identify compounds for treating or preventing ischemia.

II. Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 3rd ed. (2001) Cold Spring Harbor Laboratory Press, Cold Spring Harbor, N.Y. and Ausubel, et al., CURRENT PROTOCOLS IN MOLECULAR BIOLOGY, 1990-2008, Wiley Interscience), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

"Ischemia" or "ischemic event" as used herein refers to diseases and disorders characterized by inadequate blood supply (i.e., circulation) to a local area due to blockage of the blood vessels to the area. Ischemia includes for example, strokes and transient ischemic attacks. Strokes include, e.g., ischemic stroke (including, but not limited to, cardioembolic strokes, atheroembolic or atherothrombotic strokes, i.e., strokes caused by atherosclerosis in the carotid, aorta, heart, and brain, small vessel strokes (i.e., lacunar strokes), strokes caused by diseases of the vessel wall, i.e., vasculitis, strokes caused by infection, strokes caused by hematological disorders, strokes caused by migraines, and strokes caused by medications such as hormone therapy), hemorrhagic ischemic stroke, intracerebral hemorrhage, and subarachnoid hemorrhage.

"Ischemia reference expression profile" refers to the pattern of expression of a set of genes (e.g., a plurality of the genes set forth in Tables 1, 2, 3, 4, 5, 6 or 7) differentially expressed (i.e., overexpressed or underexpressed) in ischemia relative to a normal control. A gene from Tables 1, 2, 3, 4, 5, 6 or 7 that is expressed at a level that is at least about 1.3, 1.4, 1.5, 1.6, 1.7, 1.8, 1.9, 2, 3, 4, 5, 6, 7, 8, 9 or 10 fold higher than the level in a normal control is a gene overexpressed in ischemia and a gene from Tables 1, 2, 3, 4, 5, 6 or 7 that is expressed at a level that is at least about 1.3, 1.4, 1.5, 1.6, 1.7, 1.8, 1.9, 2, 3, 4, 5, 6, 7, 8, 9 or 10 fold lower than the level in a normal control is a gene underexpressed in ischemia. Alternately, genes that are expressed at a level that is at least about 10%, 20%, 30%, 40%, 50%, 60%, 70%, 80%, 90%, or 100% higher than the level in a normal control is a gene overexpressed in ischemia and a gene that is expressed at a level that is at least about 10%, 20%, 30%, 40%, 50%, 60%, 70%, 80%, 90%, or 100% lower than the level in a normal control is a gene underexpressed in ischemia.

A "plurality" refers to two or more, for example, 2, 3, 4, 5, 6, 7, 8, 9, 10, 11, 12, 13, 14, 15, 16, 17, 18, 19, 20, 21, 22, 23 or more (e.g., genes). In some embodiments, a plurality refers to 50, 96, 100, 150, 192, 200, 250, 384 or 500 genes. In some embodiments, "plurality" refers to all genes listed in one or more tables, e.g., all genes listed in Table 1, Table 2, Table 3, Table 4, Table 5, Table 6 and/or Table 7.

"Sample" or "biological sample" includes sections of tissues such as biopsy and autopsy samples, and frozen sections taken for histologic purposes. Such samples include blood, sputum, tissue, lysed cells, brain biopsy, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

"Array" as used herein refers to a solid support comprising attached nucleic acid or peptide probes. Arrays typically comprise a plurality of different nucleic acid or peptide probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., Science, 251:767-777 (1991). These arrays may generally be produced using mechanical synthesis methods or light directed synthesis methods which incorporate a combination of photolithographic methods and solid phase synthesis methods. Techniques for the synthesis of these arrays using mechanical synthesis methods are described in, e.g., U.S. Pat. No. 5,384,261. Arrays may comprise a planar surface or may be nucleic acids or peptides on beads, gels, polymeric surfaces, fibers such as fiber optics, glass or any other appropriate substrate as described in, e.g., U.S. Pat. Nos. 5,770,358, 5,789,162, 5,708,153, 6,040,193 and 5,800,992. Arrays may be packaged in such a manner as to allow for diagnostics or other manipulation of an all inclusive device, as described in, e.g., U.S. Pat. Nos. 5,856,174 and 5,922,591.

The term "gene" means the segment of DNA involved in producing a polypeptide chain; it includes regions preceding and following the coding region (leader and trailer) as well as intervening sequences (introns) between individual coding segments (exons).

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The phrase "stringent hybridization conditions" refers to conditions under which a probe will hybridize to its target subsequence, typically in a complex mixture of nucleic acid, but to no other sequences. Stringent hybridization conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent hybridization conditions are selected to be about 5-10° C. lower than the thermal melting point for the specific sequence at a defined ionic strength Ph. The $T_m$ is the temperature (under defined ionic strength, Ph, and nucleic concentration) at which 50% of the probes complementary to the target hybridize to the target sequence at equilibrium (as the target sequences are present in excess, at $T_m$, 50% of the probes are occupied at equilibrium). Stringent hybridization conditions will be those in which the salt concentration is less than about 1.0 M sodium ion, typically about 0.01 to 1.0 M sodium ion concentration (or other salts) at Ph 7.0 to 8.3 and the temperature is at least about 30° C. for short probes (e.g., 10 to 50 nucleotides) and at least about 60° C. for long probes (e.g., greater than 50 nucleotides). Stringent hybridization conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent hybridization conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. "Amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine I, Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region of an ischemia-associated gene (e.g., a gene set forth in Table 1, 2, 3, 4, 5, 6, or 7), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to ischemia-associated nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

By "host cell" is meant a cell that contains an expression vector and supports the replication or expression of the expression vector. Host cells may be, for example, prokaryotic cells such as E. coli or eukaryotic cells such as yeast cells or mammalian cells such as CHO cells.

"Inhibitors," "activators," and "modulators" of expression or of activity are used to refer to inhibitory, activating, or modulating molecules, respectively, identified using in vitro and in vivo assays for expression or activity, e.g., ligands, agonists, antagonists, and their homologs and mimetics. The term "modulator" includes inhibitors and activators. Inhibitors are agents that, e.g., inhibit expression of a polypeptide or polynucleotide of the invention or bind to, partially or totally block stimulation or enzymatic activity, decrease, prevent, delay activation, inactivate, desensitize, or down regulate the activity of a polypeptide or polynucleotide of the invention, e.g., antagonists. Activators are agents that, e.g., induce or activate the expression of a polypeptide or polynucleotide of the invention or bind to, stimulate, increase, open, activate, facilitate, enhance activation or enzymatic activity, sensitize or up regulate the activity of a polypeptide or polynucleotide of the invention, e.g., agonists. Modulators include naturally occurring and synthetic ligands, antagonists, agonists, small chemical molecules and the like. Assays to identify inhibitors and activators include, e.g., applying putative modulator compounds to cells, in the presence or absence of a polypeptide or polynucleotide of the invention and then determining the functional effects on a polypeptide or polynucleotide of the invention activity. Samples or assays comprising a polypeptide or polynucleotide of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a polypeptide or polynucleotide of the invention relative to the control is about 80%, optionally 50% or 25-1%. Activation is achieved when the activity value of a polypeptide or polynucleotide of the invention relative to the control is 110%, optionally 150%, optionally 200-500%, or 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, RNAi, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons.

III. Diagnosis of Ischemia

The invention provides methods for diagnosing ischemia (e.g., stroke or transient ischemic attacks) or a predisposition for developing ischemia by detecting the expression of a plurality of ischemia-associated genes in a sample (e.g., a blood sample) from a subject. In some embodiments of the invention, expression of a plurality of the genes set forth in Table 1, 2, 3, 4, 5, 6, or 7 is detected. In one preferred embodiment, expression of a plurality of the genes set forth in Table 1 is detected. In one embodiment, at least about a 1.3 fold increase in expression of the following genes: LEPROT, PCGF3, PPP3R1, PVRL2, INSR, BIRC1, TSHZ3, DF, FBN2, IER3, NUMB, and LAK when compared to the normal control level, and at least about a 1.3 fold decrease in expression of the following genes: CD8B1 and RRAS2 when compared to the normal control level indicates that the subject has experienced or is at risk for a cardioembolic stroke. In another embodiment, at least about a 1.3 fold decrease in expression of the following genes: C21orf7, DAB2, JAM3, ITGA2B, PPBP, SYNJ2, SLC25A37, ZNF185, C7orf41, and LAK when compared to the normal control level indicates that the subject has experienced or is at risk for an atherothrombotic stroke or atheroembolic stroke.

Gene expression may be measured using any method known in the art. One of skill in the art will appreciate that the means of measuring gene expression is not a critical aspect of the invention. A variety of methods of specific DNA and RNA measurement using nucleic acid hybridization techniques are known to those of skill in the art (see, Sambrook, supra and Ausubel, supra) and may be used to detect the expression of the genes set forth in Table 1, 2, 3, 4, 5, 6, or 7. Some methods involve an electrophoretic separation (e.g., Southern blot for detecting DNA, and Northern blot for detecting RNA), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting a polypeptide of the invention.

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins *Nucleic Acid Hybridization, A Practical Approach*, IRL Press (1985); Gall and Pardue, *Proc. Natl. Acad. Sci. U.S.A.*, 63:378-383 (1969); and John et al. Nature, 223:582-587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, "*Practice and Theory of Enzyme Immunoassays,*" *Laboratory Techniques in Biochemistry and Molecular Biology*, Burdon and van Knippenberg Eds., Elsevier (1985), pp. 9-20).

The probes are typically labeled either directly, as with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like.

Other labels include, e.g., ligands that bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden *Introduction to Immunocytochemistry*, 2nd ed., Springer Verlag, N Y (1997); and in Haugland *Handbook of Fluorescent Probes and Research Chemicals*, a combined handbook and catalogue Published by Molecular Probes, Inc. (1996).

In general, a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

Most typically, the amount of RNA is measured by quantifying the amount of label fixed to the solid support by binding of the detection reagent. Typically, the presence of a modulator during incubation will increase or decrease the amount of label fixed to the solid support relative to a control incubation which does not comprise the modulator, or as compared to a baseline established for a particular reaction type. Means of detecting and quantifying labels are well known to those of skill in the art.

In preferred embodiments, the target nucleic acid or the probe is immobilized on a solid support. Solid supports suitable for use in the assays of the invention are known to those of skill in the art. As used herein, a solid support is a matrix of material in a substantially fixed arrangement.

For example, in one embodiment of the invention, microarrays are used to detect the pattern of gene expression. Microarrays provide one method for the simultaneous measurement of the expression levels of large numbers of genes. Each array consists of a reproducible pattern of a plurality of nucleic acids (e.g., a plurality of nucleic acids that hybridize to a plurality of the genes set forth in Table 1, 2, 3, 4, 5, 6, or 7) attached to a solid support. In one embodiment, the array contains a plurality of nucleic acids that hybridize to a plurality of the genes listed in Table 1. Labeled RNA or DNA is hybridized to complementary probes on the array and then detected by laser scanning. Hybridization intensities for each probe on the array are determined and converted to a quantitative read-out of relative gene expression levels in ischemia (e.g., stroke or transient ischemic attacks).

In some embodiments, a sample is obtained from a subject, total mRNA is isolated from the sample and is converted to labeled cRNA and then hybridized to an array. Relative transcript levels are calculated by reference to appropriate controls present on the array and in the sample. See Mahadevappa and Warrington, *Nat. Biotechnol.* 17, 1134-1136 (1999).

A variety of automated solid-phase assay techniques are also appropriate. For instance, very large scale immobilized polymer arrays (VLSIPS™), available from Affymetrix, Inc. (Santa Clara, Calif.) can be used to detect changes in expression levels of a plurality of genes involved in the same regulatory pathways simultaneously. See, Tijssen, supra., Fodor et al. (1991) *Science,* 251: 767-777; Sheldon et al. (1993) *Clinical Chemistry* 39(4): 718-719, and Kozal et al. (1996) *Nature Medicine* 2(7): 753-759.

Detection can be accomplished, for example, by using a labeled detection moiety that binds specifically to duplex nucleic acids (e.g., an antibody that is specific for RNA-DNA duplexes). One preferred example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) *Analytical Biochemistry* 181: 153-162; Bogulayski (1986) et al. *J. Immunol. Methods* 89:123-130; Prooijen-Knegt (1982) *Exp. Cell Res.* 141:397-407; Rudkin (1976) *Nature* 265:472-473, Stollar (1970) *Proc. Nat'l Acad. Sci. USA* 65:993-1000; Ballard (1982) *Mol. Immunol.* 19:793-799; Pisetsky and Caster (1982) *Mol. Immunol.* 19:645-650; Viscidi et al. (1988) *J. Clin. Microbial.* 41:199-209; and Kiney et al. (1989) *J. Clin. Microbiol.* 27:6-12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (3rd ed.) *Fundamental Immunology* Raven Press, Ltd., NY (1993); Coligan, et al., *Current Protocols in Immunology*, Wiley Interscience (1991-2008); Harlow and Lane, *Antibodies: A Laboratory Manual* Cold Spring Harbor Press, N Y (1988); Harlow and Lane, *Using Antibodies*, Cold Spring Harbor Press, N Y (1999); Stites et al. (eds.) *Basic and Clinical Immunology* (4th ed.) Lange Medical Publications, Los Altos, Calif., and references cited therein; Goding *Monoclonal Antibodies: Principles and Practice* (2d ed.) Academic Press, New York, N.Y., (1986); and Kohler and Milstein *Nature* 256: 495-497 (1975)). Other suitable techniques for antibody preparation include selection of libraries of recombinant antibodies in phage or similar vectors (see, Huse et al. *Science* 246:1275-1281 (1989); and Ward et al. *Nature* 341:544-546 (1989)). Specific monoclonal and polyclonal antibodies and antisera will usually bind with a $K_D$ of at least about 0.1 µM, preferably at least about 0.01 µM or better, and most typically and preferably, 0.001 µM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems include the polymerase chain reaction (PCR) system, in particular RT-PCR or real time PCR, and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation.

An alternative means for determining the level of expression of the nucleic acids of the present invention is in situ hybridization. In situ hybridization assays are well known and are generally described in Angerer et al., *Methods Enzymol.* 152:649-660 (1987). In an in situ hybridization assay, cells, preferentially human cells from the cerebellum or the hippocampus, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

In one embodiment of the invention, microarrays are used to detect the pattern of gene expression. Microarrays provide one method for the simultaneous measurement of the expression levels of large numbers of genes. Each array consists of a reproducible pattern of a plurality of nucleic acids (e.g., a plurality of nucleic acids that hybridize to a plurality of the genes set forth in Table 1, 2, 3, 4, 5, 6 or 7) attached to a solid support. In one embodiment, the array contains a plurality of nucleic acids that hybridize to a plurality of the genes listed in Table 1. Labeled RNA or DNA is hybridized to complementary probes on the array and then detected by laser scanning. Hybridization intensities for each probe on the array are determined and converted to a quantitative read-out of relative gene expression levels in ischemia (e.g., stroke or transient ischemic attacks) In some embodiments, a sample is obtained from a subject, total mRNA is isolated from the sample and is converted to labeled cRNA and then hybridized to an array. Relative transcript levels are calculated by reference to appropriate controls present on the array and in the sample. See Mahadevappa and Warrington, *Nat. Biotechnol.* 17, 1134-1136 (1999).

In other embodiments, quantitative RT-PCR is used to detect the expression of a plurality of the genes set forth in Tables 1, 2, 3, 4, 5, 6 or 7. In one embodiment, quantitative RT-PCR is used to detect a plurality of the genes listed in Table 1. A general overview of the applicable technology can be found, for example, in *A-Z of Quantitative PCR*, Bustin, ed., 2004, International University Line; *Quantitative PCR Protocols*, Kochanowski and Reischl, eds., 1999, Humana Press; *Clinical Applications of PCR*, Lo, ed., 2006, Humana Press; *PCR Protocols: A Guide to Methods and Applications* (Innis et al. eds. (1990)) and *PCR Technology: Principles and Applications for DNA Amplification* (Erlich, ed. (1992)). In addition, amplification technology is described in U.S. Pat. Nos. 4,683,195 and 4,683,202. Methods for multiplex PCR, known in the art, are applicable to the present invention.

Accordingly, in one embodiment of the invention provides a reaction mixture comprising a plurality of polynucleotides which specifically hybridize (e.g., primers) to a plurality of nucleic acid sequences of the genes set forth in Table 1, 2, 3, 4, 5, 6 or 7. In some embodiments, the invention provides a reaction mixture comprising a plurality of polynucleotides which specifically hybridize (e.g., primers) to a plurality of nucleic acid sequences of the genes set forth in Table 1. In some embodiments, the reaction mixture is a PCR mixture, for example, a multiplex PCR mixture.

This invention relies on routine techniques in the field of recombinant genetics. Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-2008, Wiley Interscience)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, Tetrahedron Letts. 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

IV. Ischemia Reference Profiles

The invention also provides ischemia reference profiles. The reference profiles comprise information correlating the expression levels of a plurality of ischemia-associated genes (i.e., a plurality of the genes set forth in Table 1, 2, 3, 4, 5, 6, or 7) to particular types of ischemia. In one embodiment, the ischemia reference profile correlates the expression levels of a plurality of the genes listed in Table 1 to particular types of ischemia. The profiles can conveniently be used to diagnose, monitor and prognose ischemia.

One embodiment of the invention provides an ischemia reference profile for subjects who have experienced or are at risk for experiencing cardioembolic stroke. Accordingly, the ischemia reference profile correlates the expression levels of a plurality of the genes selected from LEPROT, PCGF3, PPP3R1, PVRL2, INSR, BIRC1, TSHZ3, DF, FBN2, IER3, NUMB, LAK, CD8B1 and RRAS2. For example, an expression profile exhibiting at least about a 1.3 fold increase in expression of the following genes: LEPROT, PCGF3, PPP3R1, PVRL2, INSR, BIRC1, TSHZ3, DF, FBN2, IER3, NUMB, and LAK when compared to the normal control level, and at least about a 1.3 fold decrease in expression of the following genes: CD8B1 and RRAS2 when compared to the normal control level is a reference profile for a subject who has experienced or is at risk for a cardioembolic stroke.

One embodiment of the invention provides an ischemia reference profile for subjects who have experienced or are at risk for experiencing atherothrombotic stroke. Accordingly, the ischemia reference profile correlates the expression levels of a plurality of the genes selected from C21orf7, DAB2, JAM3, ITGA2B, PPBP, SYNJ2, SLC25A37, ZNF185, C7orf41, and LAK. An expression profile exhibiting at least about a 1.3 fold decrease in expression of the following genes: C21orf7, DAB2, JAM3, ITGA2B, PPBP, SYNJ2, SLC25A37, ZNF185, C7orf41, and LAK when compared to the normal control level is a reference profile for a subject who has experienced or is at risk for an atherothrombotic stroke.

The reference profiles can be entered into a database, e.g., a relational database comprising data fitted into predefined categories. Each table, or relation, contains one or more data categories in columns. Each row contains a unique instance of data for the categories defined by the columns. For example, a typical database for the invention would include a table that describes a sample with columns for age, gender, reproductive status, expression profile and so forth. Another table would describe a disease: symptoms, level, sample identification, expression profile and so forth. In one embodiment, the invention matches the experimental sample to a database of reference samples. The database is assembled with a plurality of different samples to be used as reference samples. An individual reference sample in one embodiment will be obtained from a patient during a visit to a medical professional. Information about the physiological, disease and/or pharmacological status of the sample will also be obtained through any method available. This may include, but is not limited to, expression profile analysis, clinical analysis, medical history and/or patient interview. For example, the patient could be interviewed to determine age, sex, ethnic origin, symptoms or past diagnosis of disease, and the identity of any therapies the patient is currently undergoing. A plurality of these reference samples will be taken. A single individual may contribute a single reference sample or more than one sample over time. One skilled in the art will recognize that confidence levels in predictions based on comparison to a database increase as the number of reference samples in the database increases.

The database is organized into groups of reference samples. Each reference sample contains information about physiological, pharmacological and/or disease status. In one aspect the database is a relational database with data organized in three data tables, one where the samples are grouped primarily by physiological status, one where the samples are grouped primarily by disease status and one where the samples are grouped primarily by pharmacological status. Within each table the samples can be further grouped according to the two remaining categories. For example the physiological status table could be further categorized according to disease and pharmacological status.

As will be appreciated by one of skill in the art, the present invention may be embodied as a method, data processing system or program products. Accordingly, the present invention may take the form of data analysis systems, methods, analysis software, etc. Software written according to the present invention is to be stored in some form of computer readable medium, such as memory, hard-drive, DVD ROM or CD ROM, or transmitted over a network, and executed by a processor. The present invention also provides a computer system for analyzing physiological states, levels of disease states and/or therapeutic efficacy. The computer system comprises a processor, and memory coupled to said processor which encodes one or more programs. The programs encoded in memory cause the processor to perform the steps of the above methods wherein the expression profiles and information about physiological, pharmacological and disease states are received by the computer system as input. Computer systems may be used to execute the software of an embodiment of the invention (see, e.g., U.S. Pat. No. 5,733,729).

V. Methods of Identifying Compounds for Treating or Preventing Ischemia

The invention also provides methods of identifying compounds for treating or preventing ischemia. Compounds for treating or preventing ischemia can be readily identified according to methods well known to those of skill in the art.

A number of different screening protocols can be utilized to identify agents that modulate the level of activity or expression of ischemia-associated genes (i.e., agents that decrease the activity or expression of genes overexpressed in ischemia and increase the activity or expression of genes underexpressed in ischemia).

Preliminary screens can be conducted by screening for agents that modulate expression of ischemia-associated genes. The screening methods of the invention can be performed as in vitro or cell-based assays. Cell based assays can be performed in any cells which express one or more ischemia-associated genes. One of skill in the art will appreciate that ischemia-associated genes can be expressed in cells that do not contain endogenous ischemia-associated genes. Cell-based assays may involve whole cells or cell fractions to screen for agent binding or modulation of ischemia-associated genes Suitable cell-based assays are described in, e.g., DePaola et al., *Annals of Biomedical Engineering* 29: 1-9 (2001).

In vivo assays can also be used to identify agents that can be used to treat or prevent ischemia. The basic format of such methods involves administering a lead compound identified during an initial screen to an animal that serves as a model for ischemia and then determining if in fact the ischemia is ameliorated. The animal models utilized in validation studies generally are mammals of any kind. Specific examples of suitable animals include, but are not limited to, primates (e.g., chimpanzees, monkeys, and the like) and rodents (e.g., mice, rats, guinea pigs, rabbits, and the like).

The agents tested as potential modulators of ischemia-associated gene expression can be any small chemical compound, or a biological entity, such as a polypeptide, sugar, nucleic acid or lipid. Essentially any chemical compound can be used as a potential modulator in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays).

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like).

Devices for the preparation of combinatorial libraries are commercially available (see, e.g., ECIS™, Applied Bio-Physics Inc., Troy, N.Y., MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

VI. Kits

The invention also provides kits for diagnosing ischemia or a predisposition for developing ischemia. For example, the invention provides kits that include one or more reaction vessels that have aliquots of some or all of the reaction components of the invention in them. Aliquots can be in liquid or dried form. Reaction vessels can include sample processing cartridges or other vessels that allow for the containment, processing and/or amplification of samples in the same vessel. The kits may comprise a plurality of nucleic acid probes that hybridize to a plurality the genes set forth in Table 1, 2, 3, 4, 5, 6, or 7. In one embodiment, the kits comprise a plurality of nucleic acid probes that hybridize to a plurality of the genes set forth in Table 1. The probes may be immobilized on an array as described herein. In addition, the kit can comprise appropriate buffers, salts and other reagents to facilitate amplification and/or detection reactions (e.g., primers) for determining the expression levels of a plurality of the genes set forth in Table 1, 2, 3, 4, 5, 6, or 7. In one embodiment, the kit comprises appropriate buffers, salts and other reagents to facilitate amplification and/or detection reactions (e.g., primers) for determining the expression levels of a plurality of the genes set forth in Table 1. The kits can also include written instructions for the use of the kit.

EXAMPLES

The following examples are offered to illustrate, but not to limit the claimed invention.
Materials and Methods
Human Subjects:

Acute ischemic stroke patients (n=45 samples from 15 patients) were enrolled in the CLEAR trial. The Institutional Review Boards at the participating institutions approved the study protocols and consent forms. Stroke patients were diagnosed clinically and computed tomography brain scans performed to exclude hemorrhage. Following informed consent, patients were randomized to receive either standard-dose r-tPA (Activase) or a combination of eptifibatide and low-dose r-tPA (Activase) in a 1:3 ratio in a double-blinded manner within 3 hr of the onset of stroke. Blood (15 ml) was drawn from each patient into PAXgene tubes before the treatment ("<3 hr samples"), approximately 2 hours after the thrombolysis treatment ("5 hr samples") and 24 hours after the stroke onset ("24 hr samples"), respectively. A total of 45 blood samples were collected from the subjects with stroke. For additional information see ClinicalTrials.gov under identifier NCT00250991.

The etiology of the strokes was assessed using the TOAST criteria (Adams et al. Stroke (1993) 24:35-41) and classified as: Atherosclerotic stroke, Cardioembolic stroke and Stroke with undetermined etiology. Patients with small artery lacunar stroke were generally excluded from the CLEAR trial because of the study design, and none of the patients reported here had lacunar stroke.

Control peripheral blood samples were drawn from 8 healthy volunteers (n=16 samples). Each volunteer contributed two independent blood samples one day apart. Healthy controls had no history of cardiovascular or cerebral vascular disease, recent infection or hematological disease.

Sample Processing

Whole blood (15 ml) was collected into 6 PAXgene vacutainers (PreAnalytiX, Hilden, Germany) via antecubital fossa venipuncture from each subject. PAXgene tubes were frozen at −80° C. after 2 hr at room temperature. Total RNA was isolated (PAXgene blood RNA kit, PreAnalytiX, Germany) according to the manufacturer's protocol. The RNA is from PMNs (Neutrophils, basophils and eosinophils), mononuclear cells (PBMC-lymphocytes, macrophage/monocytes), platelets and red blood cell precursors.

Microarray Hybridization and RT-PCR

RNA samples were labeled, hybridized and scanned according to standard Affymetrix Protocols (Affymetrix Expression Analysis Technical Manual). 10 μg total RNA was labeled using the One-Cycle Target Labeling protocol. Affymetrix Human U133 Plus 2 arrays that contain more that 54,000 probe sets were used for each RNA sample. The RNA samples are also subject to RT-PCR.

Microarray Data Analysis

Probe-level data was saved in Affymetrix.cel files and summarized with Robust Multi-array Average (RMA) software (on the worldwide web at bioconductor.org/). Statistical analyses including a one-way analysis of variance (ANOVA) for cardioembolic stroke, atherosclerotic stroke, Stroke of undetermined etiology and controls) were performed using Genespring software (Silicon Genetics, Redwood City, Calif.). The Benjamini-Hochberg false discovery rate (FDR) was used to control for multiple comparisons with a 5% FDR (<0.05) being considered significant. Different fold change filters were applied to minimize type-two error. Direct comparison between cardioembolic stroke and atherosclerotic stroke was also performed (Student's t-test) to compare with the ANOVA analysis. Demographic data were analyzed with the Student T test or Fisher's exact test. The methods have been described in detail in our previous studies. See, e.g., Tang et al., *Brain Res Mol Brain Res* (2004) 132:155-167; Tang et al., *Ann Neurol* (2004) 56:808-814; and Tang et al., *J Cereb Blood Flow Metab* (2006) 26(8):1089-102.

Example 1: Identification of Genes Differentially Expressed in Cardioembolic Strokes and Atherothrombotic Strokes Demographic Data for Cardioembolic and Atherosclerotic Stroke Patients There were no significant age, gender or race differences and no differences in history of hypercholesterolemia or hypertension between the groups. Many of the cardioembolic stroke patients had a history of heart disease while none of the atherosclerotic stroke patients did (p=0.06).

Differential Expression Profiles of Cardioembolic Stroke and Atherosclerotic Stroke The one-way ANOVA (FDR<0.05, Student-Newman-Keuls post hoc test, equal variance) yielded 660 genes that were differentially regulated for cardioembolic vs. atherosclerotic stroke. The Student t-test (p<0.001) yielded 135 genes that were differentially regulated for cardioembolic stroke vs atherosclerotic stroke. Of these 135 genes identified using the t-test, 95 of these were also identified using the one-way ANOVA. Using a 1.5 fold change filter, a total of 77 genes were significantly regulated between cardioembolic stroke and atherosclerotic stroke (significant using ANOVA or T-test; fold change >1.5). A Pearson cluster analysis using these 77 genes showed clear segregation of samples from controls and samples from subjects with cardioembolic stroke compared with subjects with atherosclerotic stroke at each of the times following stroke (FIG. 1). This also held true whether cluster analysis was performed using the 660 genes from the ANOVA analysis or the 135 genes from the t-test.

We next examined possible confounding factors on the identified etiology-related genes. Of the 54 genes identified as race-related (white/black, t-test. FDR<0.05, fold change >1.5), none are among the 77 etiology-related genes. Of the 424 genes identified as being regulated by aspirin in patients on aspirin prior to the stroke, only 5 were among the 77 etiology-related genes (6.5%) (Tang et al., *Med Hypotheses* (2006) 67:462-466).

Etiology Prediction of Undetermined Patients

Prediction Analysis of Microarrays (PAM) was used to determine the minimum number of genes that differentiate cardioembolic from atherosclerotic stroke. PAM employs shrunken nearest centroids to find the most reliable genes that differentiate two or more classes. (Tang et al., 2006, supra; Tibshirani et al., 2002, *Proc Natl Acad Sci USA* 99:6567-6572) PAM identified a minimum of 23 genes that best differentiated cardioembolic from atherosclerotic stroke. A 10 fold cross validation with a leave-one-out approach showed that these 23 genes correctly classified 32 of 33 samples from subjects with known causes of stroke (Table 1).

With regard to healthy controls, the 23 genes can be classified into 3 subgroups, using a 1.3 fold change in expression as a significant change. LEPROT, PCGF3, PPP3R1, PVRL2, INSR, BIRC1, TSHZ3, DF, FBN2, IER3, NUMB, and LAK exhibit at least a 1.3 fold increase in expression in subjects with cardioembolic stroke versus control subjects and RRAS2 and CD8B1 exhibit at least a 1.3 fold decrease in expression in subjects with cardioembolic stroke versus control subjects. C21orf7, DAB2, JAM3, ITGA2B, PPBP, SYNJ2, SLC25A37, ZNF185, C7orf41, and LAK exhibit at least 1.3 fold decrease in expression in subjects with atherothrombotic stroke versus control subjects.

Thus, by examining the expression level of 23 genes, we can achieve 95.2% sensitivity and 100% specificity for the diagnosis of cardioembolic stroke, 100% sensitivity and 95.2% specificity for atherothrombotic stroke, respectively. Thus, only a short list of genes needs to be screened for a single patient and this can be done simultaneously on a single real time PCR panel. The power of this list of genes was shown by predicting the cause of stroke in six additional patients with an unknown cause of stroke. All six of these six patients were diagnosed as having cardioembolic stroke, which would mean that they should be treated with Coumadin rather than other types of therapy to prevent future strokes.

By examining the blood gene expression of as few as 23 genes, we are able to differentiate cardioembolic stroke from atherothrombotic stroke in an objective manner as early as three hours after onset of stroke. As noted, the gene expression profiles disclosed herein can be used to determine the cause of the stroke or TIA in those patients who have an unknown etiology.

Figure 2:
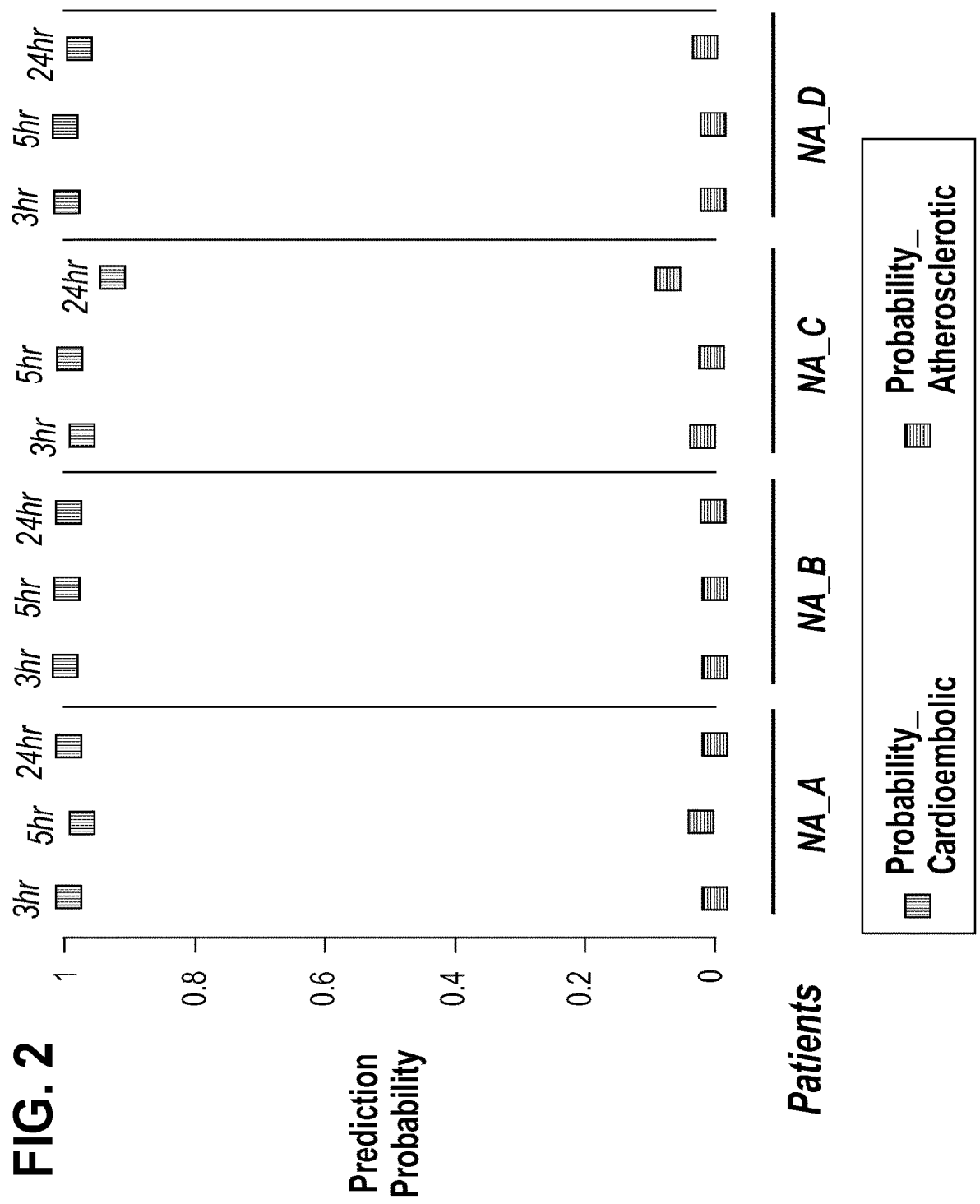
FIG. 2 illustrates etiology prediction of stroke samples with unknown etiology according to the expression pattern of 23 genes using PAM.

PAM and the minimum set of 23 genes were used to predict the etiology of the subjects whose cause of stroke could not be determined based upon clinical TOAST criteria. PAM classified all 12 of the unknown samples as being cardioembolic stroke with probabilities over 90% (92.9-99.9%, FIG. 2).

Function Analysis of Atherosclerotic and Cardioembolism Regulated Genes

Figure 3:
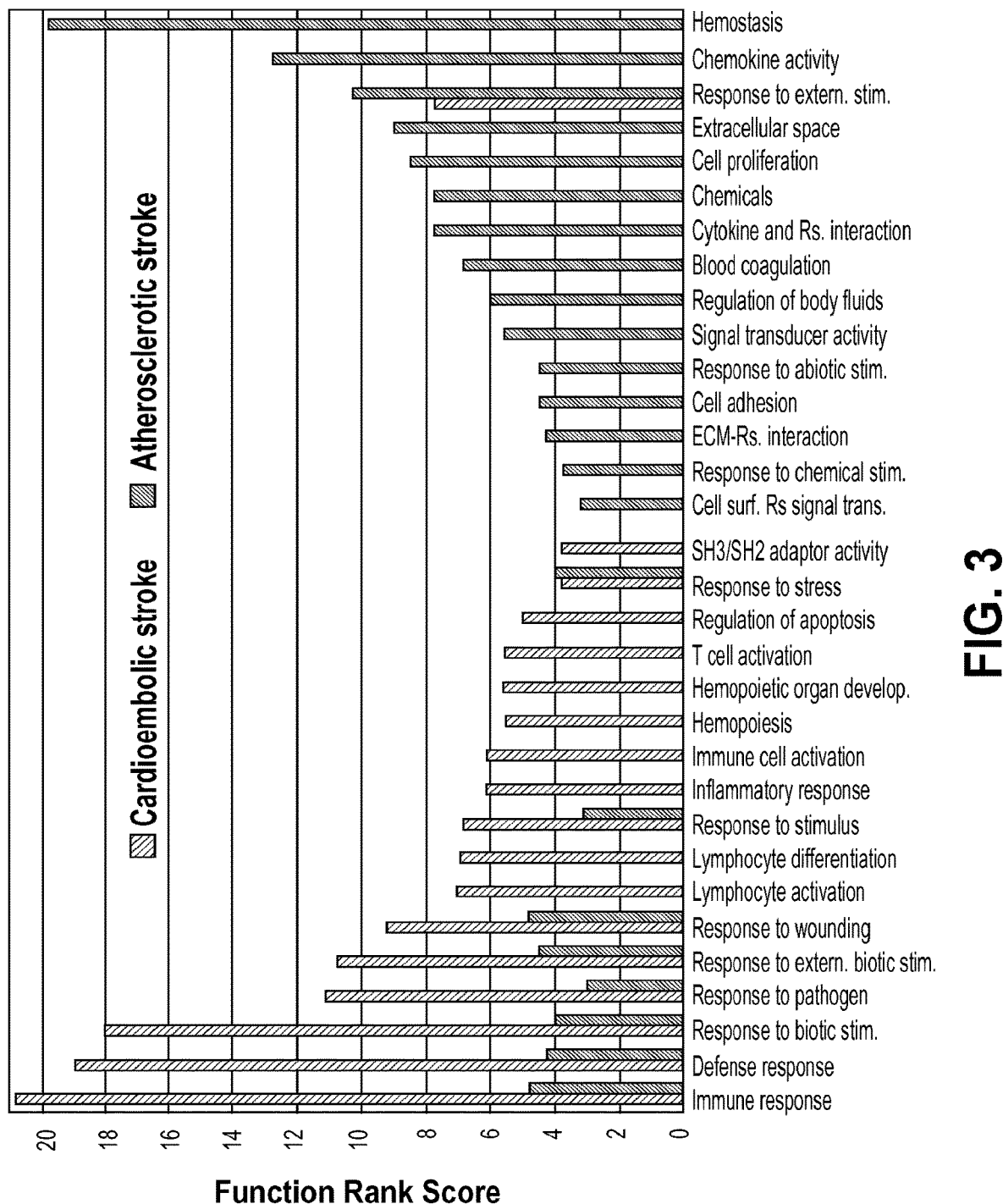
FIG. 3 illustrates a function comparison of cardioembolic stroke-specific genes versus atherosclerotic stroke-specific genes. Obvious duplication of function classes is omitted for clarity purposes.
Figure 5:
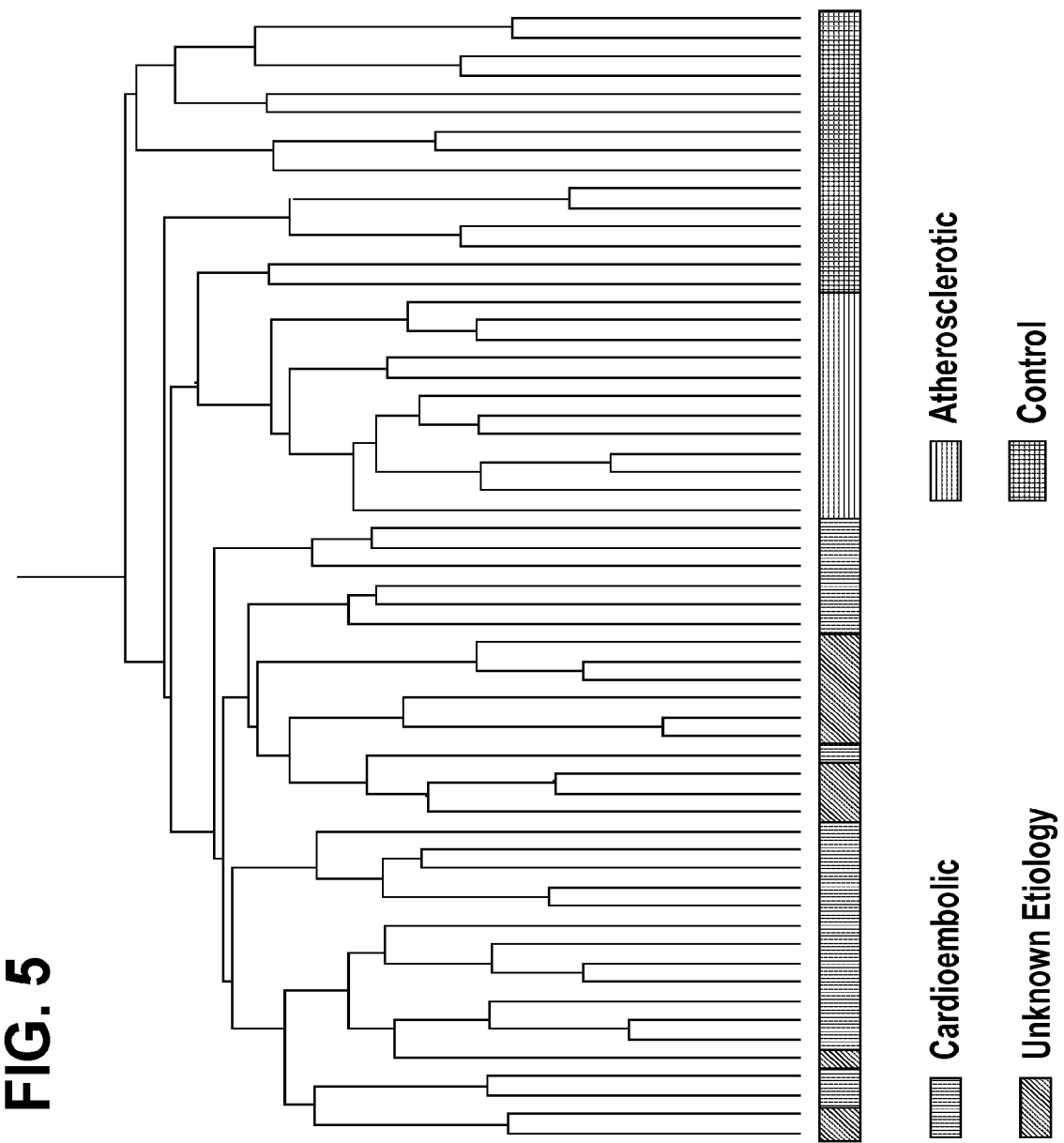
FIG. 5 illustrates etiology prediction of stroke samples from unknown etiologies by cluster analysis.
Figure 6:
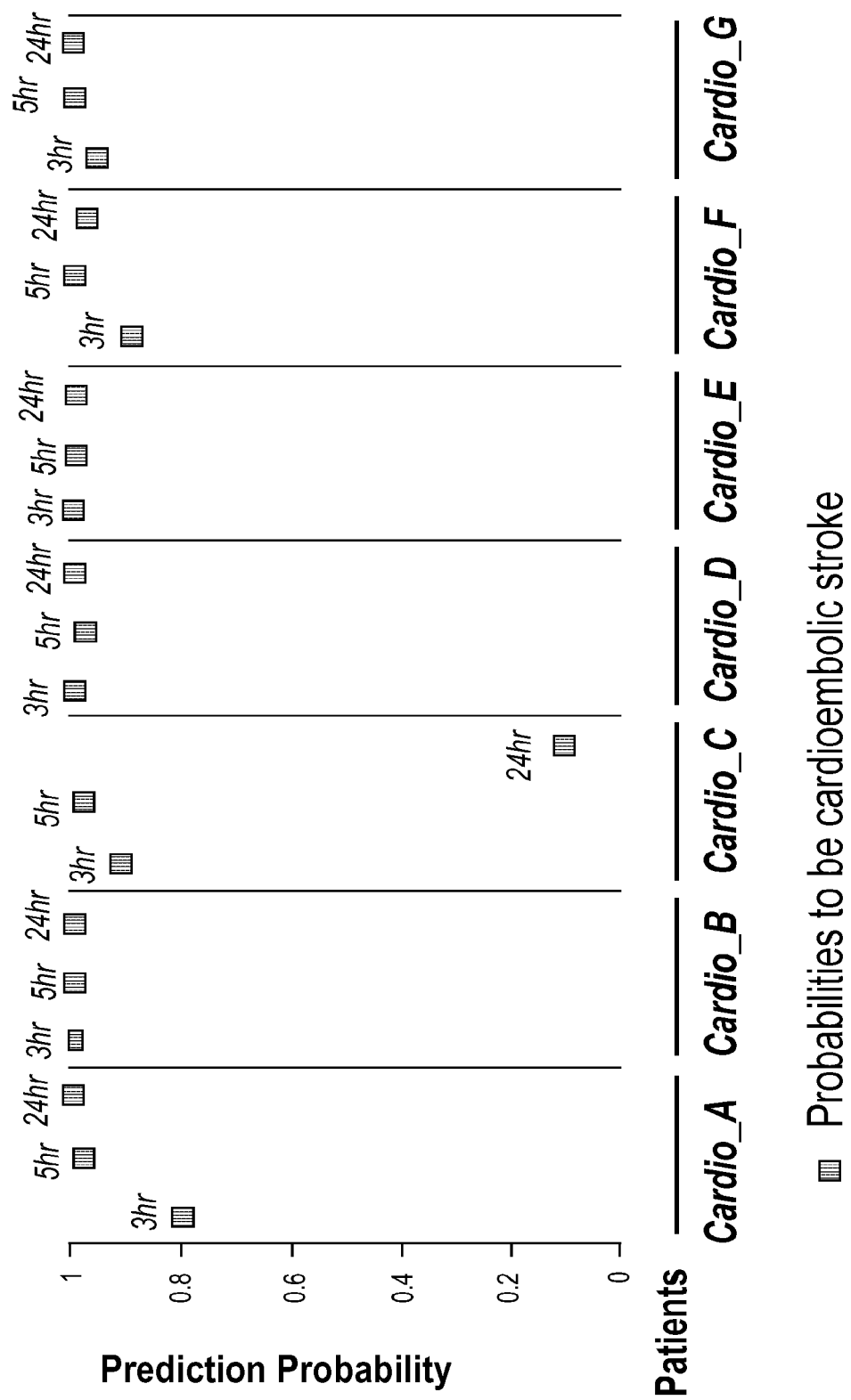
FIG. 6 illustrates a 10-fold cross validation result for known cardioembolic stroke samples with 23 genes in PAM.

The differentially regulated genes between cardioembolic stroke and atherosclerotic stroke were then classified by cluster analysis. Two subgroups of genes were identified: one is mainly regulated in cardioembolic stroke relative to healthy control (281 genes at 1.2 fold filter or 148 genes at 1.3 fold filter), the other is mainly regulated in atherosclerotic stroke relative to healthy control (84 genes at 1.2 fold filter or 63 genes at 1.3 fold filter). The functions of the two etiology-specific gene lists were then explored in the Nextbio System (Cupertino, Calif., USA), a web-based data search and analysis engine. The genes were ranked according to fold change and then queried against GO, KEGG pathways and REACTOME databases in Nextbio with p value 0.05 cut off. This analysis found that the genes regulated by cardioembolic stroke were mainly involved in response to pathogens, including immune cell activation, defense response, proliferation and apoptosis. In contrast, the genes mainly regulated by atherosclerotic stroke were related to hemostasis, cytokines and chemokines (FIG. 3). For many of the functional pathways represented, there is little overlap between the pathways related to atherosclerotic versus cardioembolic stroke.

Comparison of all the high throughput studies deposited in the Nextbio system (currently 6000 studies) to our study showed that atherosclerotic-specific expression profiles shared the most genes with Crohn's disease (28 genes in common)(GEO Series GSE3365), (Burczynski et al., *J Mol Diagn* (2006) 8:51-61) ulcerative colitis (14 genes in common)(GEO Series GSE3365), (Burczynski et al., 2006, supra) and rheumatoid arthritis (26 genes in common)(GEO Series GSE4588). On the other hand, cardioembolism-specific expression profiles were most similar to those from patients with sepsis and septic shock (105 genes and 109 genes in common at day 1, respectively)(GEO Series GSE4607). (Wong et al., *Physiol Genomics* (2007) 30(2): 146-55).

Cell Type Sources of the Stroke Etiology Regulated Genes

The genes regulated in cardioembolic versus atherosclerotic stroke might or might not be expressed in restricted cell types in blood. Using our reference gene list derived from healthy controls, (Du et al., *Genomics* (2006) 87(6):693-703) most of the genes regulated in atherosclerotic stroke appear to be regulated in platelets and monocytes (FIG. 4a) whereas most of the genes regulated in cardioembolic stroke appear to be expressed in neutrophils (FIG. 4b).

Example 2 Diagnosis of Stroke

A blood sample will be obtained. RNA is isolated from the blood sample and the RNA labeled and applied to a microarray or similar platform to examine all expressed genes in blood (including, e.g., the genes set forth in Tables 1, 2, 3, 4, 5, or 6). From the microarray the expression of every gene in blood can then be calculated. Suitable software such as Prediction Analysis of Microarrays (PAM) is then used to calculate the probability that the changes of gene expression in the patient are due to a stroke. A probability of 85% of more that the changes represent a stroke is used to confirm the diagnosis of stroke.

The next step is to then determine the cause of the stroke. This is important because strokes from atherosclerosis may require surgery or vascular stenting; and strokes from cardioembolism require anti-coagulation with suitable mediacations including, e.g., Coumadin, Warfarin, and the like; and strokes from lacunar disease/hypertension require treatment with aspirin and other anti-platelet agents combined with drugs for the hypertension. From the same microarray used to make the diagnosis of a stroke, the expression of the genes listed in Table 1 is assessed in the patient's blood sample. The expression of these genes is compared to a control or reference sample, or to a combination of genes on the array that serve as control genes. As shown in Table 1, the genes that increase in stroke due to atherosclerosis are decreased in stroke due to cardioembolism; and the genes that increase in stroke due to cardioembolism decrease in stroke due to atherosclerosis; and some genes only change either in stroke due to cardioembolism or only change in stroke due to atherosclerosis. The profile of expression of all 23 genes is again entered into PAM, and PAM calculates the probability that the stroke in a given patient is either cardioembolic, atherosclerotic or due to some other cause. If the probability is 85% or greater for a given cause of stroke, then the cause of stroke will be reported. If the probability is 50% for any cause of stroke then the gene expression profile will not have been able to determine the cause of stroke.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications and accession numbers cited herein are hereby incorporated by reference in their entirety for all purposes.

TABLE 1

| GenBank ID | Human UniGene ID | Gene Symbol | Gene description | Fold Difference (Cardioembolic vs. Atherothrombotic) |
|---|---|---|---|---|
| BC003064 | 481980 | DAB2 | disabled homolog 2, mitogen-responsive phosphoprotein (*Drosophila*) | 1.449 |
| NM_001343 | 481980 | DAB2 | disabled homolog 2, mitogen-responsive phosphoprotein (*Drosophila*) | 1.531 |
| NM_003897 | 591785 | IER3 | immediate early response 3 | 1.421 |
| NM_017526 | 23581 | LEPROT | leptin receptor overlapping transcript | 1.464 |
| NM_001999 | 519294 | FBN2 | fibrillin 2 (congenital contractural arachnodactyly) | 1.64 |
| NM_007150 | 16622 | ZNF185 | zinc finger protein 185 (LIM domain) | 1.544 |
| NM_000945 | 280604 | PPP3R1 | protein phosphatase 3 (formerly 2B), regulatory subunit B, 19 kDa, alpha isoform (calcineurin B, type I) | 1.503 |
| NM_004536 | 191356 | BIRC1 (NAIP /// LOC728519) | NLR family, apoptosis inhibitory protein /// similar to Baculoviral IAP repeat-containing protein 1 (Neuronal apoptosis inhibitory protein) | 1.417 |

TABLE 1-continued

| GenBank ID | Human UniGene ID | Gene Symbol | Gene description | Fold Difference (Cardioembolic vs. Atherothrombotic) |
|---|---|---|---|---|
| NM_001928 | 155597 | CFD | complement factor D (adipsin) | 1.542 |
| NM_000419 | 411312 | ITGA2B | integrin, alpha 2b (platelet glycoprotein IIb of IIb/IIIa complex, antigen CD41) | 2.146 |
| NM_004931 | 405667 | CD8B | CD8b molecule | −1.785714286 |
| AI753792 | 502004 | RRAS2 | related RAS viral (r-ras) oncogene homolog 2 | −1.736111111 |
| AA149644 | 150718 | JAM3 | junctional adhesion molecule 3 | 1.424 |
| R64130 | 2164 | PPBP | pro-platelet basic protein (chemokine (C-X-C motif) ligand 7) | 1.75 |
| AW296309 | 405667 | CD8B | CD8b molecule | −1.526717557 |
| NM_020152 | 222802 | C21orf7 | chromosome 21 open reading frame 7 | 1.527 |
| BG251467 | 122514 | SLC25A37 | solute carrier family 25, member 37 | 1.444 |
| AL136805 | 278436 | TSHZ3 | teashirt family zinc finger 3 | 1.439 |
| AI520949 | 110675 | PVRL2 | poliovirus receptor-related 2 (herpesvirus entry mediator B) | 1.64 |
| W73230 | 200100 | C7orf41 | chromosome 7 open reading frame 41 | 1.489 |
| AI215106 | 591381 | INSR | Insulin receptor | 1.501 |
| AW270105 | 144309 | PCGF3 | Polycomb group ring finger 3 | 1.495 |
| BE867789 | 110675 | PVRL2 | poliovirus receptor-related 2 (herpesvirus entry mediator B) | 1.561 |
| BE867789 | 110675 | PVRL2 | poliovirus receptor-related 2 (herpesvirus entry mediator B) | 2.028 |
| AW167424 | 585653 | NUMB | Numb homolog (*Drosophila*) | 1.896 |
| AI971212 | 434494 | SYNJ2 | synaptojanin 2 | 1.443 |
| AA521086 | 99691 | ALPK1 | alpha-kinase 1 | 1.952 |

TABLE 2

| GenBank ID | Unigene | Common Name | Gene description |
|---|---|---|---|
| AA167449 | Hs.529901 | XIST | MRNA; cDNA DKFZp686K10163 (from clone DKFZp686K10163) |
| AV646597 | Hs.529901 | | MRNA; cDNA DKFZp686K10163 (from clone DKFZp686K10163) |
| NM_000607 | Hs.567311 | ORM1 | orosomucoid 1 |
| BE644917 | Hs.529901 | XIST | MRNA; cDNA DKFZp686K10163 (from clone DKFZp686K10163) |
| AA628440 | Hs.529901 | XIST | MRNA; cDNA DKFZp686K10163 (from clone DKFZp686K10163) |
| AI733564 | Hs.478588 | | Transcribed sequence with weak similarity to protein pir: A40138 (*H. sapiens*) A40138 glycogen phosphorylase |
| NM_000419 | Hs.411312 | ITGA2B | integrin, alpha 2b (platelet glycoprotein IIb of IIb/IIIa complex, antigen CD41B) |
| BE867789 | Hs.110675 | PVRL2 | poliovirus receptor-related 2 (herpesvirus entry mediator B) |
| AA521086 | Hs.99691 | LAK | lymphocyte alpha-kinase |
| AB023212 | Hs.158722 | PCNX | pecanex homolog (*Drosophila*) |
| AL109714 | Hs.459049 | LOC283687 | hypothetical protein LOC283687 |
| L10343 | | PI3 | elafin has been sequenced at the protein level; pre-elafin has not; its existence is assumed from its molecular weight (PAGE analysis); putative; *Homo sapiens* elafin precursor, gene, complete cds. |
| AW167424 | Hs.585653 | NUMB | numb homolog (*Drosophila*) |
| M35999 | Hs.218040 | ITGB3 | integrin, beta 3 (platelet glycoprotein IIIa, antigen CD61) |
| NM_002638 | Hs.112341 | PI3 | protease inhibitor 3, skin-derived (SKALP) |
| AI929792 | Hs.21374 | | Transcribed sequences |
| NM_000607 | Hs.567311 | ORM2 | orosomucoid 1 |
| R64130 | Hs.2164 | PPBP | pro-platelet basic protein (chemokine (C-X-C motif) ligand 7) |
| NM_003118 | Hs.111779 | SPARC | secreted protein, acidic, cysteine-rich (osteonectin) |
| NM_002736 | Hs.433068 | PRKAR2B | protein kinase, cAMP-dependent, regulatory, type II, beta |
| AA703239 | Hs.159430 | | Transcribed sequence with weak similarity to protein prf: 1303335A (*H. sapiens*) 1303335A decay accelerating factor long [*Homo sapiens*] |
| NM_004666 | Hs.12114 | VNN1 | vanin 1 |
| NM_016348 | Hs.519694 | C5orf4 | chromosome 5 open reading frame 4 |
| BI868572 | | DKFZp686I15217 | 603392679F1 NIH_MGC_90 *Homo sapiens* cDNA clone IMAGE: 5402706 5′, mRNA sequence. |
| AW205418 | Hs.495097 | KIAA2025 | KIAA2025 protein |
| NM_001999 | Hs.519294 | FBN2 | fibrillin 2 (congenital contractural arachnodactyly) |
| AI520949 | Hs.110675 | PVRL2 | poliovirus receptor-related 2 (herpesvirus entry mediator B) |
| M25915 | Hs.436657 | CLU | clusterin (complement lysis inhibitor, SP-40, 40, sulfated glycoprotein 2, testosterone-repressed prostate message 2, apolipoprotein J) |
| BF055462 | Hs.164226 | THBS1 | thrombospondin 1 |
| AI679555 | Hs.527653 | | Transcribed sequence with weak similarity to protein ref: NP_060312.1 (*H. sapiens*) hypothetical protein FLJ20489 [*Homo sapiens*] |
| AW051321 | Hs.464137 | | CDNA FLJ30303 fis, clone BRACE2003269 |
| NM_000129 | Hs.335513 | F13A1 | coagulation factor XIII, A1 polypeptide |
| BE896490 | Hs.595327 | SNAP29 | synaptosomal-associated protein, 29 kDa |
| NM_000697 | Hs.422967 | ALOX12 | arachidonate 12-lipoxygenase |
| AA181060 | Hs.349283 | | Clone IMAGE: 5288883, mRNA |
| NM_002619 | Hs.81564 | PF4 | platelet factor 4 (chemokine (C-X-C motif) ligand 4) |
| AU157823 | | PYGL | AU157823 PLACE1 *Homo sapiens* cDNA clone PLACE1009595 3′, mRNA sequence. |
| BE867789 | Hs.110675 | PVRL2 | poliovirus receptor-related 2 (herpesvirus entry mediator B) |
| AA526844 | Hs.556600 | MYLK | MSTP083 mRNA, complete cds |
| BF435438 | Hs.80720 | | Full length insert cDNA YH93B03 |

TABLE 2-continued

| GenBank ID | Unigene | Common Name | Gene description |
|---|---|---|---|
| NM_005231 | Hs.632133 | EMS1 | ems1 sequence (mammary tumor and squamous cell carcinoma-associated (p80/85 src substrate) |
| NM_007150 | Hs.16622 | ZNF185 | zinc finger protein 185 (LIM domain) |
| NM_001928 | Hs.155597 | DF | D component of complement (adipsin) |
| NM_003831 | Hs.445511 | RIOK3 | RIO kinase 3 (yeast) |
| NM_022763 | Hs.159430 | FAD104 | FAD104 |
| NM_001343 | Hs.481980 | DAB2 | disabled homolog 2, mitogen-responsive phosphoprotein (*Drosophila*) |
| NM_020152 | Hs.222802 | C21orf7 | chromosome 21 open reading frame 7 |
| BC029493 | Hs.369265 | IRAK3 | interleukin-1 receptor-associated kinase 3 |
| BF976693 | Hs.376675 | | CDNA FLJ34100 fis, clone FCBBF3007597 |
| NM_000945 | Hs.280604 | PPP3R1 | protein phosphatase 3 (formerly 2B), regulatory subunit B, 19 kDa, alpha isoform (calcineurin B, type I) |
| AI215106 | Hs.591381 | INSR | insulin receptor |
| X82240 | Hs.2484 | TCL1A | T-cell leukemia/lymphoma 1A |
| AW296309 | Hs.405667 | CD8B1 | CD8 antigen, beta polypeptide 1 (p37) |
| M85256 | Hs.554197 | IGKC | Isolate donor Z clone Z55K immunoglobulin kappa light chain variable region mRNA, partial cds |
| AF439512 | Hs.387787 | KLRK1 | killer cell lectin-like receptor subfamily K, member 1 |
| NM_005442 | Hs.591663 | EOMES | eomesodermin homolog (*Xenopus laevis*) |
| AI424825 | Hs.435052 | ATP8A1 | ATPase, aminophospholipid transporter (APLT), Class I, type 8A, member 1 |
| NM_006159 | Hs.505326 | NELL2 | NEL-like 2 (chicken) |
| BI547087 | | | 603190322F1 NIH_MGC_95 Homo sapiens cDNA clone IMAGE: 5261717 5', mRNA sequence. |
| BC001872 | Hs.510635 | IGHM | synonym: MU; *Homo sapiens* immunoglobulin heavy constant mu, mRNA (cDNA clone MGC: 1228 IMAGE: 3544448), complete cds. |
| AW006735 | Hs.85258 | CD8A | CD8 antigen, alpha polypeptide (p32) |
| NM_007360 | Hs.387787 | KLRK1 | killer cell lectin-like receptor subfamily K, member 1 |
| NM_002261 | Hs.74082 | KLRC3 | synonyms: NKG2E, NKG2-E; isoform NKG2-E is encoded by transcript variant NKG2-E; go_component: integral to membrane [goid 0016021] [evidence IEA]; go_function: transmembrane receptor activity [goid 0004888] [evidence TAS] [pmid 9683661]; go_function: lectin [goid 0005530] [evidence IEA]; go_function: sugar binding [goid 0005529] [evidence IEA]; go_process: cellular defense response [goid 0006968] [evidence TAS] [pmid 9683661]; go_process: heterophilic cell adhesion [goid 0007157] [evidence IEA]; *Homo sapiens* killer cell lectin-like receptor subfamily C, member 3 (KLRC3), transcript variant NKG2-E, mRNA. |
| M13231 | Hs.534032 | TRGV9 | T cell receptor gamma locus |
| AI753792 | Hs.502004 | RRAS2 | related RAS viral (r-ras) oncogene homolog 2 |
| M16768 | Hs.534032 | TRGV9 | T-cell receptor (V-J-C) precursor; Human T-cell receptor gamma chain VJCI-CII-CIII region mRNA, complete cds. |
| NM_003175 | Hs.458346 | XCL1 | chemokine (C motif) ligand 2 |
| U96394 | Hs.449601 | IGL@ | Clone P2-147 anti-oxidized LDL immunoglobulin light chain Fab mRNA, partial cds |
| M27331 | Hs.534032 | TRGV9 | T cell receptor gamma locus |
| U23772 | Hs.546295 | XCL1 | chemokine (C motif) ligand 1 |
| NM_004931 | Hs.405667 | CD8B1 | CD8 antigen, beta polypeptide 1 (p37) |
| NM_006275 | Hs.6891 | SFRS6 | splicing factor, arginine/serine-rich 6 |
| BC020552 | Hs.379186 | PDCD6 | programmed cell death 6 |
| NM_001548 | Hs.20315 | IFIT1 | interferon-induced protein with tetratricopeptide repeats 1 |
| BC005248 | Hs.461178 | EIF1AY | eukaryotic translation initiation factor 1A, Y-linked |
| NM_004660 | Hs.99120 | DDX3Y | DEAD (Asp-Glu-Ala-Asp) box polypeptide 3, Y-linked |
| NM_001008 | Hs.282376 | RPS4Y1 | ribosomal protein S4, Y-linked |

TABLE 3

| GenBank ID | Unigene | Common Name | Gene description |
|---|---|---|---|
| AI733564 | Hs.478588 | | Transcribed sequence with weak similarity to protein pir: A40138 (*H. sapiens*) A40138 glycogen phosphorylase |
| NM_000419 | Hs.411312 | ITGA2B | integrin, alpha 2b (platelet glycoprotein IIb of IIb/IIIa complex, antigen CD41B) |
| BE867789 | Hs.110675 | PVRL2 | poliovirus receptor-related 2 (herpesvirus entry mediator B) |
| AA521086 | Hs.99691 | LAK | lymphocyte alpha-kinase |
| AW167424 | Hs.585653 | NUMB | numb homolog (*Drosophila*) |
| R64130 | Hs.2164 | PPBP | pro-platelet basic protein (chemokine (C-X-C motif) ligand 7) |
| BI868572 | | DKFZp686I15217 | 603392679F1 NIH_MGC_90 Homo sapiens cDNA clone IMAGE: 5402706 5', mRNA sequence. |
| NM_001999 | Hs.519294 | FBN2 | fibrillin 2 (congenital contractural arachnodactyly) |
| AI520949 | Hs.110675 | PVRL2 | poliovirus receptor-related 2 (herpesvirus entry mediator B) |
| AW051321 | Hs.464137 | | CDNA FLJ30303 fis, clone BRACE2003269 |
| BE896490 | Hs.595327 | SNAP29 | synaptosomal-associated protein, 29 kDa |
| AA181060 | Hs.349283 | | Clone IMAGE: 5288883, mRNA |
| BE867789 | Hs.110675 | PVRL2 | poliovirus receptor-related 2 (herpesvirus entry mediator B) |
| NM_007150 | Hs.16622 | ZNF185 | zinc5t finger protein 185 (LIM domain) |
| NM_001928 | Hs.155597 | DF | D component of complement (adipsin) |
| NM_001343 | Hs.481980 | DAB2 | disabled homolog 2, mitogen-responsive phosphoprotein (*Drosophila*) |

TABLE 3-continued

| GenBank ID | Unigene | Common Name | Gene description |
|---|---|---|---|
| NM_020152 | Hs.222802 | C21orf7 | chromosome 21 open reading frame 7 |
| BF976693 | Hs.376675 | | CDNA FLJ34100 fis, clone FCBBF3007597 |
| NM_000945 | Hs.280604 | PPP3R1 | protein phosphatase 3 (formerly 2B), regulatory subunit B, 19 kDa, alpha isoform (calcineurin B, type I) |
| AI215106 | Hs.591381 | INSR | insulin receptor |
| AW270105 | Hs.643902 | RNF3 | ring finger protein 3 |
| W73230 | Hs.200100 | Ells1 | zd56c09.s1 Soares_fetal_heart_NbHH19W *Homo sapiens* cDNA clone IMAGE: 344656 3' similar to contains element MER10 repetitive element;, mRNA sequence. |
| NM_017526 | Hs.23581 | OBRGRP | leptin receptor |
| AW205122 | Hs.496572 | FLJ22679 | hypothetical protein FLJ22679 |
| BC003064 | Hs.481980 | DAB2 | disabled homolog 2, mitogen-responsive phosphoprotein (*Drosophila*) |
| N63920 | Hs.596025 | | CDNA clone IMAGE: 5294823, partial cds |
| BG251467 | Hs.122514 | MSCP | mitochondrial solute carrier protein |
| AI971212 | Hs.434494 | SYNJ2 | synaptojanin 2 |
| AL136805 | Hs.278436 | ZNF537 | zinc finger protein 537 |
| AA149644 | Hs.150718 | JAM3 | junctional adhesion molecule 3 |
| AW665656 | Hs.633892 | GLUL | glutamate-ammonia ligase (glutamine synthase) |
| NM_003897 | Hs.591785 | IER3 | immediate early response 3 |
| NM_004536 | Hs.191356 | BIRC1 | baculoviral IAP repeat-containing 1 |
| AI719730 | Hs.24258 | GUCY1A3 | guanylate cyclase 1, soluble, alpha 3 |
| AW796364 | Hs.371594 | MKNK1 | Transcribed sequence with weak similarity to protein ref: NP_060265.1 (*H. sapiens*) hypothetical protein FLJ20378 [*Homo sapiens*] |
| BC043380 | Hs.468274 | | CDNA clone IMAGE: 5223469, partial cds |
| AA482548 | Hs.497873 | WDR26 | zt34b03.s1 Soares ovary tumor NbHOT *Homo sapiens* cDNA clone IMAGE: 724205 3', mRNA sequence. |
| AI476341 | Hs.93825 | | CDNA FLJ39784 fis, clone SPLEN2002314 |
| NM_009590 | Hs.143102 | AOC2 | amine oxidase, copper containing 2 (retina-specific) |
| AA218974 | | LOC158563 | zr02g12.s1 Stratagene NT2 neuronal precursor 937230 *Homo sapiens* cDNA clone IMAGE: 650374 3', mRNA sequence. |
| AA010315 | Hs.60371 | | Transcribed sequences |
| BE439987 | Hs.462214 | GAS7 | growth arrest-specific 7 |
| AI356228 | Hs.515351 | KIAA1533 | KIAA1533 |
| AK023845 | | USP34 | ubiquitin specific protease 34 |
| AI650285 | Hs.287299 | | Transcribed sequence with weak similarity to protein ref: NP_060312.1 (*H. sapiens*) hypothetical protein FLJ20489 [*Homo sapiens*] |
| BE221883 | Hs.11184 | UBE2R2 | ubiquitin-conjugating enzyme E2R 2 |
| BG337478 | Hs.128037 | | CDNA FLJ38117 fis, clone D3OST2003797 |
| AV723666 | | EFCBP2 | AV723666 HTB *Homo sapiens* cDNA clone HTBABA11 5', mRNA sequence. |
| BG334495 | Hs.631749 | LOC284021 | hypothetical protein LOC284021 |
| AI962978 | Hs.469244 | WASF2 | WAS protein family, member 2 |
| AW297879 | Hs.436271 | | Transcribed sequences |
| NM_000313 | Hs.64016 | PROS1 | protein S (alpha) |
| BF446281 | Hs.433307 | BCKDHA | branched chain keto acid dehydrogenase E1, alpha polypeptide (maple syrup urine disease) |
| AI476341 | Hs.93825 | | CDNA FLJ39784 fis, clone SPLEN2002314 |
| NM_002413 | Hs.81874 | MGST2 | microsomal glutathione S-transferase 2 |
| AI698731 | Hs.202238 | | Transcribed sequences |
| BM849515 | Hs.636486 | LRRK1 | leucine-rich repeat kinase 1 |
| AK096134 | Hs.378150 | | Chromosome 4 unknown transcript 1 variant 2 mRNA, partial sequence, alternatively spliced |
| AV700946 | Hs.432337 | | Transcribed sequence with weak similarity to protein pir: I49130 (*M. musculus*) I49130 reverse transcriptase - mouse |
| BE083088 | Hs.591602 | SSFA2 | RC2-BT0642-030400-021-c05 BT0642 *Homo sapiens* cDNA, mRNA sequence. |
| AF315688 | Hs.591083 | IFNK | interferon, kappa |
| BC013319 | Hs.506381 | FGD6 | FYVE, RhoGEF and PH domain containing 6 |
| NM_018407 | Hs.492314 | LAPTM4B | lysosomal associated protein transmembrane 4 beta |
| BC026969 | Hs.492716 | MGC21654 | *Homo sapiens* unknown MGC21654 product, mRNA (cDNA clone IMAGE: 5116073), partial cds. |
| BC015590 | Hs.382046 | | CDNA clone IMAGE: 4643842, partial cds |
| NM_014015 | Hs.592051 | DEXI | dexamethasone-induced transcript |
| AW572279 | Hs.515840 | DNMT3A | DNA (cytosine-5-)-methyltransferase 3 alpha |
| AL359941 | Hs.593311 | | programmed cell death 6 |
| BC019022 | Hs.531856 | dJ383J4.3 | hypothetical gene supported by BC007071 |
| AI692169 | Hs.379186 | PDCD6 | wd37e07.x1 Soares_NFL_T_GBC_S1 *Homo sapiens* cDNA clone IMAGE: 2330340 3', mRNA sequence. |
| AC006033 | | | *Homo sapiens*, Similar to steroidogenic acute regulatory protein related, clone MGC: 3251 IMAGE: 3505985, mRNA, complete cds.; H_NH0121A08.9 This gene was based on gi(13111773 13543614 14042926); *Homo sapiens* BAC clone RP11-121A8 from 7, complete sequence. |
| AL521959 | Hs.487479 | PSCD3 | pleckstrin homology, Sec7 and coiled-coil domains 3 |
| W67995 | Hs.54943 | FXC1 | fracture callus 1 homolog (rat) |
| AW083371 | Hs.173878 | NIPSNAP1 | nipsnap homolog 1 (*C. elegans*) |
| AF044954 | Hs.513266 | NDUFB10 | NADH dehydrogenase (ubiquinone) 1 beta subcomplex, 10, 22 kDa |
| AI347139 | Hs.8162 | MGC39372 | hypothetical protein MGC39372 |
| AK074465 | Hs.462833 | FLJ31952 | hypothetical protein FLJ31952 |

TABLE 3-continued

| GenBank ID | Unigene | Common Name | Gene description |
|---|---|---|---|
| AI609285 | Hs.503891 | USP28 | tw83h09.x1 NCI_CGAP_HN5 Homo sapiens cDNA clone IMAGE: 2266337 3' similar to contains Alu repetitive element; contains element MER29 repetitive element;, mRNA sequence. |
| NM_000107 | Hs.643521 | DDB2 | damage-specific DNA binding protein 2, 48 kDa |
| NM_005317 | Hs.465511 | GZMM | granzyme M (lymphocyte met-ase 1) |
| BC040914 | Hs.322462 | | Clone IMAGE: 5745627, mRNA |
| AK001164 | Hs.599785 | | CDNA FLJ10302 fis, clone NT2RM2000042 |
| NM_005608 | Hs.155975 | PTPRCAP | protein tyrosine phosphatase, receptor type, C-associated protein |
| NM_013330 | Hs.642710 | NME7 | non-metastatic cells 7, protein expressed in (nucleoside-diphosphate kinase) |
| AB020630 | Hs.45719 | PPP1R16B | protein phosphatase 1, regulatory (inhibitor) subunit 16B |
| AB020630 | Hs.45719 | PPP1R16B | protein phosphatase 1, regulatory (inhibitor) subunit 16B |
| AF298547 | Hs.369279 | NALP2 | NACHT, leucine rich repeat and PYD containing 2 |
| AW157571 | Hs.479066 | MARLIN1 | multiple coiled-coil GABABR1-binding protein |
| AA767131 | Hs.121432 | KIAA0073 | KIAA0073 protein |
| NM_004356 | Hs.54457 | CD81 | CD81 antigen (target of antiproliferative antibody 1) |
| AI702465 | Hs.23606 | | Transcribed sequences |
| U90339 | Hs.584739 | ADK | adenosine kinase |
| AW296309 | Hs.405667 | CD8B1 | CD8 antigen, beta polypeptide 1 (p37) |
| AI753792 | Hs.502004 | RRAS2 | related RAS viral (r-ras) oncogene homolog 2 |
| NM_004931 | Hs.405667 | CD8B1 | CD8 antigen, beta polypeptide 1 (p37) |

TABLE 4

| GenBank ID | Unigene ID | Common Name | Gene Description |
|---|---|---|---|
| AA167449 | Hs.529901 | XIST | MRNA; cDNA DKFZp686K10163 (from clone DKFZp686K10163) |
| AV646597 | Hs.529901 | | MRNA; cDNA DKFZp686K10163 (from clone DKFZp686K10163) |
| NM_000607 | Hs.567311 | ORM1 | orosomucoid 1 |
| BE644917 | Hs.529901 | XIST | MRNA; cDNA DKFZp686K10163 (from clone DKFZp686K10163) |
| AA628440 | Hs.529901 | XIST | MRNA; cDNA DKFZp686K10163 (from clone DKFZp686K10163) |
| AI733564 | Hs.478588 | | Transcribed sequence with weak similarity to protein pir: A40138 (H. sapiens) A40138 glycogen phosphorylase |
| NM_000419 | Hs.411312 | ITGA2B | integrin, alpha 2b (platelet glycoprotein IIb of IIb/IIIa complex, antigen CD41B) |
| BE867789 | Hs.110675 | PVRL2 | poliovirus receptor-related 2 (herpesvirus entry mediator B) |
| AA521086 | Hs.99691 | LAK | lymphocyte alpha-kinase |
| AB023212 | Hs.158722 | PCNX | pecanex homolog (Drosophila) |
| AL109714 | Hs.459049 | LOC283687 | hypothetical protein LOC283687 |
| L10343 | | PI3 | elafin has been sequenced at the protein level; pre-elafin has not; its existence is assumed from its molecular weight (PAGE analysis); putative; Homo sapiens elafin precursor, gene, complete cds. |
| AW167424 | Hs.585653 | NUMB | numb homolog (Drosophila) |
| M35999 | Hs.218040 | ITGB3 | integrin, beta 3 (platelet glycoprotein IIIa, antigen CD61) |
| NM_002638 | Hs.112341 | PI3 | protease inhibitor 3, skin-derived (SKALP) |
| AI929792 | Hs.21374 | | Transcribed sequences |
| NM_000607 | Hs.567311 | ORM2 | orosomucoid 1 |
| R64130 | Hs.2164 | PPBP | pro-platelet basic protein (chemokine (C-X-C motif) ligand 7) |
| NM_003118 | Hs.111779 | SPARC | secreted protein, acidic, cysteine-rich (osteonectin) |
| NM_002736 | Hs.433068 | PRKAR2B | protein kinase, cAMP-dependent, regulatory, type II, beta |
| AA703239 | Hs.159430 | | Transcribed sequence with weak similarity to protein prf: 1303335A (H. sapiens) 1303335A decay accelerating factor long [Homo sapiens] |
| NM_004666 | Hs.12114 | VNN1 | vanin 1 |
| NM_016348 | Hs.519694 | C5orf4 | chromosome 5 open reading frame 4 |
| BI868572 | | DKFZp686I15217 | 603392679F1 NIH_MGC_90 Homo sapiens cDNA clone IMAGE: 5402706 5', mRNA sequence. |
| AW205418 | Hs.495097 | KIAA2025 | KIAA2025 protein |
| NM_001999 | Hs.519294 | FBN2 | fibrillin 2 (congenital contractural arachnodactyly) |
| AI520949 | Hs.110675 | PVRL2 | poliovirus receptor-related 2 (herpesvirus entry mediator B) |
| M25915 | Hs.436657 | CLU | clusterin (complement lysis inhibitor, SP-40, 40, sulfated glycoprotein 2, testosterone-repressed prostate message 2, apolipoprotein J) |
| BF055462 | Hs.164226 | THBS1 | thrombospondin 1 |
| AI679555 | Hs.527653 | | Transcribed sequence with weak similarity to protein ref: NP_060312.1 (H. sapiens) hypothetical protein FLJ20489 [Homo sapiens] |
| AW051321 | Hs.464137 | | CDNA FLJ30303 fis, clone BRACE2003269 |
| NM_000129 | Hs.335513 | F13A1 | coagulation factor XIII, A1 polypeptide |
| BE896490 | Hs.595327 | SNAP29 | synaptosomal-associated protein, 29 kDa |
| NM_000697 | Hs.422967 | ALOX12 | arachidonate 12-lipoxygenase |
| AA181060 | Hs.349283 | | Clone IMAGE: 5288883, mRNA |
| NM_002619 | Hs.81564 | PF4 | platelet factor 4 (chemokine (C-X-C motif) ligand 4) |
| AU157823 | | PYGL | AU157823 PLACE1 Homo sapiens cDNA clone PLACE1009595 3', mRNA sequence. |
| BE867789 | Hs.110675 | PVRL2 | poliovirus receptor-related 2 (herpesvirus entry mediator B) |
| AA526844 | Hs.556600 | MYLK | MSTP083 mRNA, complete cds |
| BF435438 | Hs.80720 | | Full length insert cDNA YH93B03 |
| NM_005231 | Hs.632133 | EMS1 | ems1 sequence (mammary tumor and squamous cell carcinoma-associated (p80/85 src substrate) |

TABLE 4-continued

| GenBank ID | Unigene ID | Common Name | Gene Description |
|---|---|---|---|
| NM_007150 | Hs.16622 | ZNF185 | zinc finger protein 185 (LIM domain) |
| NM_001928 | Hs.155597 | DF | D component of complement (adipsin) |
| NM_003831 | Hs.445511 | RIOK3 | RIO kinase 3 (yeast) |
| NM_022763 | Hs.159430 | FAD104 | FAD104 |
| NM_001343 | Hs.481980 | DAB2 | disabled homolog 2, mitogen-responsive phosphoprotein (*Drosophila*) |
| NM_020152 | Hs.222802 | C21orf7 | chromosome 21 open reading frame 7 |
| BC029493 | Hs.369265 | IRAK3 | interleukin-1 receptor-associated kinase 3 |
| BF976693 | Hs.376675 | | CDNA FLJ34100 fis, clone FCBBF3007597 |
| NM_000945 | Hs.280604 | PPP3R1 | protein phosphatase 3 (formerly 2B), regulatory subunit B, 19 kDa, alpha isoform (calcineurin B, type I) |
| AI215106 | Hs.591381 | INSR | insulin receptor |
| AI817801 | Hs.191356 | BIRC1 | Transcribed sequence with strong similarity to protein sp: Q13075 (*H. sapiens*) BIR1_HUMAN Baculoviral IAP repeat-containing protein 1 |
| AW270105 | Hs.643902 | RNF3 | ring finger protein 3 |
| BG913589 | Hs.59214 | LOC144871 | DnaJ (Hsp40) homolog, subfamily C, member 3 |
| W73230 | Hs.200100 | Ells1 | zd56c09.s1 Soares_fetal_heart_NbHH19W Homo sapiens cDNA clone IMAGE: 344656 3' similar to contains element MER10 repetitive element;, mRNA sequence. |
| BF691447 | Hs.644051 | B4GALT5 | UDP-Gal: betaGlcNAc beta 1,4- galactosyltransferase, polypeptide 5 |
| NM_005502 | Hs.429294 | ABCA1 | ATP-binding cassette, sub-family A (ABC1), member 1 |
| NM_000361 | Hs.2030 | THBD | thrombomodulin |
| AK024569 | Hs.195403 | DOCK5 | dedicator of cytokinesis 5 |
| AB051833 | Hs.123239 | ACRBP | acrosin binding protein |
| NM_004126 | Hs.83381 | GNG11 | guanine nucleotide binding protein (G protein), gamma 11 |
| Y07846 | Hs.322852 | GAS2L1 | growth arrest-specific 2 like 1 |
| BE327727 | Hs.443301 | | Transcribed sequences |
| M36532 | Hs.155097 | CA2 | carbonic anhydrase II |
| NM_017526 | Hs.23581 | OBRGRP | leptin receptor |
| AW205122 | Hs.496572 | FLJ22679 | hypothetical protein FLJ22679 |
| AI141116 | Hs.123239 | ACRBP | acrosin binding protein |
| AW293296 | Hs.163893 | | Transcribed sequences |
| N63244 | Hs.592143 | TUBB1 | tubulin, beta 1 |
| BG120535 | | VNN1 | 602346858F1 NIH_MGC_90 Homo sapiens cDNA clone IMAGE: 4441695 5', mRNA sequence. |
| AU152763 | Hs.586165 | | CDNA FLJ10742 fis, clone NT2RP3001629 |
| BC003064 | Hs.481980 | DAB2 | disabled homolog 2, mitogen-responsive phosphoprotein (*Drosophila*) |
| N63920 | Hs.596025 | | CDNA clone IMAGE: 5294823, partial cds |
| BG251467 | Hs.122514 | MSCP | mitochondrial solute carrier protein |
| AF237762 | Hs.306199 | GPR84 | G protein-coupled receptor 84 |
| AW206560 | Hs.609146 | | Transcribed sequences |
| AI971212 | Hs.434494 | SYNJ2 | synaptojanin 2 |
| AL136805 | Hs.278436 | ZNF537 | zinc finger protein 537 |
| BC026299 | Hs.518727 | | Clone IMAGE: 4275461, mRNA |
| BE675324 | Hs.200770 | | Transcribed sequences |
| NM_021647 | Hs.178121 | KIAA0626 | |
| NM_018482 | Hs.106015 | DDEF1 | synonyms: PAP, PAG2, ASAP1, ZG14P, KIAA1249; Homo sapiens development and differentiation enhancing factor 1 (DDEF1), mRNA. |
| AA149644 | Hs.150718 | JAM3 | junctional adhesion molecule 3 |
| AF325460 | Hs.351812 | CLECSF7 | C-type (calcium dependent, carbohydrate-recognition domain) lectin, superfamily member 7 |
| AW665656 | Hs.633892 | GLUL | glutamate-ammonia ligase (glutamine synthase) |
| AA417099 | Hs.465709 | | Transcribed sequences |
| NM_003897 | Hs.591785 | IER3 | immediate early response 3 |
| AF275260 | Hs.592117 | CXCL16 | chemokine (C-X-C motif) ligand 16 |
| AF001540 | | MALAT-1 | PRO1073 protein |
| AI640434 | Hs.601545 | FLJ10357 | hypothetical protein FLJ10357 |
| AW043859 | Hs.235795 | | Clone IMAGE: 5263020, mRNA |
| H68759 | Hs.122514 | | Transcribed sequences |
| NM_004536 | Hs.191356 | BIRC1 | baculoviral IAP repeat-containing 1 |
| AF086010 | Hs.335205 | | Full length insert cDNA clone YW04H08 |
| NM_003189 | Hs.73828 | TAL1 | T-cell acute lymphocytic leukemia 1 |
| AW138767 | Hs.274256 | ELOVL7 | hypothetical protein FLJ23563 |
| NM_003693 | Hs.534497 | SCARF1 | scavenger receptor class F, member 1 |
| BG177759 | Hs.497873 | WDR26 | WD repeat domain 26 |
| U49396 | Hs.408615 | P2RX5 | purinergic receptor P2X, ligand-gated ion channel, 5 |
| AA781795 | Hs.546467 | EPSTI1 | epithelial stromal interaction 1 (breast) |
| BF433219 | | | Transcribed sequences |
| BC003574 | Hs.2484 | TCL1A | T-cell leukemia/lymphoma 1A |
| AB051458 | Hs.419171 | KIAA1671 | KIAA1671 protein |
| NM_004114 | Hs.6540 | FGF13 | fibroblast growth factor 13 |
| BF446578 | Hs.125293 | RASGEF1A | RasGEF domain family, member 1A |
| AA931562 | Hs.444049 | | Transcribed sequence with weak similarity to protein ref: NP_060312.1 (*H. sapiens*) hypothetical protein FLJ20489 [*Homo sapiens*] |
| BF514552 | Hs.292449 | FCRH3 | Fc receptor-like protein 3 |
| X82240 | Hs.2484 | TCL1A | T-cell leukemia/lymphoma 1A |
| AW296309 | Hs.405667 | CD8B1 | CD8 antigen, beta polypeptide 1 (p37) |
| M85256 | Hs.554197 | IGKC | Isolate donor Z clone Z55K immunoglobulin kappa light chain variable region mRNA, partial cds |

TABLE 4-continued

| GenBank ID | Unigene ID | Common Name | Gene Description |
|---|---|---|---|
| AF439512 | Hs.387787 | KLRK1 | killer cell lectin-like receptor subfamily K, member 1 |
| NM_005442 | Hs.591663 | EOMES | eomesodermin homolog (*Xenopus laevis*) |
| AI424825 | Hs.435052 | ATP8A1 | ATPase, aminophospholipid transporter (APLT), Class I, type 8A, member 1 |
| NM_006159 | Hs.505326 | NELL2 | NEL-like 2 (chicken) |
| BI547087 | | | 603190322F1 NIH_MGC_95 *Homo sapiens* cDNA clone IMAGE: 5261717 5', mRNA sequence. |
| BC001872 | Hs.510635 | IGHM | synonym: MU; *Homo sapiens* immunoglobulin heavy constant mu, mRNA (cDNA clone MGC: 1228 IMAGE: 3544448), complete cds. |
| AW006735 | Hs.85258 | CD8A | CD8 antigen, alpha polypeptide (p32) |
| NM_007360 | Hs.387787 | KLRK1 | killer cell lectin-like receptor subfamily K, member 1 |
| NM_002261 | Hs.74082 | KLRC3 | synonyms: NKG2E, NKG2-E; isoform NKG2-E is encoded by transcript variant NKG2-E; go_component: integral to membrane [goid 0016021] [evidence IEA]; go_function: transmembrane receptor activity [goid 0004888] [evidence TAS] [pmid 9683661]; go_function: lectin [goid 0005530] [evidence IEA]; go_function: sugar binding [goid 0005529] [evidence IEA]; go_process: cellular defense response [goid 0006968] [evidence TAS] [pmid 9683661]; go_process: heterophilic cell adhesion [goid 0007157] [evidence IEA]; *Homo sapiens* killer cell lectin-like receptor subfamily C, member 3 (KLRC3), transcript variant NKG2-E, mRNA. |
| M13231 | Hs.534032 | TRGV9 | T cell receptor gamma locus |
| AI753792 | Hs.502004 | RRAS2 | related RAS viral (r-ras) oncogene homolog 2 |
| M16768 | Hs.534032 | TRGV9 | T-cell receptor (V-J-C) precursor: Human T-cell receptor gamma chain VJCI-CII-CIII region mRNA, complete cds. |
| NM_003175 | Hs.458346 | XCL1 | chemokine (C motif) ligand 2 |
| U96394 | Hs.449601 | IGL@ | Clone P2-147 anti-oxidized LDL immunoglobulin light chain Fab mRNA, partial cds |
| M27331 | Hs.534032 | TRGV9 | T cell receptor gamma locus |
| U23772 | Hs.546295 | XCL1 | chemokine (C motif) ligand 1 |
| NM_004931 | Hs.405667 | CD8B1 | CD8 antigen, beta polypeptide 1 (p37) |
| NM_006275 | Hs.6891 | SFRS6 | splicing factor, arginine/serine-rich 6 |
| BC020552 | Hs.379186 | PDCD6 | programmed cell death 6 |
| NM_001548 | Hs.20315 | IFIT1 | interferon-induced protein with tetratricopeptide repeats 1 |
| BC005248 | Hs.461178 | EIF1AY | eukaryotic translation initiation factor 1A, Y-linked |
| NM_004660 | Hs.99120 | DDX3Y | DEAD (Asp-Glu-Ala-Asp) box polypeptide 3, Y-linked |
| NM_001008 | Hs.282376 | RPS4Y1 | ribosomal protein S4, Y-linked |

TABLE 5

| GenBank ID | Unigene ID | Common Name | Gene Description |
|---|---|---|---|
| AA167449 | Hs.529901 | XIST | MRNA; cDNA DKFZp686K10163 (from clone DKFZp686K10163) |
| AV646597 | Hs.529901 | | MRNA; cDNA DKFZp686K10163 (from clone DKFZp686K10163) |
| NM_000607 | Hs.567311 | ORM1 | orosomucoid 1 |
| BE644917 | Hs.529901 | XIST | MRNA; cDNA DKFZp686K10163 (from clone DKFZp686K10163) |
| AA628440 | Hs.529901 | XIST | MRNA; cDNA DKFZp686K10163 (from clone DKFZp686K10163) |
| AI733564 | Hs.478588 | | Transcribed sequence with weak similarity to protein pir: A40138 (*H. sapiens*) A40138 glycogen phosphorylase |
| NM_000419 | Hs.411312 | ITGA2B | integrin, alpha 2b (platelet glycoprotein IIb of IIb/IIIa complex, antigen CD41B) |
| BE867789 | Hs.110675 | PVRL2 | poliovirus receptor-related 2 (herpesvirus entry mediator B) |
| AA521086 | Hs.99691 | LAK | lymphocyte alpha-kinase |
| AB023212 | Hs.158722 | PCNX | pecanex homolog (*Drosophila*) |
| AL109714 | Hs.459049 | LOC283687 | hypothetical protein LOC283687 |
| L10343 | | PI3 | elafin has been sequenced at the protein level: pre-elafin has not: its existence is assumed from its molecular weight (PAGE analysis); putative: *Homo sapiens* elafin precursor, gene, complete cds. |
| AW167424 | Hs.585653 | NUMB | numb homolog (*Drosophila*) |
| M35999 | Hs.218040 | ITGB3 | integrin, beta 3 (platelet glycoprotein IIIa, antigen CD61) |
| NM_002638 | Hs.112341 | PI3 | protease inhibitor 3, skin-derived (SKALP) |
| AI929792 | Hs.21374 | | Transcribed sequences |
| NM_000607 | Hs.567311 | ORM2 | orosomucoid 1 |
| R64130 | Hs.2164 | PPBP | pro-platelet basic protein (chemokine (C-X-C motif) ligand 7) |
| NM_003118 | Hs.111779 | SPARC | secreted protein, acidic, cysteine-rich (osteonectin) |
| NM_002736 | Hs.433068 | PRKAR2B | protein kinase, cAMP-dependent, regulatory, type II, beta |
| AA703239 | Hs.159430 | | Transcribed sequence with weak similarity to protein prf: 1303335A (*H. sapiens*) 1303335A decay accelerating factor long [*Homo sapiens*] |
| NM_004666 | Hs.12114 | VNN1 | vanin 1 |
| NM_016348 | Hs.519694 | C5orf4 | chromosome 5 open reading frame 4 |
| BI868572 | | DKFZp686I15217 | 603392679F1 NIH_MGC_90 *Homo sapiens* cDNA clone IMAGE: 5402706 5', mRNA sequence. |
| AW205418 | Hs.495097 | KIAA2025 | KIAA2025 protein |
| NM_001999 | Hs.519294 | FBN2 | fibrillin 2 (congenital contractural arachnodactyly) |
| AI520949 | Hs.110675 | PVRL2 | poliovirus receptor-related 2 (herpesvirus entry mediator B) |
| M25915 | Hs.436657 | CLU | clusterin (complement lysis inhibitor, SP-40, 40, sulfated glycoprotein 2, testosterone-repressed prostate message 2, apolipoprotein J) |

TABLE 5-continued

| GenBank ID | Unigene ID | Common Name | Gene Description |
|---|---|---|---|
| BF055462 | Hs.164226 | THBS1 | thrombospondin 1 |
| AI679555 | Hs.527653 | | Transcribed sequence with weak similarity to protein ref: NP_060312.1 (*H. sapiens*) hypothetical protein FLJ20489 [*Homo sapiens*] |
| AW051321 | Hs.464137 | | CDNA FLJ30303 fis, clone BRACE2003269 |
| NM_000129 | Hs.335513 | F13A1 | coagulation factor XIII, A1 polypeptide |
| BE896490 | Hs.595327 | SNAP29 | synaptosomal-associated protein, 29 kDa |
| NM_000697 | Hs.422967 | ALOX12 | arachidonate 12-lipoxygenase |
| AA181060 | Hs.349283 | | Clone IMAGE: 5288883, mRNA |
| NM_002619 | Hs.81564 | PF4 | platelet factor 4 (chemokine (C-X-C motif) ligand 4) |
| AU157823 | | PYGL | AU157823 PLACE1 *Homo sapiens* cDNA clone PLACE1009595 3', mRNA sequence. |
| BE867789 | Hs.110675 | PVRL2 | poliovirus receptor-related 2 (herpesvirus entry mediator B) |
| AA526844 | Hs.556600 | MYLK | MSTP083 mRNA, complete cds |
| BF435438 | Hs.80720 | | Full length insert cDNA YH93B03 |
| NM_005231 | Hs.632133 | EMS1 | ems1 sequence (mammary tumor and squamous cell carcinoma-associated (p80/85 src substrate) |
| NM_007150 | Hs.16622 | ZNF185 | zinc finger protein 185 (LIM domain) |
| NM_001928 | Hs.155597 | DF | D component of complement (adipsin) |
| NM_003831 | Hs.445511 | RIOK3 | RIO kinase 3 (yeast) |
| NM_022763 | Hs.159430 | FAD104 | FAD104 |
| NM_001343 | Hs.481980 | DAB2 | disabled homolog 2, mitogen-responsive phosphoprotein (*Drosophila*) |
| NM_020152 | Hs.222802 | C21orf7 | chromosome 21 open reading frame 7 |
| BC029493 | Hs.369265 | IRAK3 | interleukin-1 receptor-associated kinase 3 |
| BF976693 | Hs.376675 | | CDNA FLJ34100 fis, clone FCBBF3007597 |
| NM_000945 | Hs.280604 | PPP3R1 | protein phosphatase 3 (formerly 2B), regulatory subunit B, 19 kDa, alpha isoform (calcineurin B, type I) |
| AI215106 | Hs.591381 | INSR | insulin receptor |
| AI817801 | Hs.191356 | BIRC1 | Transcribed sequence with strong similarity to protein sp: Q13075 (*H. sapiens*) BIR1_HUMAN Baculoviral IAP repeat-containing protein 1 |
| AW270105 | Hs.643902 | RNF3 | ring finger protein 3 |
| BG913589 | Hs.59214 | LOC144871 | DnaJ (Hsp40) homolog, subfamily C, member 3 |
| W73230 | Hs.200100 | Ells1 | zd56c09.s1 Soares_fetal_heart_NbHH19W *Homo sapiens* cDNA clone IMAGE: 344656 3' similar to contains element MER10 repetitive element;, mRNA sequence. |
| BF691447 | Hs.644051 | B4GALT5 | UDP-Gal: betaGlcNAc beta 1,4-galactosyltransferase, polypeptide 5 |
| NM_005502 | Hs.429294 | ABCA1 | ATP-binding cassette, sub-family A (ABC1), member 1 |
| NM_000361 | Hs.2030 | THBD | thrombomodulin |
| AK024569 | Hs.195403 | DOCK5 | dedicator of cytokinesis 5 |
| AB051833 | Hs.123239 | ACRBP | acrosin binding protein |
| NM_004126 | Hs.83381 | GNG11 | guanine nucleotide binding protein (G protein), gamma 11 |
| Y07846 | Hs.322852 | GAS2L1 | growth arrest-specific 2 like 1 |
| BE327727 | Hs.443301 | | Transcribed sequences |
| M36532 | Hs.155097 | CA2 | catbonic anhydrase II |
| NM_017526 | Hs.23581 | OBRGRP | leptin receptor |
| AW205122 | Hs.496572 | FLJ22679 | hypothetical protein FLJ22679 |
| AI141116 | Hs.123239 | ACRBP | acrosin binding protein |
| AW293296 | Hs.163893 | | Transcribed sequences |
| N63244 | Hs.592143 | TUBB1 | tubulin, beta 1 |
| BG120535 | | VNN1 | 602346858F1 NIH_MGC_90 *Homo sapiens* cDNA clone IMAGE: 4441695 5', mRNA sequence. |
| AU152763 | Hs.586165 | | CDNA FLJ10742 fis, clone NT2RP3001629 |
| BC003064 | Hs.481980 | DAB2 | disabled homolog 2, mitogen-responsive phosphoprotein (*Drosophila*) |
| N63920 | Hs.596025 | | CDNA clone IMAGE: 5294823, partial cds |
| BG251467 | Hs.122514 | MSCP | mitochondrial solute carrier protein |
| AF237762 | Hs.306199 | GPR84 | G protein-coupled receptor 84 |
| AW206560 | Hs.609146 | | Transcribed sequences |
| AI971212 | Hs.434494 | SYNJ2 | synaptojanin 2 |
| AL136805 | Hs.278436 | ZNF537 | zinc finger protein 537 |
| BC026299 | Hs.518727 | | Clone IMAGE: 4275461, mRNA |
| BE675324 | Hs.200770 | | Transcribed sequences |
| NM_021647 | Hs.178121 | KIAA0626 | |
| NM_018482 | Hs.106015 | DDEF1 | synonyms: PAP, PAG2, ASAP1, ZG14P, KIAA1249; *Homo sapiens* development and differentiation enhancing factor 1 (DDEF1), mRNA. |
| AA149644 | Hs.150718 | JAM3 | junctional adhesion molecule 3 |
| AF325460 | Hs.351812 | CLECSF7 | C-type (calcium dependent, carbohydrate-recognition domain) lectin, superfamily member 7 |
| AW665656 | Hs.633892 | GLUL | glutamate-ammonia ligase (glutamine synthase) |
| AA417099 | Hs.465709 | | Transcribed sequences |
| NM_003897 | Hs.591785 | IER3 | immediate early response 3 |
| AF275260 | Hs.592117 | CXCL16 | chemokine (C-X-C motif) ligand 16 |
| AF001540 | | MALAT-1 | PRO1073 protein |
| AI640434 | Hs.601545 | FLJ10357 | hypothetical protein FLJ10357 |
| AW043859 | Hs.235795 | | Clone IMAGE: 5263020, mRNA |
| H68759 | Hs.122514 | | Transcribed sequences |
| NM_004536 | Hs.191356 | BIRC1 | baculoviral IAP repeat-containing 1 |
| AF086010 | Hs.335205 | | Full length insert cDNA clone YW04H08 |
| NM_003189 | Hs.73828 | TAL1 | T-cell acute lymphocytic leukemia 1 |
| AW138767 | Hs.274256 | ELOVL7 | hypothetical protein FL123563 |

TABLE 5-continued

| GenBank ID | Unigene ID | Common Name | Gene Description |
|---|---|---|---|
| NM_003693 | Hs.534497 | SCARF1 | scavenger receptor class F, member 1 |
| BG177759 | Hs.497873 | WDR26 | WD repeat domain 26 |
| AW264036 | Hs.478588 | BCL6 | B-cell CLL/lymphoma 6 (zinc finger protein 51) |
| AL119957 | Hs.59214 | DNAJC3 | DnaJ (Hsp40) homolog, subfamily C, member 3 |
| NM_018388 | Hs.105134 | MBNL3 | muscleblind-like 3 (*Drosophila*) |
| AI640434 | Hs.601545 | FLJ10357 | hypothetical protein FLJ10357 |
| AI332764 | Hs.516646 | | Transcribed sequences |
| AI719730 | Hs.24258 | GUCY1A3 | guanylate cyclase 1, soluble, alpha 3 |
| NM_130441 | Hs.351812 | CLECSF7 | C-type (calcium dependent, carbohydrate-recognition domain) lectin, superfamily member 7 |
| AW796364 | Hs.371594 | MKNK1 | Transcribed sequence with weak similarity to protein ref: NP_060265.1 (*H. sapiens*) hypothetical protein FLJ20378 [*Homo sapiens*] |
| BC043380 | Hs.468274 | | CDNA clone IMAGE: 5223469, partial cds |
| NM_017698 | | FLJ22679 | |
| AW069181 | Hs.603149 | ZAK | cr43e01.x1 Human bone marrow stromal cells *Homo sapiens* cDNA clone HBMSC_cr43e01 3', mRNA sequence. |
| AF350881 | Hs.272225 | TRPM6 | transient receptor potential cation channel, subfamily M, member 6 |
| AA082707 | Hs.592262 | MLL5 | myeloid/lymphoid or mixed-lineage leukemia 5 (trithorax homolog, *Drosophila*) |
| AL035700 | | SH3BGRL2 | continued from bA177G23.1 in Em: AL451064 match: proteins: Tr: O75368 Sw: P55822 Tr: Q9BPY5 Tr: Q9BRB8 Sw: Q9WUZ7; Human DNA sequence from clone RP1-75K24 on chromosome 6q13-15 Contains the the 3' end of the SH3BGRL2 gene for SH3 domain binding glutamic acid-rich protein-like 2, complete sequence. |
| N66571 | Hs.501898 | MRVI1 | murine retrovirus integration site 1 homolog |
| AA482548 | Hs.497873 | WDR26 | zt34b03.s1 Soares ovary tumor NbHOT *Homo sapiens* cDNA clone IMAGE: 724205 3', mRNA sequence. |
| AI052659 | Hs.334019 | | Transcribed sequences |
| AF074331 | | PAPSS2 | *Homo sapiens* PAPS synthetase-2 (PAPSS2) mRNA, complete cds. |
| AI682905 | Hs.280342 | PRKAR1A | protein kinase, cAMP-dependent, regulatory, type I, alpha (tissue specific extinguisher 1) |
| AI022066 | Hs.480763 | | Transcribed sequences |
| AI953847 | Hs.148741 | IBRDC2 | IBR domain containing 2 |
| NM_000361 | Hs.2030 | THBD | thrombomodulin |
| AY151286 | Hs.196384 | PTGS2 | prostaglandin-endoperoxide synthase 2 (prostaglandin G/H synthase and cyclooxygenase) |
| AL713724 | Hs.487994 | | MRNA; cDNA DKFZp667O0416 (from clone DKFZp667O0416) |
| AI831952 | Hs.567518 | NDE1 | nudE nuclear distribution gene E homolog 1 (*A. nidulans*) |
| N45231 | Hs.513053 | DNAJA4 | DnaJ (Hsp40) homolog, subfamily A, member 4 |
| AA044825 | Hs.520757 | TBXAS1 | thromboxane A synthase 1 (platelet, cytochrome P450, family 5, subfamily A) |
| AI476341 | Hs.93825 | | CDNA FLJ39784 fis, clone SPLEN2002314 |
| BF195718 | Hs.221889 | CSDA | cold shock domain protein A |
| AL833423 | Hs.379548 | | MRNA; cDNADKFZp313H2139 (from clone DKFZp313H2139) |
| NM_009590 | Hs.143102 | AOC2 | amine oxidase, copper containing 2 (retina-specific) |
| AA770170 | Hs.499489 | MIR | c-mir, cellular modulator of immune recognition |
| BE965029 | Hs.501928 | MICAL2 | 601658812R1 NIH_MGC_69 *Homo sapiens* cDNA clone IMAGE: 3886131 3', mRNA sequence. |
| BC018042 | Hs.279815 | CSAD | cysteine sulfinic acid decarboxylase |
| AA218974 | | LOC158563 | zr02g12.s1 Stratagene NT2 neuronal precursor 937230 *Homo sapiens* cDNA clone IMAGE: 650374 3', mRNA sequence. |
| AF188298 | Hs.481980 | DAB2 | disabled homolog 2, mitogen-responsive phosphoprotein (*Drosophila*) |
| NM_005906 | Hs.446125 | MAK | male germ cell-associated kinase |
| BC002716 | Hs.496572 | FLJ22679 | hypothetical protein FLJ22679 |
| AK023512 | Hs.463439 | SPAG9 | sperm associated antigen 9 |
| AA010315 | Hs.60371 | | Transcribed sequences |
| AF051151 | Hs.135853 | TLR5 | toll-like receptor 5 |
| BU929456 | | OSTF1 | AGENCOURT_10424238 NIH_MGC_79 *Homo sapiens* cDNA clone IMAGE: 6663343 5', mRNA sequence. |
| NM_002607 | Hs.535898 | PDGFA | platelet-derived growth factor alpha polypeptide |
| AK024748 | Hs.297343 | CAMKK2 | calcium/calmodulin-dependent protein kinase kinase 2, beta |
| U76248 | Hs.477959 | SIAH2 | seven in absentia homolog 2 (*Drosophila*) |
| AI819198 | Hs.208229 | GPR54 | G protein-coupled receptor 54 |
| AI452469 | Hs.605187 | | Transcribed sequence with weak similarity to protein ref: NP_009032.1 (*H. sapiens*) sarcosine dehydrogenase; dimethylglycine dehydrogenase-like 1 [*Homo sapiens*] |
| AA037483 | Hs.458395 | HIST1H2BC | zk34a02.s1 Soares_pregnant_uterus_NbHPU *Homo sapiens* cDNA clone IMAGE: 484682 3', mRNA sequence. |
| U56237 | Hs.631534 | FCAR | Fc fragment of IgA, receptor for |
| N66045 | Hs.29189 | | Transcribed sequences |
| AW299958 | Hs.524491 | PAPSS2 | 3'-phosphoadenosine 5'-phosphosulfate synthase 2 |
| AK021983 | Hs.106015 | | CDNA FLJ11921 fis, clone HEMBB1000318 |
| NM_002398 | Hs.526754 | MEIS1 | Meis1, myeloid ecotropic viral integration site 1 homolog (mouse) |
| AV725666 | Hs.220950 | FOXO3A | CDNA clone IMAGE: 4814010, partial cds |
| AK026714 | Hs.7886 | PELI1 | pellino homolog 1 (*Drosophila*) |
| NM_005373 | Hs.82906 | MPL | CDC20 cell division cycle 20 homolog (*S. cerevisiae*) |
| AK024382 | | | unnamed protein product; *Homo sapiens* cDNA FLJ14320 fis, clone PLACE3000455. |
| AA702409 | Hs.592017 | | Transcribed sequences |
| AI074467 | Hs.593643 | | Transcribed sequences |
| AI368358 | Hs.496969 | NPL | N-acetylneuraminate pyruvate lyase (dihydrodipicolinate synthase) |

TABLE 5-continued

| GenBank ID | Unigene ID | Common Name | Gene Description |
|---|---|---|---|
| H28667 | Hs.444451 | ZAK | sterile alpha motif and leucine zipper containing kinase AZK |
| AL544951 | Hs.280604 | PPP3R1 | AL544951 *Homo sapiens* PLACENTA COT 25-NORMALIZED *Homo sapiens* cDNA clone CS0DI012YC11 5-PRIME, mRNA sequence. |
| AL050388 | Hs.487046 | SOD2 | superoxide dismutase 2, mitochondrial |
| AI829674 | Hs.584845 | | Transcribed sequences |
| NM_018324 | Hs.24309 | THEDC1 | hypothetical protein FLJ11106 |
| AA362254 | Hs.529633 | | Transcribed sequences |
| AW130600 | Hs.99472 | | MRNA; cDNA DKFZp564O0862 (from clone DKFZp564O0862) |
| N25732 | Hs.591328 | FOXO3A | yx83c03.s1 Soares melanocyte 2NbHM *Homo sapiens* cDNA clone IMAGE: 268324 3', mRNA sequence. |
| NM_017815 | Hs.442782 | C14orf94 | chromosome 14 open reading frame 94 |
| AK055448 | | ZNF587 | *Homo sapiens* cDNA FLJ30886 fis, clone FEBRA2005014, weakly similar to ZINC FINGER PROTEIN 84. |
| S69189 | Hs.464137 | ACOX1 | acyl-Coenzyme A oxidase 1, palmitoyl |
| AU146027 | Hs.592326 | | AU146027 HEMBA1 *Homo sapiens* cDNA clone HEMBA1006595 3', mRNA sequence. |
| BE439987 | Hs.462214 | GAS7 | growth arrest-specific 7 |
| AI363213 | Hs.381058 | KIAA0146 | KIAA0146 protein |
| BF508786 | Hs.613959 | | MRNA; cDNA DKFZp686J24234 (from clone DKFZp686J24234) |
| BF680284 | Hs.34558 | | CDNA: FLJ21199 fis, clone COL00235 |
| H93077 | Hs.519694 | C5orf4 | chromosome 5 open reading frame 4 |
| AI798924 | Hs.191850 | | Transcribed sequences |
| W19983 | Hs.370725 | OSBPL1A | oxysterol binding protein-like 1A |
| AA057437 | Hs.458747 | | Transcribed sequences |
| NM_024565 | Hs.14070 | FLJ14166 | hypothetical protein FLJ14166 |
| AI356228 | Hs.515351 | KIAA1533 | KIAA1533 |
| AI937121 | Hs.29282 | | Transcribed sequences |
| AI806045 | Hs.61438 | | Transcribed sequences |
| N24643 | Hs.446017 | WSB1 | WD repeat and SOCS box-containing 1 |
| AU122258 | | | AU122258 MAMMA1 *Homo sapiens* cDNA clone MAMMA1002009 5', mRNA sequence. |
| AI278204 | Hs.99472 | | MRNA; cDNA DKFZp564O0862 (from clone DKFZp564O0862) |
| AW450374 | Hs.593734 | | Clone IMAGE: 4824518, mRNA |
| BE888885 | Hs.220950 | FOXO3A | CDNA clone IMAGE: 4814010, partial cds |
| AK023845 | | USP34 | ubiquitin specific protease 34 |
| BF511336 | Hs.591641 | | Transcribed sequences |
| R12665 | Hs.11594 | | CDNA FLJ27273 fis, clone TMS00761 |
| BC006428 | Hs.189119 | CXXC5 | CXXC finger 5 |
| AI354636 | Hs.586401 | | qu95c03.x1 NCI_CGAP_Gas4 *Homo sapiens* cDNA clone IMAGE: 1979812 3', mRNA sequence. |
| AK025248 | Hs.546419 | FLJ13220 | hypothetical protein FLJ13220 |
| BE675549 | Hs.79170 | TTC9 | tetratricopeptide repeat domain 9 |
| NM_000579 | Hs.450802 | CCR5 | chemokine (C-C motif) receptor 5 |
| AB020630 | Hs.45719 | PPP1R16B | protein phosphatase 1, regulatory (inhibitor) subunit 16B |
| NM_002985 | Hs.514821 | CCL5 | chemokine (C-C motif) ligand 5 |
| NM_014392 | Hs.518595 | D4S234E | DNA segment on chromosome 4 (unique) 234 expressed sequence |
| AI821566 | Hs.642748 | TTC16 | torsin family 2, member A |
| AA771779 | Hs.461074 | ZFP90 | zinc finger protein 90 homolog (mouse) |
| AI084226 | Hs.58831 | TOSO | regulator of Fas-induced apoptosis |
| AF057557 | Hs.58831 | TOSO | regulator of Fas-induced apoptosis |
| NM_005356 | Hs.470627 | LCK | lymphocyte-specific protein tyrosine kinase |
| BC041468 | Hs.434746 | LOC339988 | Hypothetical protein LOC339988 (LOC339988), mRNA |
| BC002556 | | RAB3IP | |
| NM_002002 | Hs.465778 | FCER2 | Fc fragment of IgE, low affinity II, receptor for (CD23A) |
| NM_018556 | Hs.590883 | SIRPB2 | signal-regulatory protein beta 2 |
| AB020630 | Hs.45719 | PPP1R16B | protein phosphatase 1, regulatory (inhibitor) subunit 16B |
| AF298547 | Hs.369279 | NALP2 | NACHT, leucine rich repeat and PYD containing 2 |
| AW157571 | Hs.479066 | MARLIN1 | multiple coiled-coil GABABR1-binding protein |
| AA767131 | Hs.121432 | KIAA0073 | KIAA0073 protein |
| M21121 | Hs.514821 | CCL5 | chemokine (C-C motif) ligand 5 |
| NM_004356 | Hs.54457 | CD81 | CD81 antigen (target of antiproliferative antibody 1) |
| BF432238 | Hs.585799 | ZNF286 | CDNA FLJ31089 fis, clone IMR321000092 |
| NM_004310 | Hs.160673 | RHOH | ras homolog gene family, member H |
| BC000533 | Hs.567374 | EIF3S8 | eukaryotic translation initiation factor 3, subunit 8, 110 kDa |
| U07236 | Hs.470627 | LCK | lymphocyte-specific protein tyrosine kinase |
| AI702465 | Hs.23606 | | Transcribed sequences |
| AU155091 | Hs.633678 | | Clone IMAGE: 4814008, mRNA |
| U90339 | Hs.584739 | ADK | adenosine kinase |
| AW575245 | Hs.266331 | FREB | Fc receptor homolog expressed in B cells |
| NM_030915 | Hs.567598 | LBH | likely ortholog of mouse limb-bud and heart gene |
| AI524095 | Hs.403857 | LY9 | lymphocyte antigen 9 |
| AW204712 | Hs.385493 | C10orf128 | hypothetical protein LOC170371 |
| U49396 | Hs.408615 | P2RX5 | purinergic receptor P2X, ligand-gated ion channel, 5 |
| AA781795 | Hs.546467 | EPSTI1 | epithelial stromal interaction 1 (breast) |
| BF433219 | | | Transcribed sequences |
| BC003574 | Hs.2484 | TCL1A | T-cell leukemia/lymphoma 1A |
| AB051458 | Hs.419171 | KIAA1671 | KIAA1671 protein |
| NM_004114 | Hs.6540 | FGF13 | fibroblast growth factor 13 |

TABLE 5-continued

| GenBank ID | Unigene ID | Common Name | Gene Description |
|---|---|---|---|
| BF446578 | Hs.125293 | RASGEF1A | RasGEF domain family, member 1A |
| AA931562 | Hs.444049 | | Transcribed sequence with weak similarity to protein ref: NP_060312.1 (*H. sapiens*) hypothetical protein FLJ20489 [*Homo sapiens*] |
| BF514552 | Hs.292449 | FCRH3 | Fc receptor-like protein 3 |
| X82240 | Hs.2484 | TCL1A | T-cell leukemia/lymphoma 1A |
| AW296309 | Hs.405667 | CD8B1 | CD8 antigen, beta polypeptide 1 (p37) |
| M85256 | Hs.554197 | IGKC | Isolate donor Z clone Z55K immunoglobulin kappa light chain variable region mRNA, partial cds |
| AF439512 | Hs.387787 | KLRK1 | killer cell lectin-like receptor subfamily K, member 1 |
| NM_005442 | Hs.591663 | EOMES | eomesodermin homolog (*Xenopus laevis*) |
| AI424825 | Hs.435052 | ATP8A1 | ATPase, aminophospholipid transporter (APLT), Class I, type 8A, member 1 |
| NM_006159 | Hs.505326 | NELL2 | NEL-like 2 (chicken) |
| BI547087 | | | 603190322F1 NIH_MGC_95 *Homo sapiens* cDNA clone IMAGE: 5261717 5', mRNA sequence. |
| BC001872 | Hs.510635 | IGHM | synonym: MU; *Homo sapiens* immunoglobulin heavy constant mu, mRNA (cDNA clone MGC: 1228 IMAGE: 3544448), complete cds. |
| AW006735 | Hs.85258 | CD8A | CD8 antigen, alpha polypeptide (p32) |
| NM_007360 | Hs.387787 | KLRK1 | killer cell lectin-like receptor subfamily K, member 1 |
| NM_002261 | Hs.74082 | KLRC3 | synonyms: NKG2E, NKG2-E: isoform NKG2-E is encoded by transcript variant NKG2-E; go_component: integral to membrane [goid 0016021] [evidence IEA]; go_function; transmembrane receptor activity [goid 0004888] [evidence TAS] [pmid 9683661]; go_function; lectin [goid 0005530] [evidence IEA]; go_function; sugar binding [goid 0005529] [evidence IEA]; go_process; cellular defense response [goid 0006968] [evidence TAS] [pmid 9683661]; go_process; heterophilic cell adhesion [goid 0007157] [evidence IEA]; *Homo sapiens* killer cell lectin-like receptor subfamily C, member 3 (KLRC-3), transcript variant NKG2-E, mRNA. |
| M13231 | Hs.534032 | TRGV9 | T cell receptor gamma locus |
| AI753792 | Hs.502004 | RRAS2 | related RAS viral (r-ras) oncogene homolog 2 |
| M16768 | Hs.534032 | TRGV9 | T-cell receptor (V-J-C) precursor; Human T-cell receptor gamma chain VJCI-CII-CIII region mRNA, complete cds. |
| NM_003175 | Hs.458346 | XCL1 | chemokine (C motif) ligand 2 |
| U96394 | Hs.449601 | IGL@ | Clone P2-147 anti-oxidized LDL immunoglobulin light chain Fab mRNA, partial cds |
| M27331 | Hs.534032 | TRGV9 | T cell receptor gamma locus |
| U23772 | Hs.546295 | XCL1 | chemokine (C motif) ligand 1 |
| NM_004931 | Hs.405667 | CD8B1 | CD8 antigen, beta polypeptide 1 (p37) |
| NM_006275 | Hs.6891 | SFRS6 | splicing factor, arginine/serine-rich 6 |
| BC020552 | Hs.379186 | PDCD6 | programmed cell death 6 |
| NM_001548 | Hs.20315 | IFIT1 | interferon-induced protein with tetratricopeptide repeats 1 |
| BC005248 | Hs.461178 | EIF1AY | eukaryotic translation initiation factor 1A, Y-linked |
| NM_004660 | Hs.99120 | DDX3Y | DEAD (Asp-Glu-Ala-Asp) box polypeptide 3, Y-linked |
| NM_001008 | Hs.282376 | RPS4Y1 | ribosomal protein S4, Y-linked |

TABLE 6

| GenBank ID | Unigene ID | Common Name | Gene Description |
|---|---|---|---|
| AA167449 | Hs.529901 | XIST | MRNA; cDNA DKFZp686K10163 (from clone DKFZp686K10163) |
| AV646597 | Hs.529901 | | MRNA; cDNA DKFZp686K10163 (from clone DKFZp686K10163) |
| NM_000607 | Hs.567311 | ORM1 | orosomucoid 1 |
| BE644917 | Hs.529901 | XIST | MRNA; cDNA DKFZp686K10163 (from clone DKFZp686K10163) |
| AA628440 | Hs.529901 | XIST | MRNA; cDNA DKFZp686K10163 (from clone DKFZp686K10163) |
| AI733564 | Hs.478588 | | Transcribed sequence with weak similarity to protein pir: A40138 (*H. sapiens*) A40138 glycogen phosphorylase |
| NM_000419 | Hs.411312 | ITGA2B | integrin, alpha 2b (platelet glycoprotein IIb of IIb/IIIa complex, antigen CD41B) |
| BE867789 | Hs.110675 | PVRL2 | poliovirus receptor-related 2 (herpesvirus entry mediator B) |
| AA551086 | Hs.99691 | LAK | lymphocyte alpha-kinase |
| AB023212 | Hs.158722 | PCNX | pecanex homolog (*Drosophila*) |
| AL109714 | Hs.459049 | LOC283687 | hypothetical protein LOC283687 |
| L10343 | | PI3 | elafin has been sequenced at the protein level; pre-elafin has not; its existence is assumed from its molecular weight (PAGE analysis); putative; *Homo sapiens* elafin precursor, gene, complete cds. |
| AW167424 | Hs.585653 | NUMB | numb homolog (*Drosophila*) |
| M35999 | Hs.218040 | ITGB3 | integrin, beta 3 (platelet glycoprotein IIIa, antigen CD61) |
| NM_002638 | Hs.112341 | PI3 | protease inhibitor 3, skin-derived (SKALP) |
| AI929792 | Hs.21374 | | Transcribed sequences |
| NM_000607 | Hs.567311 | ORM2 | orosomucoid 1 |
| R64130 | Hs.2164 | PPBP | pro-platelet basic protein (chemokine (C-X-C motif) ligand 7) |
| NM_003118 | Hs.111779 | SPARC | secreted protein, acidic, cysteine-rich (osteonectin) |
| NM_002736 | Hs.433068 | PRKAR2B | protein kinase, cAMP-dependent, regulatory, type II, beta |
| AA703239 | Hs.159430 | | Transcribed sequence with weak similarity to protein prf: 1303335A (*H. sapiens*) 1303335A decay accelerating factor long [*Homo sapiens*] |
| NM_004666 | Hs.12114 | VNN1 | vanin 1 |
| NM_016348 | Hs.519694 | C5orf4 | chromosome 5 open reading frame 4 |
| BI868572 | | DKFZp686I15217 | 603392679F1 NIH_MGC_90 *Homo sapiens* cDNA clone IMAGE: 5402706 5', mRNA sequence. |

TABLE 6-continued

| GenBank ID | Unigene ID | Common Name | Gene Description |
| --- | --- | --- | --- |
| AW205418 | Hs.495097 | KIAA2025 | KIAA2025 protein |
| NM_001999 | Hs.519294 | FBN2 | fibrillin 2 (congenital contractural arachnodactyly) |
| AI520949 | Hs.110675 | PVRL2 | poliovirus receptor-related 2 (herpesvirus entry mediator B) |
| M25915 | Hs.436657 | CLU | clusterin (complement lysis inhibitor, SP-40, 40, sulfated glycoprotein 2, testosterone-repressed prostate message 2, apolipoprotein J) |
| BF055462 | Hs.164226 | THBS1 | thrombospondin 1 |
| AI679555 | Hs.527653 | | Transcribed sequence with weak similarity to protein ref: NP_060312.1 (*H. sapiens*) hypothetical protein FLJ20489 [*Homo sapiens*] |
| AW051321 | Hs.464137 | | CDNA FLJ30303 fis, clone BRACE2003269 |
| NM_000129 | Hs.335513 | F13A1 | coagulation factor XIII, A1 polypeptide |
| BE896490 | Hs.595327 | SNAP29 | synaptosomal-associated protein, 29 kDa |
| NM_000697 | Hs.422967 | ALOX12 | arachidonate 12-lipoxygenase |
| AA181060 | Hs.349283 | | Clone IMAGE: 5288883, mRNA |
| NM_002619 | Hs.81564 | PF4 | platelet factor 4 (chemokine (C-X-C motif) ligand 4) |
| AU157823 | | PYGL | AU157823 PLACE1 Homo sapiens cDNA clone PLACE1009595 3', mRNA sequence. |
| BE867789 | Hs.110675 | PVRL2 | poliovirus receptor-related 2 (herpesvirus entry mediator B) |
| AA526844 | Hs.556600 | MYLK | MSTP083 mRNA, complete cds |
| BF435438 | Hs.80720 | | Full length insert cDNA YH93B03 |
| NM_005231 | Hs.632133 | EMS1 | ems1 sequence (mammary tumor and squamous cell carcinoma-associated (p80/85 src substrate) |
| NM_007150 | Hs.16622 | ZNF185 | zinc finger protein 185 (LIM domain) |
| NM_001928 | Hs.155597 | DF | D component of complement (adipsin) |
| NM_003831 | Hs.445511 | RIOK3 | RIO kinase 3 (yeast) |
| NM_022763 | Hs.159430 | FAD104 | FAD104 |
| NM_001343 | Hs.481980 | DAB2 | disabled homolog 2, mitogen-responsive phosphoprotein (*Drosophila*) |
| NM_020152 | Hs.222802 | C21orf7 | chromosome 21 open reading frame 7 |
| BC029493 | Hs.369265 | IRAK3 | interleukin-1 receptor-associated kinase 3 |
| BF976693 | Hs.376675 | | CDNA FLJ34100 fis, clone FCBBF3007597 |
| NM_000945 | Hs.280604 | PPP3R1 | protein phosphatase 3 (formerly 2B), regulatory subunit B, 19 kDa, alpha isoform (calcineurin B, type I) |
| AI215106 | Hs.591381 | INSR | insulin receptor |
| AI817801 | Hs.191356 | BIRC1 | Transcribed sequence with strong similarity to protein sp: Q13075 (*H. sapiens*) BIR1_HUMAN Baculoviral IAP repeat-containing protein 1 |
| AW270105 | Hs.643902 | RNF3 | ring finger protein 3 |
| BG913589 | Hs.59214 | LOC144871 | DnaJ (Hsp40) homolog, subfamily C, member 3 |
| W73230 | Hs.200100 | Ells1 | zd56c09.s1 Soares_fetal_heart_NbHH19W Homo sapiens cDNA clone IMAGE: 344656 3' similar to contains element MER10 repetitive element;, mRNA sequence. |
| BF691447 | Hs.644051 | B4GALT5 | UDP-Gal: betaGlcNAc beta 1,4-galactosyltransferase, polypeptide 5 |
| NM_005502 | Hs.429294 | ABCA1 | ATP-binding cassette, sub-family A (ABC1), member 1 |
| NM_000361 | Hs.2030 | THBD | thrombomodulin |
| AK024569 | Hs.195403 | DOCK5 | dedicator of cytokinesis 5 |
| AB051833 | Hs.123239 | ACRBP | acrosin binding protein |
| NM_004126 | Hs.83381 | GNG11 | guanine nucleotide binding protein (G protein), gamma 11 |
| Y07846 | Hs.322852 | GAS2L1 | growth arrest-specific 2 like 1 |
| BE327727 | Hs.443301 | | Transcribed sequences |
| M36532 | Hs.155097 | CA2 | carbonic anhydrase II |
| NM_017526 | Hs.23581 | OBRGRP | leptin receptor |
| AW205122 | Hs.496572 | FLJ22679 | hypothetical protein FLJ22679 |
| AI141116 | Hs.123239 | ACRBP | acrosin binding protein |
| AW293296 | Hs.163893 | | Transcribed sequences |
| N63244 | Hs.592143 | TUBB1 | tubulin, beta 1 |
| BG120535 | | VNN1 | 602346858F1 NIH_MGC_90 Homo sapiens cDNA clone IMAGE: 4441695 5', mRNA sequence. |
| AU152763 | Hs.586165 | | CDNA FLJ10742 fis, clone NT2RP3001629 |
| BC003064 | Hs.481980 | DAB2 | disabled homolog 2, mitogen-responsive phosphoprotein (*Drosophila*) |
| N63920 | Hs.596025 | | CDNA clone IMAGE: 5294823, partial cds |
| BG251467 | Hs.122514 | MSCP | mitochondrial solute carrier protein |
| AF237762 | Hs.306199 | GPR84 | G protein-coupled receptor 84 |
| AW206560 | Hs.609146 | | Transcribed sequences |
| AI971212 | Hs.434494 | SYNJ2 | synaptojanin 2 |
| AL136805 | Hs.278436 | ZNF537 | zinc finger protein 537 |
| BC026299 | Hs.518727 | | Clone IMAGE: 4275461, mRNA |
| BE675324 | Hs.200770 | | Transcribed sequences |
| NM_021647 | Hs.178121 | KIAA0626 | |
| NM_018482 | Hs.106015 | DDEF1 | synonyms: PAP, PAG2, ASAP1, ZG14P, KIAA1249; *Homo sapiens* development and differentiation enhancing factor 1 (DDEF1), mRNA. |
| AA149644 | Hs.150718 | JAM3 | junctional adhesion molecule 3 |
| AF325460 | Hs.351812 | CLECSF7 | C-type (calcium dependent, carbohydrate-recognition domain) lectin, superfamily member 7 |
| AW665656 | Hs.633892 | GLUL | glutamate-ammonia ligase (glutamine synthase) |
| AA417099 | Hs.465709 | | Transcribed sequences |
| NM_003897 | Hs.591785 | IER3 | immediate early response 3 |
| AF275260 | Hs.592117 | CXCL16 | chemokine (C-X-C motif) ligand 16 |
| AF001540 | | MALAT-1 | PRO1073 protein |
| AI640434 | Hs.601545 | FLJ10357 | hypothetical protein FLJ10357 |
| AW043859 | Hs.235795 | | Clone IMAGE: 5263020, mRNA |

TABLE 6-continued

| GenBank ID | Unigene ID | Common Name | Gene Description |
|---|---|---|---|
| H68759 | Hs.122514 | | Transcribed sequences |
| NM_004536 | Hs.191356 | BIRC1 | baculoviral IAP repeat-containing 1 |
| AF086010 | Hs.335205 | | Full length insert cDNA clone YW04H08 |
| NM_003189 | Hs.73828 | TAL1 | T-cell acute lymphocytic leukemia 1 |
| AW138767 | Hs.274256 | ELOVL7 | hypothetical protein FLJ23563 |
| NM_003693 | Hs.534497 | SCARF1 | scavenger receptor class F, member 1 |
| BG177759 | Hs.497873 | WDR26 | WD repeat domain 26 |
| AW264036 | Hs.478588 | BCL6 | B-cell CLL/lymphoma 6 (zinc finger protein 51) |
| AL119957 | Hs.59214 | DNAJC3 | DnaJ (Hsp40) homolog, subfamily C, member 3 |
| NM_018388 | Hs.105134 | MBNL3 | muscleblind-like 3 (*Drosophila*) |
| AI640434 | Hs.601545 | FLJ10357 | hypothetical protein FLJ10357 |
| AI332764 | Hs.516646 | | Transcribed sequences |
| AI719730 | Hs.24258 | GUCY1A3 | guanylate cyclase 1, soluble, alpha 3 |
| NM_130441 | Hs.351812 | CLECSF7 | C-type (calcium dependent, carbohydrate-recognition domain) lectin, superfamily member 7 |
| AW796364 | Hs.371594 | MKNK1 | Transcribed sequence with weak similarity to protein ref: NP_060265.1 (*H. sapiens*) hypothetical protein FLJ20378 [*Homo sapiens*] |
| BC043380 | Hs.468274 | | cDNA clone IMAGE: 5223469, partial cds |
| NM_017698 | | FLJ22679 | |
| AW069181 | Hs.603149 | ZAK | cr43e01.x1 Human bone marrow stromal cells *Homo sapiens* cDNA clone HBMSC_cr43e01 3', mRNA sequence. |
| AF350881 | Hs.272225 | TRPM6 | transient receptor potential cation channel, subfamily M, member 6 |
| AA082707 | Hs.592262 | MLL5 | myeloid/lymphoid or mixed-lineage leukemia 5 (trithorax homolog, *Drosophila*) |
| AL035700 | | SH3BGRL2 | continued from bA177G23.1 in Em: AL451064 match: proteins: Tr: O75368 Sw: P55822 Tr: Q9BPY5 Tr: Q9BRB8 Sw: Q9WUZ7; Human DNA sequence from clone RP1-75K24 on chromosome 6q13-15 Contains the the 3' end of the SH3BGRL2 gene for SH3 domain binding glutamic acid-rich protein-like 2, complete sequence. |
| N66571 | Hs.501898 | MRVI1 | murine retrovirus integration site 1 homolog |
| AA482548 | Hs.497873 | WDR26 | zt34b03.s1 Soares ovary tumor NbHOT *Homo sapiens* cDNA clone IMAGE: 724205 3', mRNA sequence. |
| AI052659 | Hs.334019 | | Transcribed sequences |
| AF074331 | | PAPSS2 | *Homo sapiens* PAPS synthetase-2 (PAPSS2) mRNA, complete cds. |
| AI682905 | Hs.280342 | PRKAR1A | protein kinase, cAMP-dependent, regulatory, type I, alpha (tissue specific extinguisher 1) |
| AI022066 | Hs.480763 | | Transcribed sequences |
| AI953847 | Hs.148741 | IBRDC2 | IBR domain containing 2 |
| NM_000361 | Hs.2030 | THBD | thrombomodulin |
| AY151286 | Hs.196384 | PTGS2 | prostaglandin-endoperoxide synthase 2 (prostaglandin G/H synthase and cyclooxygenase) |
| AL713724 | Hs.487994 | | MRNA; cDNA DKFZp667O0416 (from clone DKFZp667O0416) |
| AI831952 | Hs.567518 | NDE1 | nudE nuclear distribution gene E homolog 1 (*A. nidulans*) |
| N45231 | Hs.513053 | DNAJA4 | DnaJ (Hsp40) homolog, subfamily A, member 4 |
| AA044825 | Hs.520757 | TBXAS1 | thromboxane A synthase 1 (platelet, cytochrome P450, family 5, subfamily A) |
| AI476341 | Hs.93825 | | CDNA FLJ39784 fis, clone SPLEN2002314 |
| BF195718 | Hs.221889 | CSDA | cold shock domain protein A |
| AL833423 | Hs.379548 | | MRNA; cDNADKFZp313H2139 (from cloneDKFZp313H2139) |
| NM_009590 | Hs.143102 | AOC2 | amine oxidase, copper containing 2 (retina-specific) |
| AA770170 | Hs.499489 | MIR | c-mir, cellular modulator of immune recognition |
| BE965029 | Hs.501928 | MICAL2 | 601658812R1 NIH_MGC_69 *Homo sapiens* cDNA clone IMAGE: 3886131 3', mRNA sequence. |
| BC018042 | Hs.279815 | CSAD | cysteine sulfinic acid decarboxylase |
| AA218974 | | LOC158563 | zr02g12.s1 Stratagene NT2 neuronal precursor 937230 *Homo sapiens* cDNA clone IMAGE: 650374 3', mRNA sequence. |
| AF188298 | Hs.481980 | DAB2 | disabled homolog 2, mitogen-responsive phosphoprotein (*Drosophila*) |
| NM_005906 | Hs.446125 | MAK | male germ cell-associated kinase |
| BC002716 | Hs.496572 | FLJ22679 | hypothetical protein FLJ22679 |
| AK023512 | Hs.463439 | SPAG9 | sperm associated antigen 9 |
| AA010315 | Hs.60371 | | Transcribed sequences |
| AF051151 | Hs.135853 | TLR5 | toll-like receptor 5 |
| BU929456 | | OSTF1 | AGENCOURT_10424238 NIH_MGC_79 *Homo sapiens* cDNA clone IMAGE: 6663343 5', mRNA sequence. |
| NM_002607 | Hs.535898 | PDGFA | platelet-derived growth factor alpha polypeptide |
| AK024748 | Hs.297343 | CAMKK2 | calcium/calmodulin-dependent protein kinase kinase 2, beta |
| U76248 | Hs.477959 | SIAH2 | seven in absentia homolog 2 (*Drosophila*) |
| AI819198 | Hs.208229 | GPR54 | G protein-coupled receptor 54 |
| AI452469 | Hs.605187 | | Transcribed sequence with weak similarity to protein ref: NP_009032.1 (*H. sapiens*) sarcosine dehydrogenase; dimethylglycine dehydrogenase-like 1 [*Homo sapiens*] |
| AA037483 | Hs.458395 | HIST1H2BC | zk34a02.s1 Soares_pregnant_uterus_NbHPU *Homo sapiens* cDNA clone IMAGE: 484682 3', mRNA sequence. |
| U56237 | Hs.631534 | FCAR | Fc fragment of IgA, receptor for |
| N66045 | Hs.29189 | | Transcribed sequences |
| AW299958 | Hs.524491 | PAPSS2 | 3'-phosphoadenosine 5'-phosphosulfate synthase 2 |
| AK021983 | Hs.106015 | | CDNA FLJ11921 fis, clone HEMBB1000318 |
| NM_002398 | Hs.526754 | MEIS1 | Meis1, myeloid ecotropic viral integration site 1 homolog (mouse) |
| AV725666 | Hs.220950 | FOXO3A | CDNA clone IMAGE: 4814010, partial cds |
| AK026714 | Hs.7886 | PELI1 | pellino homolog 1 (*Drosophila*) |
| NM_005373 | Hs.82906 | MPL | CDC20 cell division cycle 20 homolog (*S. cerevisiae*) |

TABLE 6-continued

| GenBank ID | Unigene ID | Common Name | Gene Description |
|---|---|---|---|
| AK024382 | | | unnamed protein product; *Homo sapiens* cDNA FLJ14320 fis, clone PLACE3000455. |
| AA702409 | Hs.592017 | | Transcribed sequences |
| AI074467 | Hs.593643 | | Transcribed sequences |
| AI368358 | Hs.496969 | NPL | N-acetylneuraminate pyruvate lyase (dihydrodipicolinate synthase) |
| H28667 | Hs.444451 | ZAK | sterile alpha motif and leucine zipper containing kinase AZK |
| AL544951 | Hs.280604 | PPP3R1 | AL544951 *Homo sapiens* PLACENTA COT 25-NORMALIZED *Homo sapiens* cDNA clone CS0DI012YC11 5-PRIME, mRNA sequence. |
| AL050388 | Hs.487046 | SOD2 | superoxide dismutase 2, mitochondrial |
| AI829674 | Hs.584845 | | Transcribed sequences |
| NM_018324 | Hs.24309 | THEDC1 | hypothetical protein FLJ11106 |
| AA362254 | Hs.529633 | | Transcribed sequences |
| AW130600 | Hs.99472 | | MRNA; cDNA DKFZp564O0862 (from clone DKFZp564O0862) |
| N25732 | Hs.591328 | FOXO3A | yx83c03.s1 Soares melanocyte 2NbHM *Homo sapiens* cDNA clone IMAGE: 268324 3', mRNA sequence. |
| NM_017815 | Hs.442782 | C14orf94 | chromosome 14 open reading frame 94 |
| AK055448 | | ZNF587 | *Homo sapiens* cDNA FLJ30886 fis, clone FEBRA2005014, weakly similar to ZINC FINGER PROTEIN 84. |
| S69189 | Hs.464137 | ACOX1 | acyl-Coenzyme A oxidase 1, palmitoyl |
| AU146027 | Hs.592326 | | AU146027 HEMBA1 *Homo sapiens* cDNA clone HEMBA1006595 3', mRNA sequence. |
| BE439987 | Hs.462214 | GAS7 | growth arrest-specific 7 |
| AI363213 | Hs.381058 | KIAA0146 | KIAA0146 protein |
| BF508786 | Hs.613959 | | MRNA; cDNA DKFZp686J24234 (from clone DKFZp686J24234) |
| BF680284 | Hs.34558 | | CDNA: FLJ21199 fis, clone COL00235 |
| H93077 | Hs.519694 | C5orf4 | chromosome 5 open reading frame 4 |
| AI798924 | Hs.191850 | | Transcribed sequences |
| W19983 | Hs.370725 | OSBPL1A | oxysterol binding protein-like 1A |
| AA057437 | Hs.458747 | | Transcribed sequences |
| NM_024565 | Hs.14070 | FLJ14166 | hypothetical protein FLJ14166 |
| AI356228 | Hs.515351 | KIAA1533 | KIAA1533 |
| AI937121 | Hs.29282 | | Transcribed sequences |
| AI806045 | Hs.61438 | | Transcribed sequences |
| N24643 | Hs.446017 | WSB1 | WD repeat and SOCS box-containing 1 |
| AU122258 | | | AU122258 MAMMA1 *Homo sapiens* cDNA clone MAMMA1002009 5', mRNA sequence. |
| AI278204 | Hs.99472 | | MRNA; cDNA DKFZp564O0862 (from clone DKFZp564O0862) |
| AW450374 | Hs.593734 | | Clone IMAGE: 4824518, mRNA |
| BE888885 | Hs.220950 | FOXO3A | CDNA clone IMAGE: 4814010, partial cds |
| AK023845 | | USP34 | ubiquitin specific protease 34 |
| BF511336 | Hs.591641 | | Transcribed sequences |
| NM_007199 | Hs.369265 | IRAK3 | interleukin-1 receptor-associated kinase 3 |
| AI056872 | Hs.591328 | | Transcribed sequences |
| BG251467 | Hs.122514 | MSCP | mitochondrial solute carrier protein |
| NM_022083 | | C1orf24 | chromosome 1 open reading frame 24 |
| AW057518 | Hs.608694 | ELL2 | elongation factor, RNA polymerase II, 2 |
| AI650285 | Hs.287299 | | Transcribed sequence with weak similarity to protein ref: NP_060312.1 (*H. sapiens*) hypothetical protein FLJ20489 [*Homo sapiens*] |
| AU147506 | Hs.7886 | PELI1 | pellino homolog 1 (*Drosophila*) |
| BF435852 | Hs.464137 | ACOX1 | acyl-Coenzyme A oxidase 1, palmitoyl |
| W03103 | Hs.106015 | DDEF1 | za04b05.r1 Soares melanocyte 2NbHM *Homo sapiens* cDNA clone IMAGE: 291537 5', mRNA sequence. |
| AI458949 | Hs.520414 | IFNGR1 | interferon gamma receptor 1 |
| AB030034 | Hs.444451 | ZAK | sterile alpha motif and leucine zipper containing kinase AZK |
| BC011877 | Hs.195403 | DOCK5 | Hypothetical protein LOC286061 (LOC286061), mRNA |
| AL137028 | | | |
| NM_007219 | Hs.589884 | RNF24 | ring finger protein 24 |
| AA868809 | Hs.25447 | | CDNA FLJ43180 fis, clone FCBBF3013846 |
| NM_012329 | Hs.463483 | MMD | monocyte to macrophage differentiation-associated |
| AA778783 | Hs.420024 | | Transcribed sequence with weak similarity to protein ref: NP_055301.1 (*H. sapiens*) neuronal thread protein [*Homo sapiens*] |
| NM_030918 | Hs.192326 | SNX27 | sorting nexin family member 27 |
| T79640 | Hs.174312 | | Transcribed sequences |
| R91734 | | | yp98f04.r1 Soares fetal liver spleen 1NFLS *Homo sapiens* cDNA clone IMAGE: 195487 5', mRNA sequence. |
| U44403 | Hs.75367 | SLA | Src-like-adaptor |
| BF591270 | Hs.595473 | KLHL8 | 7h44e04.x1 NCI_CGAP_Col6 *Homo sapiens* cDNA clone IMAGE: 3318846 3', mRNA sequence. |
| BC042590 | Hs.434241 | LOC404636 | *Homo sapiens* cDNA clone IMAGE: 4821044, partial cds. |
| NM_018586 | | MSCP | |
| BE221883 | Hs.11184 | UBE2R2 | ubiquitin-conjugating enzyme E2R 2 |
| BG337478 | Hs.128037 | | CDNA FLJ38117 fis, clone D3OST2003797 |
| AV723666 | | EFCBP2 | AV723666 HTB *Homo sapiens* cDNA clone HTBABA11 5', mRNA sequence. |
| AK025898 | Hs.525232 | LRP10 | low density lipoprotein receptor-related protein 10 |
| AB062477 | | | *Homo sapiens* OK/SW-cl.41 mRNA, complete cds. |
| AW467357 | Hs.371720 | SYK | spleen tyrosine kinase |
| AI808120 | Hs.479766 | RRM1 | TPA regulated locus |
| BE966748 | | ERO1L | 601661247R1 NIH_MGC_72 *Homo sapiens* cDNA clone IMAGE: 3916235 3', mRNA sequence. |

TABLE 6-continued

| GenBank ID | Unigene ID | Common Name | Gene Description |
|---|---|---|---|
| AK024677 | Hs.632602 | ASAHL | N-acylsphingosine amidohydrolase (acid ceramidase)-like |
| AL038191 | Hs.474536 | | DKFZp566P1724_s1 566 (synonym: hfkd2) *Homo sapiens* cDNA clone DKFZp566P1724 3', mRNA sequence. |
| BG432887 | Hs.442789 | | Transcribed sequence with weak similarity to protein ref: NP_005210.1 (*H. sapiens*) diaphanous 1; Diaphanous, *Drosophila*, homolog of, 1; deafness, autosomal dominant 1; diaphanous |
| BF516252 | Hs.528703 | ANKRD13 | ankyrin repeat domain 13 |
| AA576497 | Hs.492740 | ATF6 | activating transcription factor 6 |
| NM_017593 | Hs.146551 | BMP2K | BMP2 inducible kinase |
| NM_003105 | Hs.368592 | SORL1 | sortilin-related receptor, L(DLR class) A repeats-containing |
| AA706922 | Hs.517034 | | Transcribed sequences |
| AI963142 | Hs.48353 | | CDNA FLJ32274 fis, clone PROST2000036 |
| AI735391 | Hs.146551 | BMP2K | at10e09.x1 Barstead aorta HPLRB6 *Homo sapiens* cDNA clone IMAGE: 2354728 3', mRNA sequence. |
| AI807658 | Hs.192326 | | Transcribed sequences |
| BE693389 | | | Transcribed sequences |
| N32832 | Hs.159430 | FAD104 | FAD104 |
| AF015452 | Hs.390736 | CFLAR | CASP8 and FADD-like apoptosis regulator |
| AL049273 | Hs.429434 | | MRNA; cDNA DKFZp564H023 (from clone DKFZp564H023) |
| BC039388 | Hs.237886 | | Clone IMAGE: 5298774, mRNA |
| AA382004 | Hs.122514 | MSCP | EST95296 Activated T-cells II *Homo sapiens* cDNA 5' end, mRNA sequence. |
| BG334495 | Hs.631749 | LOC284021 | hypothetical protein LOC284021 |
| AW367571 | Hs.438673 | LOC338692 | hypothetical protein LOC338692 |
| AI084056 | Hs.464217 | PGS1 | phosphatidylglycerophosphate synthase |
| AK054840 | Hs.106015 | | CDNA FLJ30278 fis, clone BRACE2002755 |
| AI051950 | Hs.99472 | | MRNA; cDNA DKFZp564O862 (from clone DKFZp564O862) |
| BF724303 | Hs.412293 | | Transcribed sequences |
| AK000794 | Hs.520757 | | CDNA FLJ20787 fis, clone COL02178 |
| AF153820 | Hs.1547 | KCNJ2 | potassium inwardly-rectifying channel, subfamily J, member 2 |
| BE671084 | Hs.293593 | ARHGAP26 | GTPase regulator associated with focal adhesion kinase pp125(FAK) |
| AU146685 | Hs.126667 | | CDNA FLJ11971 fis, clone HEMBB1001208 |
| AI962978 | Hs.469244 | WASF2 | WAS protein family, member 2 |
| AI634046 | Hs.390736 | CFLAR | CASP8 and FADD-like apoptosis regulator |
| AW297879 | Hs.436271 | | Transcribed sequences |
| AK025534 | Hs.588289 | | CDNA: FLJ21881 fis, clone HEP02746 |
| N72610 | Hs.484363 | | Transcribed sequence with strong similarity to protein pdb: 1BGM (*E. coli*) O Chain O, Beta-Galactosidase |
| BF056507 | Hs.372000 | NSMAF | neutral sphingomyelinase (N-SMase) activation associated factor |
| W87434 | Hs.106015 | | Transcribed sequence with moderate similarity to protein sp: P39188 (*H. sapiens*) ALU1_HUMAN Alu subfamily J sequence contamination warning entry |
| AF085978 | Hs.474596 | | *Homo sapiens* full length insert cDNA clone YT87E05. |
| N63821 | Hs.175437 | DKFZp434C184 | za26c12.s1 Soares fetal liver spleen 1NFLS *Homo sapiens* cDNA clone IMAGE: 293686 3', mRNA sequence. |
| AV700891 | Hs.517296 | | v-ets erythroblastosis virus E26 oncogene homolog 2 (avian) |
| AI692401 | Hs.29282 | | Transcribed sequences |
| N52625 | Hs.603141 | ZRANB1 | yv37f12.s1 Soares fetal liver spleen 1NFLS *Homo sapiens* cDNA clone IMAGE: 244943 3' similar to contains element MER22 repetitive element;, mRNA sequence. |
| R45471 | Hs.479396 | RBPSUH | recombining binding protein suppressor of hairless (*Drosophila*) |
| H67156 | Hs.122514 | | Transcribed sequences |
| BF724558 | Hs.636976 | | Transcribed sequence with moderate similarity to protein pir: T02670 (*H. sapiens*) T02670 probable thromboxane A2 receptor isoform beta - human |
| BE551054 | Hs.279583 | DREV1 | DORA reverse strand protein 1 |
| NM_021213 | Hs.285218 | PCTP | phosphatidylcholine transfer protein |
| N93399 | Hs.494406 | LOC349236 | CDNA FLJ46484 fis, clone THYMU3026350 |
| BF668314 | Hs.221497 | PRO0149 | PRO0149 protein |
| NM_002213 | Hs.536663 | ITGB5 | integrin, beta 5 |
| AW974609 | Hs.136398 | ZCCHC6 | zinc finger, CCHC domain containing 6 |
| AK001393 | Hs.134857 | MGC12458 | hypothetical protein MGC12458 |
| NM_000313 | Hs.64016 | PROS1 | protein S (alpha) |
| AW027474 | Hs.446678 | NCOA2 | nuclear receptor coactivator 2 |
| AI422414 | Hs.484551 | | Transcribed sequences |
| NM_004196 | Hs.280881 | CDKL1 | cyclin-dependent kinase-like 1 (CDC2-related kinase) |
| AI374686 | Hs.122523 | | Transcribed sequences |
| AW184034 | Hs.600998 | BRAF | v-raf murine sarcoma viral oncogene homolog B1 |
| BC025707 | Hs.484099 | KCNMB1 | potassium large conductance calcium-activated channel, subfamily M, beta member 1 |
| AA815354 | Hs.520684 | | Hypothetical LOC284527 (LOC284527), mRNA |
| AF306674 | Hs.132050 | MGC40368 | hypothetical protein MGC40368 |
| W93728 | Hs.77890 | GUCY1B3 | guanylate cyclase 1, soluble, beta 3 |
| NM_003326 | Hs.181097 | TNFSF4 | tumor necrosis factor (ligand) superfamily, member 4 (tax-transcriptionally activated glycoprotein 1, 34 kDa) |
| R62432 | Hs.211252 | SLC24A3 | solute carrier family 24 (sodium/potassium/calcium exchanger), member 3 |
| AI821895 | Hs.433060 | | Transcribed sequences |
| AW051591 | Hs.388364 | LOC285533 | hypothetical protein LOC285533 |
| NM_000187 | Hs.368254 | HGD | homogentisate 1,2-dioxygenase (homogentisate oxidase) |
| AK023837 | Hs.159799 | THRAP2 | thyroid hormone receptor associated protein 2 |
| BF446281 | Hs.433307 | BCKDHA | branched chain keto acid dehydrogenase E1, alpha polypeptide (maple syrup urine disease) |

TABLE 6-continued

| GenBank ID | Unigene ID | Common Name | Gene Description |
|---|---|---|---|
| BE046521 | Hs.191482 | CUTL1 | cut-like 1, CCAAT displacement protein (*Drosophila*) |
| AW006409 | Hs.532144 | | histone 1, H3d |
| AI476341 | Hs.93825 | | CDNA FLJ39784 fis, clone SPLEN2002314 |
| BF512068 | Hs.575090 | | Transcribed sequences |
| AA488687 | Hs.390594 | SLC7A11 | solute carrier family 7, (cationic amino acid transporter, y+ system) member 11 |
| NM_002413 | Hs.81874 | MGST2 | microsomal glutathione S-transferase 2 |
| R64696 | | CD58 | yi22f12.r1 Soares placenta Nb2HP *Homo sapiens* cDNA clone IMAGE: 140015 5' similar to contains Alu repetitive element;, mRNA sequence. |
| AV699911 | Hs.310421 | | Transcribed sequence with weak similarity to protein sp: P23961 (*H. sapiens*) ALUC_HUMAN !!!! ALU CLASS C WARNING ENTRY !!!! |
| NM_002350 | Hs.491767 | LYN | v-yes-1 Yamaguchi sarcoma viral related oncogene homolog |
| AI698731 | Hs.202238 | | Transcribed sequences |
| AA215519 | | | zr97a07.r1 NCI_CGAP_GCB1 *Homo sapiens* cDNA clone IMAGE: 683604 5', mRNA sequence. |
| BC000195 | Hs.279583 | DREV1 | DORA reverse strand protein 1 |
| AW304786 | Hs.507260 | SLC15A4 | solute carrier family 15, member 4 |
| AA705029 | Hs.529488 | | Transcribed sequence with strong similarity to protein pdb: 1BGM (*E. coli*) O Chain O, Beta-Galactosidase |
| BC020868 | Hs.632256 | STAT5B | signal transducer and activator of transcription 5B |
| BM849515 | Hs.636486 | LRRK1 | leucine-rich repeat kinase 1 |
| AW269743 | Hs.254477 | | CDNA FLJ20182 fis, clone COLF0190 |
| BC039825 | Hs.446125 | MAK | male germ cell-associated kinase |
| NM_014339 | Hs.129751 | IL17R | interleukin 17 receptor |
| AW196696 | Hs.484363 | | Transcribed sequence with strong similarity to protein ref: NP_060904.1 (*H. sapiens*) goliath protein; likely ortholog of mouse g1-related zinc finger protein [*Homo sapiens*] |
| AI583964 | Hs.544636 | | Transcribed sequences |
| BE552138 | Hs.632488 | CR1 | complement component (3b/4b) receptor 1-like |
| AI738802 | Hs.644106 | CDK11 | cyclin-dependent kinase (CDC2-like) 11 |
| BC025708 | Hs.592017 | FLJ11175 | hypothetical protein FLJ11175 |
| BE327650 | Hs.369978 | FLJ11753 | hypothetical protein FLJ11753 |
| AI972498 | Hs.97469 | a1/3GTP | Clone IMAGE: 4812754, mRNA |
| AI668625 | Hs.380094 | | Full length insert cDNA YO61D09 |
| AI342132 | Hs.485241 | | qt26c08.x1 Soares_pregnant_uterus_NbHPU *Homo sapiens* cDNA clone IMAGE: 1949102 3', mRNA sequence. |
| AF350251 | Hs.132868 | USP32 | ubiquitin specific protease 32 |
| BC038707 | Hs.420559 | | *Homo sapiens*, Similar to neuronal thread protein, clone IMAGE: 3932744, mRNA. |
| AK022004 | Hs.106015 | | CDNA FLJ11942 fis, clone HEMBB1000652 |
| BF512846 | Hs.471461 | ACSL3 | acyl-CoA synthetase long-chain family member 3 |
| NM_014450 | Hs.88012 | SIT | SHP2-interacting transmembrane adaptor protein |
| BF345244 | Hs.378501 | LOC283989 | hypothetical protein LOC283989 |
| AI057637 | Hs.234898 | LOC283445 | acetyl-Coenzyme A carboxylase beta |
| BC002918 | Hs.213088 | CHST12 | carbohydrate (chondroitin 4) sulfotransferase 12 |
| X79782 | Hs.449601 | IGLJ3 | *H. sapiens* (T1.1) mRNA for IG lambda light chain |
| NM_024310 | Hs.466383 | PLEKHF1 | pleckstrin homology domain containing, family F (with FYVE domain) member 1 |
| BF116060 | Hs.519783 | FLJ44216 | FLJ44216 protein |
| Y11339 | Hs.105352 | SIAT7A | sialyltransferase 7 ((alpha-N-acetylneuraminyl-2,3-beta-galactosyl-1,3)-N-acetyl galactosaminide alpha-2,6-sialyltransferase) A |
| BC003379 | Hs.632714 | LOC57228 | hypothetical protein from clone 643 |
| NM_024947 | Hs.529592 | PHC3 | polyhomeotic like 3 (*Drosophila*) |
| NM_000878 | Hs.474787 | IL2RB | interleukin 2 receptor, beta |
| AF031138 | Hs.509513 | NCR3 | natural cytotoxicity triggering receptor 3 |
| NM_014914 | Hs.435039 | CENTG2 | centaurin, gamma 2 |
| NM_030978 | Hs.132499 | ARPC5L | actin related protein 2/3 complex, subunit 5-like |
| NM_004758 | Hs.112499 | BZRAP1 | benzodiazapine receptor (peripheral) associated protein 1 |
| AW338214 | Hs.437696 | | Clone IMAGE: 5275753, mRNA |
| AJ238374 | | TH1L | *Homo sapiens* mRNA for putative protein TH1, partial, clone IMAGE ID 785447. |
| AF288573 | Hs.2007 | TNFSF6 | tumor necrosis factor (ligand) superfamily, member 6 |
| NM_031213 | Hs.465542 | C19orf27 | hypothetical protein MGC5244 |
| AF044954 | Hs.513266 | NDUFB10 | NADH dehydrogenase (ubiquinone) 1 beta subcomplex, 10, 22 kDa |
| BE671663 | Hs.592102 | EVER2 | epidermodysplasia verruciformis 2 |
| NM_007237 | Hs.632549 | SP140 | SP140 nuclear body protein |
| AI003777 | Hs.632176 | 1-Sep | septin 1 |
| AI421559 | Hs.106185 | RALGDS | ral guanine nucleotide dissociation stimulator |
| NM_020886 | Hs.503891 | USP28 | ubiquitin specific protease 28 |
| AI042377 | Hs.470457 | | Transcribed sequences |
| AA742584 | Hs.125914 | C8orf5 | chromosome 8 open reading frame 5 |
| BG231773 | Hs.371680 | | CDNA FLJ46579 fis, clone THYMU3042758 |
| BE788984 | | GALM | 601481076F1 NIH_MGC_68 *Homo sapiens* cDNA clone IMAGE: 3883818 5', mRNA sequence. |
| AA135722 | Hs.597962 | | Transcribed sequences |
| NM_014349 | Hs.474737 | APOL3 | apolipoprotein L, 3 |
| AW268594 | Hs.374421 | C9orf81 | chromosome 9 open reading frame 81 |
| NM_018641 | Hs.213088 | CHST12 | carbohydrate (chondroitin 4) sulfotransferase 12 |
| BF678830 | | LOC152485 | hypothetical protein LOC152485 |
| NM_006117 | Hs.15250 | PECI | peroxisomal D3,D2-enoyl-CoA isomerase |
| AW977516 | Hs.592755 | | Transcribed sequences |

TABLE 6-continued

| GenBank ID | Unigene ID | Common Name | Gene Description |
|---|---|---|---|
| BF984830 | Hs.190284 | RAI1 | retinoic acid induced 1 |
| NM_005263 | Hs.73172 | GFI1 | growth factor independent 1 |
| AI347139 | Hs.8162 | MGC39372 | hypothetical protein MGC39372 |
| NM_002832 | Hs.402773 | PTPN7 | protein tyrosine phosphatase, non-receptor type 7 |
| NM_003362 | Hs.191334 | UNG | uracil-DNA glycosylase |
| AA679705 | Hs.535464 | EIF3S8 | eukaryotic translation initiation factor 3, subunit 8, 110 kDa |
| AY007128 | Hs.469728 | | CDNA FLJ26726 fis, clone PRS02774 |
| AK074465 | Hs.462833 | FLJ31952 | hypothetical protein FLJ31952 |
| NM_001504 | Hs.198252 | CXCR3 | chemokine (C-X-C motif) receptor 3 |
| NM_005715 | Hs.557541 | UST | uronyl-2-sulfotransferase |
| AA683481 | Hs.22546 | MGC20446 | hypothetical protein MGC20446 |
| AI829961 | Hs.36972 | CD7 | CD7 antigen (p41) |
| AI609285 | Hs.503891 | USP28 | tw83h09.x1 NCI_CGAP_HN5 Homo sapiens cDNA clone IMAGE: 2266337 3' similar to contains Alu repetitive element; contains element MER29 repetitive element;, mRNA sequence. |
| AL582804 | Hs.403857 | LY9 | lymphocyte antigen 9 |
| NM_000107 | Hs.643521 | DDB2 | damage-specific DNA binding protein 2, 48 kDa |
| AL833685 | Hs.440508 | | MRNA; cDNA DKFZp667O0522 (from clone DKFZp667O0522) |
| BE568184 | | 15E1.2 | cytochrome c oxidase subunit VIa polypeptide 1 |
| BG250907 | Hs.591503 | | Clone IMAGE: 5178133, mRNA |
| NM_018281 | Hs.476319 | FLJ10948 | hypothetical protein FLJ10948 |
| BG542955 | Hs.133916 | LOC152485 | hypothetical protein LOC152485 |
| AK024386 | Hs.155742 | GRHPR | glyoxylate reductase/hydroxypyruvate reductase |
| NM_024070 | Hs.521075 | STAG3 | stromal antigen 3 |
| AB014719 | Hs.618112 | APBA2 | amyloid beta (A4) precursor protein-binding, family A, member 2 (X11-like) |
| D42043 | Hs.98910 | RAFTLIN | raft-linking protein |
| AY043466 | Hs.292449 | FCRH3 | Fc receptor-like protein 3 |
| AI017564 | Hs.492716 | MGC21654 | unknown MGC21654 product |
| NM_005317 | Hs.465511 | GZMM | granzyme M (lymphocyte met-ase 1) |
| AL527430 | Hs.2006 | GSTM3 | glutathione S-transferase M3 (brain) |
| NM_014767 | Hs.523009 | SPOCK2 | synonym: testican-2: go_component: extracellular matrix [goid 0005578] [evidence NAS] [pmid 10386950]; go_function: calcium ion binding [goid 0005509] [evidence IDA] [pmid 10386950]; go_process; synaptogenesis [goid 0007416] [evidence NAS] lpmid 10386950]; go_process; extracellular matrix organization and biogenesis [goid 0030198] [evidence NAS] [pmid 10386950]; go_process; regulation of cell differentiation [goid 0045595] [evidence NAS] [pmid 10386950]; Homo sapiens sparc/osteonectin, cwcv and kazal-like domains proteoglycan (testican) 2 (SPOCK2), mRNA. |
| BC040914 | Hs.322462 | | Clone IMAGE: 5745627, mRNA |
| AK001164 | Hs.599785 | | CDNA FLJ10302 fis, clone NT2RM2000042 |
| AK097515 | Hs.120250 | FLJ40597 | hypothetical protein FLJ40597 |
| NM_005608 | Hs.155975 | PTPRCAP | protein tyrosine phosphatase, receptor type, C-associated protein |
| AI457120 | Hs.331420 | PPAT | phosphoribosyl pyrophosphate amidotransferase |
| AA541630 | Hs.170019 | RUNX3 | runt-related transcription factor 3 |
| NM_024709 | Hs.519839 | FLJ14146 | hypothetical protein FLJ14146 |
| NM_013330 | Hs.642710 | NME7 | non-metastatic cells 7, protein expressed in (nucleoside-diphosphate kinase) |
| AL520200 | Hs.420796 | MGC15429 | hypothetical protein MGC15429 |
| NM_003752 | Hs.567374 | EIF3S8 | eukaryotic translation initiation factor 3, subunit 8, 110 kDa |
| BE259729 | Hs.438429 | RPS19 | ribosomal protein S19 |
| AW043830 | Hs.471441 | | Transcribed sequences |
| R12665 | Hs.11594 | | CDNA FLJ27273 fis, clone TMS00761 |
| BC006428 | Hs.189119 | CXXC5 | CXXC finger 5 |
| AI354636 | Hs.586401 | | qu95c03.x1 NCI_CGAP_Gas4 Homo sapiens cDNA clone IMAGE: 1979812 3', mRNA sequence. |
| AK025248 | Hs.546419 | FLJ13220 | hypothetical protein FLJ13220 |
| BE675549 | Hs.79170 | TTC9 | tetratricopeptide repeat domain 9 |
| NM_000579 | Hs.450802 | CCR5 | chemokine (C-C motif) receptor 5 |
| AB020630 | Hs.45719 | PPP1R16B | protein phosphatase 1, regulatory (inhibitor) subunit 16B |
| NM_002985 | Hs.514821 | CCL5 | chemokine (C-C motif) ligand 5 |
| NM_014392 | Hs.518595 | D4S234E | DNA segment on chromosome 4 (unique) 234 expressed sequence |
| AI821566 | Hs.642748 | TTC16 | torsin family 2, member A |
| AA771779 | Hs.461074 | ZFP90 | zinc finger protein 90 homolog (mouse) |
| AI084226 | Hs.58831 | TOSO | regulator of Fas-induced apoptosis |
| AF057557 | Hs.58831 | TOSO | regulator of Fas-induced apoptosis |
| NM_005356 | Hs.470627 | LCK | lymphocyte-specific protein tyrosine kinase |
| BC041468 | Hs.434746 | LOC339988 | Hypothetical protein LOC339988 (LOC339988), mRNA |
| BC002556 | | RAB3IP | |
| NM_002002 | Hs.465778 | FCER2 | Fc fragment of IgE, low affinity II, receptor for (CD23A) |
| NM_018556 | Hs.590883 | SIRPB2 | signal-regulatory protein beta 2 |
| AB020630 | Hs.45719 | PPP1R16B | protein phosphatase 1, regulatory (inhibitor) subunit 16B |
| AF298547 | Hs.369279 | NALP2 | NACHT, leucine rich repeat and PYD containing 2 |
| AW157571 | Hs.479066 | MARLIN1 | multiple coiled-coil GABABR1-binding protein |
| AA767131 | Hs.121432 | KIAA0073 | KIAA0073 protein |
| M21121 | Hs.514821 | CCL5 | chemokine (C-C motif) ligand 5 |
| NM_004356 | Hs.54457 | CD81 | CD81 antigen (target of antiproliferative antibody 1) |
| BF432238 | Hs.585799 | ZNF286 | CDNA FLJ31089 fis, clone IMR321000092 |
| NM_004310 | Hs.160673 | RHOH | ras homolog gene family, member H |
| BC000533 | Hs.567374 | EIF3S8 | eukaryotic translation initiation factor 3, subunit 8, 110 kDa |

TABLE 6-continued

| GenBank ID | Unigene ID | Common Name | Gene Description |
|---|---|---|---|
| U07236 | Hs.470627 | LCK | lymphocyte-specific protein tyrosine kinase |
| AI702465 | Hs.23606 | | Transcribed sequences |
| AU155091 | Hs.633678 | | Clone IMAGE: 4814008, mRNA |
| U90339 | Hs.584739 | ADK | adenosine kinase |
| AW575245 | Hs.266331 | FREB | Fc receptor homolog expressed in B cells |
| NM_030915 | Hs.567598 | LBH | likely ortholog of mouse limb-bud and heart gene |
| AI524095 | Hs.403857 | LY9 | lymphocyte antigen 9 |
| AW204712 | Hs.385493 | C10orf128 | hypothetical protein LOC170371 |
| U49396 | Hs.408615 | P2RX5 | purinergic receptor P2X, ligand-gated ion channel, 5 |
| AA781795 | Hs.546467 | EPSTI1 | epithelial stromal interaction 1 (breast) |
| BF433219 | | | Transcribed sequences |
| BC003574 | Hs.2484 | TCL1A | T-cell leukemia/lymphoma 1A |
| AB051458 | Hs.419171 | KIAA1671 | KIAA1671 protein |
| NM_004114 | Hs.6540 | FGF13 | fibroblast growth factor 13 |
| BF446578 | Hs.125293 | RASGEF1A | RasGEF domain family, member 1A |
| AA931562 | Hs.444049 | | Transcribed sequence with weak similarity to protein ref: NP_060312.1 (*H. sapiens*) hypothetical protein FLJ20489 [*Homo sapiens*] |
| BF514552 | Hs.292449 | FCRH3 | Fc receptor-like protein 3 |
| X82240 | Hs.2484 | TCL1A | T-cell leukemia/lymphoma 1A |
| AW296309 | Hs.405667 | CD8B1 | CD8 antigen, beta polypeptide 1 (p37) |
| M85256 | Hs.554197 | IGKC | Isolate donor Z clone Z55K immunoglobulin kappa light chain variable region mRNA, partial cds |
| AF439512 | Hs.387787 | KLRK1 | killer cell lectin-like receptor subfamily K, member 1 |
| NM_005442 | Hs.591663 | EOMES | eomesodermin homolog (*Xenopus laevis*) |
| AI424825 | Hs.435052 | ATP8A1 | ATPase, aminophospholipid transporter (APLT), Class I, type 8A, member 1 |
| NM_006159 | Hs.505326 | NELL2 | NEL-like 2 (chicken) |
| BI547087 | | | 603190322F1 NIH_MGC_95 Homo sapiens cDNA clone IMAGE: 5261717 5', mRNA sequence. |
| BC001872 | Hs.510635 | IGHM | synonym: MU; *Homo sapiens* immunoglobulin heavy constant mu, mRNA (cDNA clone MGC: 1228 IMAGE: 3544448), complete cds. |
| AW006735 | Hs.85258 | CD8A | CD8 antigen, alpha polypeptide (p32) |
| NM_007360 | Hs.387787 | KLRK1 | killer cell lectin-like receptor subfamily K, member 1 |
| NM_002261 | Hs.74082 | KLRC3 | synonyms: NKG2E, NKG2-E; isoform NKG2-E is encoded by transcript variant NKG2-E; go_component: integral to membrane [goid 0016021] [evidence IEA]; go_function: transmembrane receptor activity [goid 0004888] [evidence TAS] [pmid 9683661]; go_function: lectin [goid 0005530] [evidence IEA]; go_function: sugar binding [goid 0005529] [evidence IEA]; go_process: cellular defense response [goid 0006968] [evidence TAS] [pmid 9683661]; go_process: heterophilic cell adhesion [goid 0007157] [evidence IEA]; *Homo sapiens* killer cell lectin-like receptor subfamily C, member 3 (KLRC3), transcript variant NKG2-E, mRNA. |
| M13231 | Hs.534032 | TRGV9 | T cell receptor gamma locus |
| AI753792 | Hs.502004 | RRAS2 | related RAS viral (r-ras) oncogene homolog 2 |
| M16768 | Hs.534032 | TRGV9 | T-cell receptor (V-J-C) precursor; Human T-cell receptor gamma chain VJCI-CII-CIII region mRNA, complete cds. |
| NM_003175 | Hs.458346 | XCL1 | chemokine (C motif) ligand 2 |
| U96394 | Hs.449601 | IGL1 | Clone P2-147 anti-oxidized LDL immunoglobulin light chain Fab mRNA, partial cds |
| M27331 | Hs.534032 | TRGV9 | T cell receptor gamma locus |
| U23772 | Hs.546295 | XCL1 | chemokine (C motif) ligand 1 |
| NM_004931 | Hs.405667 | CD8B1 | CD8 antigen, beta polypeptide 1 (p37) |
| NM_006275 | Hs.6891 | SFRS6 | splicing factor, arginine/serine-rich 6 |
| BC020552 | Hs.379186 | PDCD6 | programmed cell death 6 |
| NM_001548 | Hs.20315 | IFIT1 | interferon-induced protein with tetratricopeptide repeats 1 |
| BC005248 | Hs.461178 | EIF1AY | eukaryotic translation initiation factor 1A, Y-linked |
| NM_004660 | Hs.99120 | DDX3Y | DEAD (Asp-Glu-Ala-Asp) box polypeptide 3, Y-linked |
| NM_001008 | Hs.282376 | RPS4Y1 | ribosomal protein S4, Y-linked |

TABLE 7

| GenBank ID | Unigene ID | Gene Description |
|---|---|---|
| AA167449 | Hs.529901 | MRNA; cDNA DKFZp686K10163 (from clone DKFZp686K10163) |
| AV646597 | Hs.529901 | MRNA; cDNA DKFZp686K10163 (from clone DKFZp686K10163) |
| NM_000607 | Hs.567311 | orosomucoid 1 |
| BE644917 | Hs.529901 | MRNA; cDNA DKFZp686K10163 (from clone DKFZp686K10163) |
| AA628440 | Hs.529901 | MRNA; cDNA DKFZp686K10163 (from clone DKFZp686K10163) |
| AI733564 | Hs.478588 | Transcribed sequence with weak similarity to protein pir: A40138 (*H. sapiens*) A40138 glycogen phosphorylase |
| NM_000419 | Hs.411312 | "integrin, alpha 2b (platelet glycoprotein IIb of IIb/IIIa complex, antigen CD41B)" |
| BE867789 | Hs.110675 | poliovirus receptor-related 2 (herpesvirus entry mediator B) |
| AA521086 | Hs.99691 | lymphocyte alpha-kinase |
| AB023212 | Hs.158722 | pecanex homolog (*Drosophila*) |
| AL109714 | Hs.459049 | hypothetical protein LOC283687 |
| L10343 | | "elafin has been sequenced at the protein level; pre-elafin has not; its existence is assumed from its molecular weight (PAGE analysis); putative; *Homo sapiens* elafin precursor, gene, complete cds." |

TABLE 7-continued

| GenBank ID | Unigene ID | Gene Description |
|---|---|---|
| AW167424 | Hs.585653 | numb homolog (Drosophila) |
| M35999 | Hs.218040 | "integrin, beta 3 (platelet glycoprotein IIIa, antigen CD61)" |
| NM_002638 | Hs.112341 | "protease inhibitor 3, skin-derived (SKALP)" |
| AI929792 | Hs.21374 | Transcribed sequences |
| NM_000607 | Hs.567311 | orosomucoid 1 |
| R64130 | Hs.2164 | pro-platelet basic protein (chemokine (C-X-C motif) ligand 7) |
| NM_003118 | Hs.111779 | "secreted protein, acidic, cysteine-rich (osteonectin)" |
| NM_002736 | Hs.433068 | "protein kinase, cAMP-dependent, regulatory, type II, beta" |
| AA703239 | Hs.159430 | Transcribed sequence with weak similarity to protein prf: 1303335A (H. sapiens) 1303335A decay accelerating factor long [Homo sapiens] |
| NM_004666 | Hs.12114 | vanin 1 |
| NM_016348 | Hs.519694 | chromosome 5 open reading frame 4 |
| BI868572 | | "603392679F1 NIH_MGC_90 Homo sapiens cDNA clone IMAGE: 5402706 5', mRNA sequence." |
| AW205418 | Hs.495097 | KIAA2025 protein |
| NM_001999 | Hs.519294 | fibrillin 2 (congenital contractural arachnodactyly) |
| AI520949 | Hs.110675 | poliovirus receptor-related 2 (herpesvirus entry mediator B) |
| M25915 | Hs.436657 | "clusterin (complement lysis inhibitor, SP-40,40, sulfated glycoprotein 2, testosterone-repressed prostate message 2, apolipoprotein J)" |
| BF055462 | Hs.164226 | thrombospondin 1 |
| AI679555 | Hs.527653 | Transcribed sequence with weak similarity to protein ref: NP_060312.1 (H. sapiens) hypothetical protein FLJ20489 [Homo sapiens] |
| AW051321 | Hs.464137 | "CDNA FLJ30303 fis, clone BRACE2003269" |
| NM_000129 | Hs.335513 | "coagulation factor XIII, A1 polypeptide" |
| BE896490 | Hs.595327 | "synaptosomal-associated protein, 29 kDa" |
| NM_000697 | Hs.422967 | arachidonate 12-lipoxygenase |
| AA181060 | Hs.349283 | "Clone IMAGE: 5288883, mRNA" |
| NM_002619 | Hs.81564 | platelet factor 4 (chemokine (C-X-C motif) ligand 4) |
| AU157823 | | "AU157823 PLACE1 Homo sapiens cDNA clone PLACE1009595 3', mRNA sequence." |
| BE867789 | Hs.110675 | poliovirus receptor-related 2 (herpesvirus entry mediator B) |
| AA526844 | Hs.556600 | "MSTP083 mRNA, complete cds" |
| BF435438 | Hs.80720 | Full length insert cDNA YH93B03 |
| NM_005231 | Hs.632133 | ems1 sequence (mammary tumor and squamous cell carcinoma-associated (p80/85 src substrate) |
| NM_007150 | Hs.16622 | zinc finger protein 185 (LIM domain) |
| NM_001928 | Hs.155597 | D component of complement (adipsin) |
| NM_003831 | Hs.445511 | RIO kinase 3 (yeast) |
| NM_022763 | Hs.159430 | FAD 104 |
| NM_001343 | Hs.481980 | "disabled homolog 2, mitogen-responsive phosphoprotein (Drosophila)" |
| NM_020152 | Hs.222802 | chromosome 21 open reading frame 7 |
| BC029493 | Hs.369265 | interleukin-1 receptor-associated kinase 3 |
| BF976693 | Hs.376675 | "CDNA FLJ34100 fis, clone FCBBF3007597" |
| NM_000945 | Hs.280604 | "protein phosphatase 3 (formerly 2B), regulatory subunit B, 19 kDa, alpha isoform (calcineurin B, type I)" |
| AI215106 | Hs.591381 | insulin receptor |
| AI817801 | Hs.191356 | Transcribed sequence with strong similarity to protein sp: Q13075 (H. sapiens) BIR1_HUMAN Baculoviral IAP repeat-containing protein 1 |
| AW270105 | Hs.643902 | ring finger protein 3 |
| BG913589 | Hs.59214 | "DnaJ (Hsp40) homolog, subfamily C, member 3" |
| W73230 | Hs.200100 | "zd56c09.s1 Soares_fetal_heart_NbHH19W Homo sapiens cDNA clone IMAGE: 344656 3' similar to contains element MER10 repetitive element;, mRNA sequence." |
| BF691447 | Hs.644051 | "UDP-Gal: betaGlcNAc beta 1,4-galactosyltransferase, polypeptide 5" |
| NM_005502 | Hs.429294 | "ATP-binding cassette, sub-family A (ABC1), member 1" |
| NM_000361 | Hs.2030 | thrombomodulin |
| AK024569 | Hs.195403 | dedicator of cytokinesis 5 |
| AB051833 | Hs.123239 | acrosin binding protein |
| NM_004126 | Hs.83381 | "guanine nucleotide binding protein (G protein), gamma 11" |
| Y07846 | Hs.322852 | growth arrest-specific 2 like 1 |
| BE327727 | Hs.443301 | Transcribed sequences |
| M36532 | Hs.155097 | carbonic anhydrase II |
| NM_017526 | Hs.23581 | leptin receptor |
| AW205122 | Hs.496572 | hypothetical protein FLJ22679 |
| AI141116 | Hs.123239 | acrosin binding protein |
| AW293296 | Hs.163893 | Transcribed sequences |
| N63244 | Hs.592143 | "tubulin, beta 1" |
| BG120535 | | "602346858F1 NIH_MGC_90 Homo sapiens cDNA clone IMAGE: 4441695 5', mRNA sequence." |
| AU152763 | Hs.586165 | "CDNA FLJ10742 fis, clone NT2RP3001629" |
| BC003064 | Hs.481980 | "disabled homolog 2, mitogen-responsive phosphoprotein (Drosophila)" |
| N63920 | Hs.596025 | "CDNA clone IMAGE: 5294823, partial cds" |
| BG251467 | Hs.122514 | mitochondrial solute carrier protein |
| AF237762 | Hs.306199 | G protein-coupled receptor 84 |
| AW206560 | Hs.609146 | Transcribed sequences |
| AI971212 | Hs.434494 | synaptojanin 2 |
| AL136805 | Hs.278436 | zinc finger protein 537 |
| BC026299 | Hs.518727 | "Clone IMAGE: 4275461, mRNA" |
| BE675324 | Hs.200770 | Transcribed sequences |
| NM_021647 | Hs.178121 | |
| NM_018482 | Hs.106015 | "synonyms: PAP, PAG2, ASAP1, ZG14P, KIAA1249; Homo sapiens development and differentiation enhancing factor 1 (DDEF1), mRNA." |

TABLE 7-continued

| GenBank ID | Unigene ID | Gene Description |
|---|---|---|
| AA149644 | Hs.150718 | junctional adhesion molecule 3 |
| AF325460 | Hs.351812 | "C-type (calcium dependent, carbohydrate-recognition domain) lectin, superfamily member 7" |
| AW665656 | Hs.633892 | glutamate-ammonia ligase (glutamine synthase) |
| AA417099 | Hs.465709 | Transcribed sequences |
| NM_003897 | Hs.591785 | immediate early response 3 |
| AF275260 | Hs.592117 | chemokine (C-X-C motif) ligand 16 |
| AF001540 | | PRO1073 protein |
| AI640434 | Hs.601545 | hypothetical protein FLJ10357 |
| AW043859 | Hs.235795 | "Clone IMAGE: 5263020, mRNA" |
| H68759 | Hs.122514 | Transcribed sequences |
| NM_004536 | Hs.191356 | baculoviral IAP repeat-containing 1 |
| AF086010 | Hs.335205 | Full length insert cDNA clone YW04H08 |
| NM_003189 | Hs.73828 | T-cell acute lymphocytic leukemia 1 |
| AW138767 | Hs.274256 | hypothetical protein FLJ23563 |
| NM_003693 | Hs.534497 | "scavenger receptor class F, member 1" |
| BG177759 | Hs.497873 | WD repeat domain 26 |
| AW264036 | Hs.478588 | B-cell CLL/lymphoma 6 (zinc finger protein 51) |
| AL119957 | Hs.59214 | "DnaJ (Hsp40) homolog, subfamily C, member 3" |
| NM_018388 | Hs.105134 | muscleblind-like 3 (*Drosophila*) |
| AI640434 | Hs.601545 | hypothetical protein FLJ10357 |
| AI332764 | Hs.516646 | Transcribed sequences |
| AI719730 | Hs.24258 | "guanylate cyclase 1, soluble, alpha 3" |
| NM_130441 | Hs.351812 | "C-type (calcium dependent, carbohydrate-recognition domain) lectin, superfamily member 7" |
| AW796364 | Hs.371594 | Transcribed sequence with weak similarity to protein ref: NP_060265.1 (*H. sapiens*) hypothetical protein FLJ20378 [*Homo sapiens*] |
| BC043380 | Hs.468274 | "CDNA clone IMAGE: 5223469, partial cds" |
| NM_017698 | | |
| AW069181 | Hs.603149 | "cr43e01.x1 Human bone marrow stromal cells Homo sapiens cDNA clone HBMSC_cr43e01 3', mRNA sequence." |
| AF350881 | Hs.272225 | "transient receptor potential cation channel, subfamily M, member 6" |
| AA082707 | Hs.592262 | "myeloid/lymphoid or mixed-lineage leukemia 5 (trithorax homolog, *Drosophila*)" |
| AL035700 | | "continued from bA177G23.1 in Em: AL451064 match: proteins: Tr: O75368 Sw: P55822 Tr: Q9BPY5 Tr: Q9BRB8 Sw: Q9WUZ7; Human DNA sequence from clone RP1-75K24 on chromosome 6q13-15 Contains the the 3' end of the SH3BGRL2 gene for SH3 domain binding glutamic acid-rich protein-like 2, complete sequence." |
| N66571 | Hs.501898 | murine retrovirus integration site 1 homolog |
| AA482548 | Hs.497873 | "zt34b03.s1 Soares ovary tumor NbHOT Homo sapiens cDNA clone IMAGE: 724205 3', mRNA sequence." |
| AI052659 | Hs.334019 | Transcribed sequences |
| AF074331 | | "*Homo sapiens* PAPS synthetase-2 (PAPSS2) mRNA, complete cds." |
| AI682905 | Hs.280342 | "protein kinase, cAMP-dependent, regulatory, type I, alpha (tissue specific extinguisher 1)" |
| AI022066 | Hs.480763 | Transcribed sequences |
| AI953847 | Hs.148741 | IBR domain containing 2 |
| NM_000361 | Hs.2030 | thrombomodulin |
| AY151286 | Hs.196384 | prostaglandin-endoperoxide synthase 2 (prostaglandin G/H synthase and cyclooxygenase) |
| AL713724 | Hs.487994 | MRNA; cDNA DKFZp667O0416 (from clone DKFZp667O0416) |
| AI831952 | Hs.567518 | nudE nuclear distribution gene E homolog 1 (*A. nidulans*) |
| N45231 | Hs.513053 | "DnaJ (Hsp40) homolog, subfamily A, member 4" |
| AA044825 | Hs.520757 | "thromboxane A synthase 1 (platelet, cytochrome P450, family 5, subfamily A)" |
| AI476341 | Hs.93825 | "CDNA FLJ39784 fis, clone SPLEN2002314" |
| BF195718 | Hs.221889 | cold shock domain protein A |
| AL833423 | Hs.379548 | MRNA; cDNA DKFZp313H2139 (from clone DKFZp313H2139) |
| NM_009590 | Hs.143102 | "amine oxidase, copper containing 2 (retina-specific)" |
| AA770170 | Hs.499489 | "c-mir, cellular modulator of immune recognition" |
| BE965029 | Hs.501928 | "601658l2R1 NrH_MGC_69 Homo sapiens cDNA clone IMAGE: 3886131 3', mRNA sequence." |
| BC018042 | Hs.279815 | cysteine sulfinic acid decarboxylase |
| AA218974 | | "zr02g12.s1 Stratagene NT2 neuronal precursor 937230 Homo sapiens cDNA clone IMAGE: 650374 3', mRNA sequence." |
| AF188298 | Hs.481980 | "disabled homolog 2, mitogen-responsive phosphoprotein (*Drosophila*)" |
| NM_005906 | Hs.446125 | male germ cell-associated kinase |
| BC002716 | Hs.496572 | hypothetical protein FLJ22679 |
| AK023512 | Hs.463439 | sperm associated antigen 9 |
| AA010315 | Hs.60371 | Transcribed sequences |
| AF051151 | Hs.135853 | toll-like receptor 5 |
| BU929456 | | "AGENCOURT_10424238 NrH_MGC_79 Homo sapiens cDNA clone IMAGE: 6663343 5', mRNA sequence." |
| NM_002607 | Hs.535898 | platelet-derived growth factor alpha polypeptide |
| AK024748 | Hs.297343 | "calcium/calmodulin-dependent protein kinase kinase 2, beta" |
| U76248 | Hs.477959 | seven in absentia homolog 2 (*Drosophila*) |
| AI819198 | Hs.208229 | G protein-coupled receptor 54 |
| AI452469 | Hs.605187 | Transcribed sequence with weak similarity to protein ref: NP_009032.1 (*H. sapiens*) sarcosine dehydrogenase; dimethylglycine dehydrogenase-like 1 [*Homo sapiens*] |
| AA037483 | Hs.458395 | "zk34a02.s1 Soares_pregnant_uterus_NbHPU Homo sapiens cDNA clone IMAGE: 484682 3', mRNA sequence." |
| U56237 | Hs.631534 | "Fc fragment of IgA, receptor for" |
| N66045 | Hs.29189 | Transcribed sequences |
| AW299958 | Hs.524491 | 3'-phosphoadenosine 5'-phosphosulfate synthase 2 |

TABLE 7-continued

| GenBank ID | Unigene ID | Gene Description |
|---|---|---|
| AK021983 | Hs.106015 | "CDNA FLJ11921 fis, clone HEMBB1000318" |
| NM_002398 | Hs.526754 | "Meis1, myeloid ecotropic viral integration site 1 homolog (mouse)" |
| AV725666 | Hs.220950 | "CDNA clone IMAGE: 4814010, partial cds" |
| AK026714 | Hs.7886 | pellino homolog 1 (*Drosophila*) |
| NM_005373 | Hs.82906 | CDC20 cell division cycle 20 homolog (*S. cerevisiae*) |
| AK024382 | | "unnamed protein product; *Homo sapiens* cDNA FLJ14320 fis, clone PLACE3000455." |
| AA702409 | Hs.592017 | Transcribed sequences |
| AI074467 | Hs.593643 | Transcribed sequences |
| AI368358 | Hs.496969 | N-acetylneuraminate pyruvate lyase (dihydrodipicolinate synthase) |
| H28667 | Hs.444451 | sterile alpha motif and leucine zipper containing kinase AZK |
| AL544951 | Hs.280604 | "AL544951 *Homo sapiens* PLACENTA COT 25-NORMALIZED *Homo sapiens* cDNA clone CS0DI012YC11 5-PRIME, mRNA sequence." |
| AL050388 | Hs.487046 | "superoxide dismutase 2, mitochondrial" |
| AI829674 | Hs.584845 | Transcribed sequences |
| NM_018324 | Hs.24309 | hypothetical protein FLJ11106 |
| AA362254 | Hs.529633 | Transcribed sequences |
| AW130600 | Hs.99472 | MRNA; cDNA DKFZp564O0862 (from clone DKFZp564O0862) |
| N25732 | Hs.591328 | "yx83c03.s1 Soares melanocyte 2NbHM *Homo sapiens* cDNA clone IMAGE: 268324 3', mRNA sequence." |
| NM_017815 | Hs.442782 | chromosome 14 open reading frame 94 |
| AK055448 | | "*Homo sapiens* cDNA FLJ30886 fis, clone FEBRA2005014, weakly similar to ZINC FINGER PROTEIN 84." |
| S69189 | Hs.464137 | "acyl-Coenzyme A oxidase 1, palmitoyl" |
| AU146027 | Hs.592326 | "AU146027 HEMBA1 *Homo sapiens* cDNA clone HEMBA1006595 3', mRNA sequence." |
| BE439987 | Hs.462214 | growth arrest-specific 7 |
| AI363213 | Hs.381058 | KIAA0146 protein |
| BF508786 | Hs.613959 | MRNA; cDNA DKFZp686J24234 (from clone DKFZp686J24234) |
| BF680284 | Hs.34558 | "CDNA: FLJ21199 fis, clone COL00235" |
| H93077 | Hs.519694 | chromosome 5 open reading frame 4 |
| AI798924 | Hs.191850 | Transcribed sequences |
| W19983 | Hs.370725 | oxysterol binding protein-like 1A |
| AA057437 | Hs.458747 | Transcribed sequences |
| NM_024565 | Hs.14070 | hypothetical protein FLJ14166 |
| AI356228 | Hs.515351 | KIAA1533 |
| AI937121 | Hs.29282 | Transcribed sequences |
| AI806045 | Hs.61438 | Transcribed sequences |
| N24643 | Hs.446017 | WD repeat and SOCS box-containing 1 |
| AU122258 | | "AU122258 MAMMA1 *Homo sapiens* cDNA clone MAMMA1002009 5', mRNA sequence." |
| AI278204 | Hs.99472 | MRNA; cDNA DKFZp564O0862 (from clone DKFZp564O0862) |
| AW450374 | Hs.593734 | "Clone IMAGE: 4824518, mRNA" |
| BE888885 | Hs.220950 | "CDNA clone IMAGE: 4814010, partial cds" |
| AK023845 | | ubiquitin specific protease 34 |
| BF511336 | Hs.591641 | Transcribed sequences |
| NM_007199 | Hs.369265 | interleukin-1 receptor-associated kinase 3 |
| AI056872 | Hs.591328 | Transcribed sequences |
| BG251467 | Hs.122514 | mitochondrial solute carrier protein |
| NM_022083 | | chromosome 1 open reading frame 24 |
| AW057518 | Hs.608694 | "elongation factor. RNA polymerase II, 2" |
| AI650285 | Hs.287299 | Transcribed sequence with weak similarity to protein ref: NP_060312.1 (*H. sapiens*) hypothetical protein FLJ20489 [*Homo sapiens*] |
| AU147506 | Hs.7886 | pellino homolog 1 (*Drosophila*) |
| BF435852 | Hs.464137 | "acyl-Coenzyme A oxidase 1, palmitoyl" |
| W03103 | Hs.106015 | "za04b05.r1 Soares melanocyte 2NbHM *Homo sapiens* cDNA clone IMAGE: 291537 5', mRNA sequence." |
| AI458949 | Hs.520414 | interferon gamma receptor 1 |
| AB030034 | Hs.444451 | sterile alpha motif and leucine zipper containing kinase AZK |
| BC011877 | Hs.195403 | "Hypothetical protein LOC286061 (LOC286061), mRNA" |
| AL137028 | | |
| NM_007219 | Hs.589884 | ring finger protein 24 |
| AA868809 | Hs.25447 | "CDNA FLJ43180 fis, clone FCBBF3013846" |
| NM_012329 | Hs.463483 | monocyte to macrophage differentiation-associated |
| AA778783 | Hs.420024 | Transcribed sequence with weak similarity to protein ref: NP_055301.1 (*H. sapiens*) neuronal thread protein [*Homo sapiens*] |
| NM_030918 | Hs.192326 | sorting nexin family member 27 |
| T79640 | Hs.174312 | Transcribed sequences |
| R91734 | | "yp98f04.r1 Soares fetal liver spleen 1NFLS *Homo sapiens* cDNA clone IMAGE: 195487 5', mRNA sequence." |
| U44403 | Hs.75367 | Src-like-adaptor |
| BF591270 | Hs.595473 | "7h44e04.x1 NCI_CGAP_Co16 *Homo sapiens* cDNA clone IMAGE: 3318846 3', mRNA sequence." |
| BC042590 | Hs.434241 | "*Homo sapiens* cDNA clone IMAGE: 4821044, partial cds." |
| NM_018586 | | |
| BE221883 | Hs.11184 | ubiquitin-conjugating enzyme E2R 2 |
| BG337478 | Hs.128037 | "CDNA FLJ38117 fis, clone D3OST2003797" |
| AV723666 | | "AV723666 HTB *Homo sapiens* cDNA clone HTBABA11 5', mRNA sequence." |
| AK025898 | Hs.525232 | low density lipoprotein receptor-related protein 10 |

TABLE 7-continued

| GenBank ID | Unigene ID | Gene Description |
|---|---|---|
| AB062477 | | "Homo sapiens OK/SW-cl.41 mRNA, complete cds." |
| AW467357 | Hs.371720 | spleen tyrosine kinase |
| AI808120 | Hs.479766 | TPA regulated locus |
| BE966748 | | "601661247R1 NIH_MGC_72 Homo sapiens cDNA clone IMAGE: 3916235 3', mRNA sequence." |
| AK024677 | Hs.632602 | N-acylsphingosine amidohydrolase (acid ceramidase)-like |
| AL038191 | Hs.474536 | "DKFZp566P1724_s1 566 (synonym: hfkd2) Homo sapiens cDNA clone DKFZp566P1724 3', mRNA sequence." |
| BG432887 | Hs.442789 | "Transcribed sequence with weak similarity to protein ref: NP_005210.1 (H. sapiens) diaphanous 1; Diaphanous, Drosophila, homolog of, 1; deafness, autosomal dominant 1; diaphanous" |
| BF516252 | Hs.528703 | ankyrin repeat domain 13 |
| AA576497 | Hs.492740 | activating transcription factor 6 |
| NM_017593 | Hs.146551 | BMP2 inducible kinase |
| NM_003105 | Hs.368592 | "sortilin-related receptor, L(DLR class) A repeats-containing" |
| AA706922 | Hs.517034 | Transcribed sequences |
| AI963142 | Hs.48353 | "CDNA FLJ32274 fis, clone PROST2000036" |
| AI735391 | Hs.146551 | "at10e09.x1 Barstead aorta HPLRB6 Homo sapiens cDNA clone IMAGE: 2354728 3', mRNA sequence." |
| AI807658 | Hs.192326 | Transcribed sequences |
| BE693389 | | Transcribed sequences |
| N32832 | Hs.159430 | FAD 104 |
| AF015452 | Hs.390736 | CASP8 and FADD-like apoptosis regulator |
| AL049273 | Hs.429434 | MRNA; cDNA DKFZp564H023 (from clone DKFZp564H023) |
| BC039388 | Hs.237886 | "Clone IMAGE: 5298774, mRNA" |
| AA382004 | Hs.122514 | "EST95296 Activated T-cells II Homo sapiens cDNA 5' end, mRNA sequence." |
| BG334495 | Hs.631749 | hypothetical protein LOC284021 |
| AW367571 | Hs.438673 | hypothetical protein LOC338692 |
| AI084056 | Hs.464217 | phosphatidylglycerophosphate synthase |
| AK054840 | Hs.106015 | "CDNA FLJ30278 fis, clone BRACE2002755" |
| AI051950 | Hs.99472 | MRNA; cDNA DKFZp564O0862 (from clone DKFZp564O0862) |
| BF724303 | Hs.412293 | Transcribed sequences |
| AK000794 | Hs.520757 | "CDNA FLJ20787 fis, clone COL02178" |
| AF153820 | Hs.1547 | "potassium inwardly-rectifying channel, subfamily J, member 2" |
| BE671084 | Hs.293593 | GTPase regulator associated with focal adhesion kinase pp125(FAK) |
| AU146685 | Hs.126667 | "CDNA FLJ11971 fis, clone HEMBB1001208" |
| AI962978 | Hs.469244 | "WAS protein family, member 2" |
| AI634046 | Hs.390736 | CASP8 and FADD-like apoptosis regulator |
| AW297879 | Hs.436271 | Transcribed sequences |
| AK025534 | Hs.588289 | "CDNA: FLJ21881 fis, clone HEP02746" |
| N72610 | Hs.484363 | "Transcribed sequence with strong similarity to protein pdb: 1BGM (E. coli) O Chain O, Beta-Galactosidase" |
| BF056507 | Hs.372000 | neutral sphingomyelinase (N-SMase) activation associated factor |
| W87434 | Hs.106015 | Transcribed sequence with moderate similarity to protein sp: P39188 (H. sapiens) ALU1_HUMAN Alu subfamily J sequence contamination warning entry |
| AF085978 | Hs.474596 | Homo sapiens full length insert cDNA clone YT87E05. |
| N63821 | Hs.175437 | "za26c12.s1 Soares fetal liver spleen 1NFLS Homo sapiens cDNA clone IMAGE: 293686 3', mRNA sequence." |
| AV700891 | Hs.517296 | v-ets erythroblastosis virus E26 oncogene homolog 2 (avian) |
| AI692401 | Hs.29282 | Transcribed sequences |
| N52625 | Hs.603141 | "yv37f12.s1 Soares fetal liver spleen 1NFLS Homo sapiens cDNA clone IMAGE: 244943 3' similar to contains element MER22 repetitive element;, mRNA sequence." |
| R45471 | Hs.479396 | recombining binding protein suppressor of hairless (Drosophila) |
| H67156 | Hs.122514 | Transcribed sequences |
| BF724558 | Hs.636976 | Transcribed sequence with moderate similarity to protein pir: T02670 (H. sapiens) T02670 probable thromboxane A2 receptor isoform beta - human |
| BE551054 | Hs.279583 | DORA reverse strand protein 1 |
| NM_021213 | Hs.285218 | phosphatidylcholine transfer protein |
| N93399 | Hs.494406 | "CDNA FLJ46484 fis, clone THYMU3026350" |
| BF668314 | Hs.221497 | PRO0149 protein |
| NM_002213 | Hs.536663 | "integrin, beta 5" |
| AW974609 | Hs.136398 | "zinc finger, CCHC domain containing 6" |
| AK001393 | Hs.134857 | hypothetical protein MGC12458 |
| NM_000313 | Hs.64016 | protein S (alpha) |
| AW027474 | Hs.446678 | nuclear receptor coactivator 2 |
| AI422414 | Hs.484551 | Transcribed sequences |
| NM_004196 | Hs.280881 | cyclin-dependent kinase-like 1 (CDC2-related kinase) |
| AI374686 | Hs.122523 | Transcribed sequences |
| AW184034 | Hs.600998 | v-raf murine sarcoma viral oncogene homolog B1 |
| BC025707 | Hs.484099 | "potassium large conductance calcium-activated channel, subfamily M, beta member 1" |
| AA815354 | Hs.520684 | "Hypothetical LOC284527 (LOC284527), mRNA" |
| AF306674 | Hs.132050 | hypothetical protein MGC40368 |
| W93728 | Hs.77890 | "guanylate cyclase 1, soluble, beta 3" |
| NM_003326 | Hs.181097 | "tumor necrosis factor (ligand) superfamily, member 4 (tax-transcriptionally activated glycoprotein 1, 34 kDa)" |
| R62432 | Hs.211252 | "solute carrier family 24 (sodium/potassium/calcium exchanger), member 3" |
| AI821895 | Hs.433060 | Transcribed sequences |
| AW051591 | Hs.388364 | hypothetical protein LOC285533 |
| NM_000187 | Hs.368254 | "homogentisate 1,2-dioxygenase (homogentisate oxidase)" |
| AK023837 | Hs.159799 | thyroid hormone receptor associated protein 2 |

TABLE 7-continued

| GenBank ID | Unigene ID | Gene Description |
|---|---|---|
| BF446281 | Hs.433307 | "branched chain keto acid dehydrogenase E1, alpha polypeptide (maple syrup urine disease)" |
| BE046521 | Hs.191482 | "cut-like 1, CCAAT displacement protein (*Drosophila*)" |
| AW006409 | Hs.532144 | "histone 1, H3d" |
| AI476341 | Hs.93825 | "CDNA FLJ39784 fis, clone SPLEN2002314" |
| BF512068 | Hs.575090 | Transcribed sequences |
| AA488687 | Hs.390594 | "solute carrier family 7, (cationic amino acid transporter, y+ system) member 11" |
| NM_002413 | Hs.81874 | microsomal glutathione S-transferase 2 |
| R64696 | | "yi22f12.r1 Soares placenta Nb2HP *Homo sapiens* cDNA clone IMAGE: 140015 5' similar to contains Alu repetitive element;, mRNA sequence." |
| AV699911 | Hs.310421 | Transcribed sequence with weak similarity to protein sp: P23961 (*H. sapiens*) ALUC_HUMAN!!!! ALU CLASS C WARNING ENTRY!!!! |
| NM_002350 | Hs.491767 | v-yes-1 Yamaguchi sarcoma viral related oncogene homolog |
| AI698731 | Hs.202238 | Transcribed sequences |
| AA215519 | | "zr97a07.r1 NCI_CGAP_GCB1 *Homo sapiens* cDNA clone IMAGE: 683604 5', mRNA sequence." |
| BC000195 | Hs.279583 | DORA reverse strand protein 1 |
| AW304786 | Hs.507260 | "solute carrier family 15, member 4" |
| AA705029 | Hs.529488 | "Transcribed sequence with strong similarity to protein pdb: 1BGM (*E. coli*) O Chain O, Beta-Galactosidase" |
| BC020868 | Hs.632256 | signal transducer and activator of transcription 5B |
| BM849515 | Hs.636486 | leucine-rich repeat kinase 1 |
| AW269743 | Hs.254477 | "CDNA FLJ20182 fis, clone COLF0190" |
| BC039825 | Hs.446125 | male germ cell-associated kinase |
| NM_014339 | Hs.129751 | interleukin 17 receptor |
| AW196696 | Hs.484363 | Transcribed sequence with strong similarity to protein ref: NP_060904.1 (*H. sapiens*) goliath protein; likely ortholog of mouse g1-related zinc finger protein [*Homo sapiens*] |
| AI583964 | Hs.544636 | Transcribed sequences |
| BE552138 | Hs.632488 | complement component (3b/4b) receptor 1-like |
| AI738802 | Hs.644106 | cyclin-dependent kinase (CDC2-like) 11 |
| BC025708 | Hs.592017 | hypothetical protein FLJ11175 |
| BE327650 | Hs.369978 | hypothetical protein FLJ11753 |
| AI972498 | Hs.97469 | "Clone IMAGE: 4812754, mRNA" |
| AI668625 | Hs.380094 | Full length insert cDNA YO61D09 |
| AI342132 | Hs.485241 | "qt26c08.x1 Soares_pregnant_uterus_NbHPU *Homo sapiens* cDNA clone IMAGE: 1949102 3', mRNA sequence." |
| AF350251 | Hs. 132868 | ubiquitin specific protease 32 |
| BC038707 | Hs.420559 | "*Homo sapiens*, Similar to neuronal thread protein, clone IMAGE: 3932744, mRNA." |
| AK022004 | Hs.106015 | "CDNA FLJ11942 fis, clone HEMBB1000652" |
| BF512846 | Hs.471461 | acyl-CoA synthetase long-chain family member 3 |
| AW450403 | Hs.97270 | "family with sequence similarity 13, member A1" |
| AW268357 | Hs. 132868 | ubiquitin specific protease 32 |
| AF207547 | Hs.78960 | "LATS, large tumor suppressor, homolog 2 (*Drosophila*)" |
| AK025759 | Hs.592692 | Clone 23872 mRNA sequence |
| AW002073 | Hs.606630 | Transcribed sequences |
| AW974815 | Hs.444451 | Transcribed sequences |
| AW294022 | Hs.308710 | KIAA1718 protein |
| AI740571 | Hs.159130 | Transcribed sequence with weak similarity to protein sp: P39188 (*H. sapiens*) ALU1_HUMAN Alu subfamily J sequence contamination warning entry |
| AI290654 | Hs.26403 | hypothetical protein LOC283578 |
| AW119113 | Hs.2030 | thrombomodulin |
| R71245 | | "yi54e05.s1 Soares placenta Nb2HP *Homo sapiens* cDNA clone IMAGE: 143072 3' similar to gb: M21121 T-CELL SPECIFIC RANTES PROTEIN PRECURSOR (HUMAN);, mRNA sequence." |
| BF357738 | Hs.584811 | Transcribed sequences |
| AW020871 | Hs.499209 | "CDNA FLJ90139 fis, clone HEMBB1001026, weakly similar to ENDOSOMAL P24A PROTEIN PRECURSOR." |
| BE962615 | Hs.643691 | sorting nexin 3 |
| NM_144665 | Hs.191599 | sestrin 3 |
| AA252762 | Hs.505516 | KIAA1463 protein |
| AI023699 | Hs.371594 | MAP kinase-interacting serine/threonine kinase 1 |
| AW502463 | Hs.504096 | Cas-Br-M (murine) ecotropic retroviral transforming sequence |
| AK096134 | Hs.378150 | "Chromosome 4 unknown transcript 1 variant 2 mRNA, partial sequence, alternatively spliced" |
| AW291297 | Hs.420272 | "H2A histone family, member Y" |
| AA524299 | Hs.525232 | Transcribed sequence with moderate similarity to protein sp: P39192 (*H. sapiens*) ALU5_HUMAN Alu subfamily SC sequence contamination warning entry |
| BE503981 | Hs.420272 | "H2A histone family, member Y" |
| BE894882 | Hs.130853 | "601434066F1 NIH_MGC_72 *Homo sapiens* cDNA clone IMAGE: 3919073 5', mRNA sequence." |
| AV700946 | Hs.432337 | Transcribed sequence with weak similarity to protein pir: I49130 (*M. musculus*) I49130 reverse transcriptase - mouse |
| BF002625 | Hs.612374 | Transcribed sequences |
| AW295340 | Hs.99691 | Transcribed sequence with weak similarity to protein sp: P39192 (*H. sapiens*) ALU5_HUMAN Alu subfamily SC sequence contamination warning entry |
| BF062244 | Hs.144333 | lin-7 homolog A (*C. elegans*) |
| AF050145 | Hs.460960 | iduronate 2-sulfatase (Hunter syndrome) |
| AK091836 | Hs.484678 | MRNA; cDNA DKFZp686I05132 (from clone DKFZp686I05132) |
| AI939422 | Hs.461253 | Transcribed sequences |
| D29805 | Hs.272011 | "UDP-Gal: betaGlcNAc beta 1,4-galactosyltransferase, polypeptide 1" |
| NM_025158 | Hs.306769 | RUN and FYVE domain containing 1 |
| AA195936 | Hs.82719 | hypothetical protein MGC21416 |

TABLE 7-continued

| GenBank ID | Unigene ID | Gene Description |
|---|---|---|
| AI079521 | Hs.594059 | fring |
| AF130091 | Hs.72071 | potassium channel tetramerisation domain containing 9 |
| BC020843 | Hs.616365 | hepatitis A virus cellular receptor 2 |
| AW301766 | Hs.527653 | "decay accelerating factor for complement (CD55, Cromer blood group system)" |
| BC035084 | Hs.536364 | Full length insert cDNA clone ZD78D03 |
| BC008306 | Hs.287471 | NICE-3 protein |
| M24779 | Hs.81170 | pim-1 oncogene |
| BM014995 | | "603640947F1 NIH_MGC_87 Homo sapiens cDNA clone IMAGE: 5417266 5', mRNA sequence." |
| BC020868 | Hs.632256 | signal transducer and activator of transcription 5B |
| T83380 | | "ye03h05.s1 Soares fetal liver spleen 1NFLS Homo sapiens cDNA clone IMAGE: 116697 3', mRNA sequence." |
| N39126 | Hs.191346 | Transcribed sequences |
| AB053312 | Hs.390736 | "ALS2CR10 mRNA,." |
| BF223935 | Hs.268774 | Transcribed sequences |
| X62009 | Hs.519294 | fibrillin 2 (congenital contractural arachnodactyly) |
| BF508977 | Hs.463059 | signal transducer and activator of transcription 3 (acute-phase response factor) |
| BF510533 | Hs.642655 | Transcribed sequences |
| AK024177 | Hs.529860 | "Homo sapiens CDNA FLJ14115 fis, clone MAMMA1001760." |
| AI754064 | Hs.532315 | "solute carrier family 31 (copper transporters), member 1" |
| BC016012 | Hs.471492 | "eukaryotic translation initiation factor 2C, 4" |
| BE083088 | Hs.591602 | "RC2-BT0642-030400-021-C05 BT0642 Homo sapiens cDNA, mRNA sequence." |
| BC040178 | | "Homo sapiens GTP binding protein 5 (putative), mRNA (cDNA clone IMAGE: 4797390), with apparent retained intron." |
| AL039447 | Hs.642739 | chromosome 9 open reading frame 48 |
| AL832141 | Hs.369592 | thyroid adenoma associated |
| AL555336 | Hs.380635 | Transcribed sequence with moderate similarity to protein pir: B28096 (H. sapiens) B28096 line-1 protein ORF2 - human |
| AF315688 | Hs.591083 | "interferon, kappa" |
| AI749193 | Hs.374067 | ubiquitin protein ligase E3B |
| AI201594 | Hs.568928 | MRNA; cDNA DKFZp762M127 (from clone DKFZp762M127) |
| NM_004488 | | glycoprotein V (platelet) |
| BC013319 | Hs.506381 | "FYVE, RhoGEF and PH domain containing 6" |
| NM_002359 | Hs.252229 | v-maf musculoaponeurotic fibrosarcoma oncogene homolog G (avian) |
| AI357616 | Hs.127934 | hypothetical protein LOC90133 |
| AU146585 | Hs.386168 | "CDNA FLJ10258 fis, clone HEMBB1000908" |
| M62762 | | "Human vacuolar H+ ATPase proton channel subunit mRNA, complete cds." |
| BG109846 | Hs.616796 | protein x 013 |
| NM_005890 | | "synonyms: MGC1348, KIAA0394; isoform b is encoded by transcript variant b; go_component: kinesin complex [goid 0005871] [evidence IEA]; go_function: transcription factor activity [goid 0003700] [evidence TAS] [pmid 9736752]; go_process: cell cycle arrest [goid 0007050] [evidence TAS] [pmid 9736752]; go_process: cell growth and/or maintenance [goid 0008151] [evidence IEA]; go_process: development [goid 0007275] [evidence IEA]; go_process: neurogenesis [goid 0007399] [evidence IEA]; Homo sapiens growth arrest-specific 7 (GAS7), transcript variant b, mRNA." |
| AB040966 | Hs.515351 | KIAA1533 |
| AI652645 | Hs.475506 | KIAA0763 gene product |
| AK022387 | Hs.491682 | "protein kinase, DNA-activated, catalytic polypeptide" |
| AK023308 | | "unnamed protein product; Homo sapiens CDNA FLJ13246 fis, clone OVARC1000682, highly similar to PROCESSING ALPHA-1,2-MANNOSIDASE (EC 3.2.1.—)." |
| BE855963 | Hs.508725 | hypothetical protein FLJ12118 |
| NM_005955 | Hs.591505 | metal-regulatory transcription factor 1 |
| AF132033 | | "intelligence reducing insertion protein INGRIN; Homo sapiens OPA-containing protein (HOPA) gene, complete cds." |
| NM_024822 | | "synonyms: FLJ22601, dJ1158H2.1; Homo sapiens hypothetical protein FLJ22843 (FLJ22843), mRNA." |
| BE856376 | Hs.250616 | lipidosin |
| AI684710 | Hs.514920 | nuclear domain 10 protein |
| NM_018407 | Hs.492314 | lysosomal associated protein transmembrane 4 beta |
| AF086079 | Hs.231895 | Full length insert cDNA clone YZ82H07 |
| BC026969 | Hs.492716 | "Homo sapiens unknown MGC21654 product, mRNA (cDNA clone IMAGE: 5116073), partial cds." |
| AK000834 | Hs.449434 | "Homo sapiens CDNA FLJ20827 fis, clone ADKA03543." |
| AF086444 | Hs.390420 | Full length insert cDNA clone ZD81E01 |
| NM_015322 | Hs.362733 | fem-1 homolog b (C. elegans) |
| NM_016172 | Hs.9194 | ubiquitin associated domain containing 1 |
| AL713719 | Hs.29189 | MRNA; cDNA DKFZp667K1916 (from clone DKFZp667K1916) |
| AA897191 | Hs.279245 | "transforming, acidic coiled-coil containing protein 1" |
| R91245 | | "yp94d10.s1 Soares fetal liver spleen 1NFLS Homo sapiens cDNA clone IMAGE: 195091 3', mRNA sequence." |
| AI867175 | Hs.504907 | chromosome 20 open reading frame 106 |
| BG149547 | Hs.408458 | Transcribed sequences |
| NM_012204 | Hs.22302 | "general transcription factor IIIC, polypeptide 4, 90 kDa" |
| NM_025244 | Hs.120267 | "testis specific, 10" |
| BF433757 | Hs.528993 | ralA binding protein 1 |
| BC026007 | Hs.41735 | "Clone IMAGE: 4704511, mRNA" |
| BC014891 | Hs.620701 | KIAA0701 protein |
| AW590925 | Hs.419240 | Transcribed sequences |
| AL080215 | Hs.516578 | MRNA; cDNA DKFZp586J0323 (from clone DKFZp586J0323) |
| X13230 | Hs.387262 | MCF.2 cell line derived transforming sequence |
| AI821782 | Hs.97858 | Transcribed sequences |

TABLE 7-continued

| GenBank ID | Unigene ID | Gene Description |
|---|---|---|
| BI869014 | Hs.627200 | "CDNA FLJ33783 fis, clone BRSSN2007504" |
| BF434655 | Hs.6734 | "7p02f01.x1 NCI_CGAP_Ov18 Homo sapiens cDNA clone IMAGE: 3644688 3', mRNA sequence." |
| AK026026 | Hs.474150 | BH3 interacting domain death agonist |
| AI819386 | Hs.634057 | MRNA; cDNA DKFZp686B 14224 (from clone DKFZp686B14224) |
| BF969352 | Hs.195080 | "CDNA clone IMAGE: 4152985, partial cds" |
| AU145749 | Hs.20516 | "CDNA FLJ11764 fis, clone HEMBA1005685" |
| NM_006547 | Hs.432616 | IGF-II mRNA-binding protein 3 |
| L11702 | Hs.591810 | glycosylphosphatidylinositol specific phospholipase D1 |
| BE326728 | Hs.642633 | hypothetical protein MGC11266 |
| AW379790 | Hs.200063 | "RC3-HT0253-181099-011-c03 HT0253 Homo sapiens cDNA, mRNA sequence." |
| NM_023034 | Hs.608111 | Wolf-Hirschhorn syndrome candidate 1-like 1 |
| AI936976 | Hs.509017 | "glycine-, glutamate-, thienylcyclohexylpiperidine-binding protein" |
| BC033224 | Hs.207457 | DKFZP434L187 protein |
| BC015590 | Hs.382046 | "CDNA clone IMAGE: 4643842, partial cds" |
| AU144449 | | Transcribed sequence with moderate similarity to protein ref: NP_071431.1 (*H. sapiens*) cytokine receptor-like factor 2; cytokine receptor CRL2 precursor [*Homo sapiens*] |
| AB029030 | Hs.21554 | KIAA1107 protein |
| AI935717 | Hs.471637 | hypothetical protein MGC42174 |
| AL050042 | Hs.538604 | *Homo sapiens* mRNA; cDNA DKFZp566L0824 (from clone DKFZp566L0824). |
| NM_024743 | Hs.122583 | hypothetical protein FLJ21934 |
| BC017894 | Hs.420024 | chromosome 10 open reading frame 46 |
| NM_024516 | Hs.632177 | hypothetical protein MGC4606 |
| AI214466 | Hs.283011 | "qg69b04.x1 Soares_NFL_T_GBC_S1 Homo sapiens cDNA clone IMAGE: 1840399 3' similar to TR: Q13443 Q13443 METALLOPROTEASE/DISINTEGRIN/CYSTEINE-RICH PROTEIN PRECURSOR.;, mRNA sequence." |
| BC039406 | Hs.623811 | "Clone IMAGE: 5300951, mRNA" |
| AI280108 | Hs.487511 | chromosome 7 open reading frame 26 |
| AL031228 | | |
| AL139228 | | "match: proteins: Sw: P51151 Sw: P24408; Human DNA sequence from clone RP4-540A13 on chromosome Xq22.1-22.3 Contains the gene for a novel protein similar to RAB9 (member RAS oncogene family), ESTs, STSS and GSSs, complete sequence." |
| BC001793 | Hs.412468 | kelch domain containing 3 |
| AV741657 | Hs.633089 | amine oxidase (flavin containing) domain 2 |
| AF078842 | Hs.323342 | "hqp0207; similar to bovine and pig tubulin-tyrosine ligase (TTL): Swiss-Prot Accession Numbers P38584 and P38160; Homo sapiens HOTTL protein mRNA, complete cds." |
| NM_017686 | Hs.632427 | ganglioside induced differentiation associated protein 2 |
| AL390171 | Hs.480356 | vacuolar protein sorting 52 (yeast) |
| AI796581 | Hs.438550 | KIAA0056 protein |
| BE781103 | Hs.43619 | lung cancer metastasis-related protein 1 |
| NM_024531 | Hs.6459 | putative G-protein coupled receptor GPCR41 |
| AW628835 | Hs.444950 | "TBC1 domain family, member 10" |
| NM_017876 | Hs.69554 | ring finger protein 126 |
| AB011117 | Hs.128627 | signal-induced proliferation-associated 1 like 3 |
| NM_016579 | Hs.558499 | 8D6 antigen |
| NM_016292 | Hs.30345 | heat shock protein 75 |
| AA534894 | Hs.162659 | chromosome 9 open reading frame 28 |
| NM_006876 | Hs.8526 | "UDP-GlcNAc: betaGal beta-1,3-N-acetylglucosaminyltransferase 6" |
| R67325 | Hs.588291 | "Hypothetical protein LOC255512, mRNA (cDNA clone IMAGE: 5274144), partial cds" |
| AL050022 | Hs.438991 | DKFZP564D116 protein |
| AF219116 | Hs.415299 | inosine triphosphatase (nucleoside triphosphate pyrophosphatase) |
| NM_020153 | Hs.533738 | hypothetical protein FLJ21827 |
| NM_145315 | Hs.259666 | lactation elevated 1 |
| BC005133 | Hs.326586 | tRNA splicing 2' phosphotransferase 1 |
| AA514326 | Hs.334684 | hypothetical protein MGC10485 |
| M99436 | Hs.332173 | "transducin-like enhancer of split 2 (E(sp1) homolog, *Drosophila*)" |
| NM_012236 | Hs.571874 | sex comb on midleg homolog 1 (*Drosophila*) |
| H07095 | | "yl81h11.s1 Soares infant brain 1NIB Homo sapiens cDNA clone IMAGE: 44797 3', mRNA sequence." |
| AK000185 | Hs.306389 | "CDNA FLJ20178 fis, clone COL09990" |
| BE677453 | Hs.91531 | "myeloid/lymphoid or mixed-lineage leukemia (trithorax homolog, *Drosophila*); translocated to, 6" |
| AA425633 | | "zv47a01.s1 Soares ovary tumor NbHOT Homo sapiens cDNA clone IMAGE: 756744 3', mRNA sequence." |
| W22625 | | "71E5 Human retina cDNA Tsp509I-cleaved sublibrary Homo sapiens cDNA not directional, mRNA sequence." |
| N21279 | | "yx53c01.s1 Soares melanocyte 2NbHM Homo sapiens cDNA clone IMAGE: 265440 3', mRNA sequence." |
| M77171 | | "Human zinc finger protein gene, partial cds." |
| NM_014015 | Hs.592051 | dexamethasone-induced transcript |
| AW016250 | Hs.604838 | "UI-H-BI0p-abl-c-02-0-UI.s1 NCI_CGAP_Sub2 Homo sapiens cDNA clone IMAGE: 2712171 3', mRNA sequence." |
| AB011173 | Hs.591518 | amine oxidase (flavin containing) domain 2 |
| NM_001667 | Hs.502836 | sorting nexin 15 |
| NM_017514 | Hs.632839 | likely ortholog of mouse plexin 3 |
| AK026088 | Hs.493739 | ubiquitin associated protein 2 |
| AA404269 | Hs.524348 | prickle-like 1 (*Drosophila*) |
| NM_017637 | Hs.435309 | |
| BC001745 | | DNA segment on chromosome 4 (unique) 234 expressed sequence |
| D38122 | Hs.2007 | "tumor necrosis factor (ligand) superfamily, member 6" |

TABLE 7-continued

| GenBank ID | Unigene ID | Gene Description |
|---|---|---|
| AI096888 | Hs.475334 | KIAA0280 protein |
| AV702405 | Hs.632801 | emopamil binding protein (sterol isomerase) |
| NM_015540 | Hs.371045 | DKFZP727M111 protein |
| NM_012222 | Hs.271353 | mutY homolog (E. coli) |
| NM_000386 | Hs.371914 | bleomycin hydrolase |
| NM_014593 | Hs.180933 | CXXC finger 1 (PHD domain) |
| NM_024096 | Hs.632191 | XTP3-transactivated protein A |
| AI885290 | Hs.445818 | "spondin 1, extracellular matrix protein" |
| AK002076 | Hs.517948 | DEAH (Asp-Glu-Ala-His) box polypeptide 30 |
| NM_018127 | Hs.434232 | elaC homolog 2 (E. coli) |
| AF190863 | Hs.460336 | "golgi associated, gamma adaptin ear containing, ARF binding protein 2" |
| BE646227 | Hs.613098 | "protein tyrosine phosphatase, non-receptor type 23" |
| AW572279 | Hs.515840 | DNA (cytosine-5-)-methyltransferase 3 alpha |
| N49268 | Hs.373857 | Kruppel-like factor 12 |
| D26351 | Hs.65758 | "inositol 1,4,5-triphosphate receptor, type 3" |
| BG149482 | | "nad29d02.x1 NCI_CGAP_Lu24 Homo sapiens cDNA clone IMAGE: 3366939 3' similar to contains L1.t1 L1 L1 repetitive element;, mRNA sequence." |
| NM_024102 | Hs.204773 | MEP50 protein |
| NM_001610 | Hs.532492 | "acid phosphatase 2, lysosomal" |
| NM_024765 | | |
| BF110434 | Hs.562802 | hypothetical protein R29124_1 |
| BC030552 | Hs.302963 | "Clone IMAGE: 5223566, mRNA" |
| AW571582 | Hs.618112 | "amyloid beta (A4) precursor protein-binding, family A, member 2 (X11-like)" |
| BC000638 | Hs.514151 | gasdermin-like |
| M57707 | Hs.1497 | "retinoic acid receptor, gamma" |
| NM_024092 | Hs.13662 | hypothetical protein MGC5508 |
| AB011087 | Hs.495349 | KIAA0515 |
| AK094684 | Hs.363407 | "LOC401124 (LOC401124), mRNA" |
| BC003170 | Hs.490551 | NICE-4 protein |
| AB033832 | Hs.352298 | platelet derived growth factor D |
| AL359941 | Hs.593311 | programmed cell death 6 |
| NM_015185 | Hs.54697 | |
| BC019022 | Hs.531856 | hypothetical gene supported by BC007071 |
| AU154785 | Hs.31532 | "AU154785 NT2RP4 Homo sapiens cDNA clone NT2RP4002888 3', mRNA sequence." |
| BF508604 | Hs.632709 | regulator of nonsense transcripts 1 |
| AF308301 | Hs.18946 | mitochondrial ribosomal protein S26 |
| AA634138 | Hs.593575 | chromosome 6 open reading frame 49 |
| BF339831 | Hs.239500 | hypothetical protein MGC13114 |
| AI952009 | Hs.523009 | "sparc/osteonectin, cwcv and kazal-like domains proteoglycan (testican) 2" |
| N29877 | Hs.596783 | taxilin |
| AW190316 | Hs.221447 | NADH: ubiquinone oxidoreductase MLRQ subunit homolog |
| N62126 | Hs.32374 | deltex 3 homolog (Drosophila) |
| BF447901 | Hs.97837 | "Similar to Group X secretory phospholipase A2 precursor (Phosphatidylcholine 2-acylhydrolase GX) (GX sPLA2) (SPLA2-X) (LOC388229), mRNA" |
| NM_022743 | Hs.567571 | SET and MYND domain containing 3 |
| AL133055 | Hs.636446 | hypothetical protein DKFZp434J1015 |
| D49958 | Hs.75819 | glycoprotein M6A |
| U37012 | Hs.493202 | "cleavage and polyadenylation specific factor 1, 160 kDa" |
| AI692169 | Hs.379186 | "wd37e07.x1 Soares_NFL_T_GBC_S1 Homo sapiens cDNA clone IMAGE: 2330340 3', mRNA sequence." |
| AK024800 | Hs.612887 | "CDNA: FLJ21147 fis, clone CAS09371" |
| NM_002378 | Hs.631845 | megakaryocyte-associated tyrosine kinase |
| BF057784 | Hs.187884 | G protein-coupled receptor 114 |
| BF038366 | Hs.199695 | hypothetical protein MAC30 |
| U92706 | | "Human rearranged immunoglobulin heavy chain (A1VH3) gene, partial cds." |
| AA833716 | Hs.460336 | KIAA1970 protein |
| M98528 | | "Homo sapiens neuron-specific protein gene, last exon, clone D4S234." |
| NM_007181 | | mitogen-activated protein kinase kinase kinase kinase 1 |
| AF054994 | Hs.31290 | Clone 23832 mRNA sequence |
| NM_006255 | Hs.333907 | "protein kinase C, eta" |
| AC006033 | | "Homo sapiens, Similar to steroidogenic acute regulatory protein related, clone MGC: 3251 IMAGE: 3505985, mRNA, complete cds.; H_NH0121A08.9 This gene was based on gi(13111773 13543614 14042926); Homo sapiens BAC clone RP11-121A8 from 7, complete sequence." |
| AF016535 | Hs.489033 | "ATP-binding cassette, sub-family B (MDR/TAP), member 1" |
| AA744529 | Hs.95424 | mitogen-activated protein kinase kinase kinase kinase 1 |
| AU145682 | Hs.308048 | early B-cell factor |
| U76542 | Hs.500645 | pyrroline-5-carboxylate synthetase (glutamate gamma-semialdehyde synthetase) |
| AA723370 | Hs.546387 | CGI-105 protein |
| AL521959 | Hs.487479 | "pleckstrin homology, Sec7 and coiled-coil domains 3" |
| W67995 | Hs.54943 | fracture callus 1 homolog (rat) |
| NM_020187 | Hs.458320 | DC12 protein |
| NM_052931 | Hs.492348 | SLAM family member 6 |
| AW083371 | Hs.173878 | nipsnap homolog 1 (C. elegans) |
| AL049942 | Hs.213735 | zinc finger protein 337 |
| AV700174 | Hs.292580 | hypothetical protein LOC283551 |
| NM_017773 | Hs.272794 | hypothetical protein FLJ20340 |
| NM_001628 | Hs.521212 | "aldo-keto reductase family 1, member B1 (aldose reductase)" |

TABLE 7-continued

| GenBank ID | Unigene ID | Gene Description |
|---|---|---|
| AF225422 | | "*Homo sapiens* AD023 mRNA, complete cds." |
| X02189 | | *H. sapiens* adenosine deaminase (ADA) gene 5' flanking region and exon 1 (and joined CDS). |
| NM_014450 | Hs.88012 | SHP2-interacting transmembrane adaptor protein |
| BF345244 | Hs.378501 | hypothetical protein LOC283989 |
| AI057637 | Hs.234898 | acetyl-Coenzyme A carboxylase beta |
| BC002918 | Hs.213088 | carbohydrate (chondroitin 4) sulfotransferase 12 |
| X79782 | Hs.449601 | *H. sapiens* (T1.1) mRNA for IG lambda light chain |
| NM_024310 | Hs.466383 | "pleckstrin homology domain containing, family F (with FYVE domain) member 1" |
| BF116060 | Hs.519783 | FLJ44216 protein |
| Y11339 | Hs.105352 | "sialyltransferase 7 ((alpha-N-acetylneuraminyl-2,3-beta-galactosyl-1,3)-N-acetyl galactosaminide alpha-2,6-sialyltransferase) A" |
| BC003379 | Hs.632714 | hypothetical protein from clone 643 |
| NM_024947 | Hs.529592 | polyhomeotic like 3 (*Drosophila*) |
| NM_000878 | Hs.474787 | "interleukin 2 receptor, beta" |
| AF031138 | Hs.509513 | natural cytotoxicity triggering receptor 3 |
| NM_014914 | Hs.435039 | "centaurin, gamma 2" |
| NM_030978 | Hs.132499 | "actin related protein 2/3 complex, subunit 5-like" |
| NM_004758 | Hs.112499 | benzodiazapine receptor (peripheral) associated protein 1 |
| AW338214 | Hs.437696 | "Clone IMAGE: 5275753, mRNA" |
| AJ238374 | | "*Homo sapiens* mRNA for putative protein TH1, partial, clone IMAGE ID 785447." |
| AF288573 | Hs.2007 | "tumor necrosis factor (ligand) superfamily, member 6" |
| NM_031213 | Hs.465542 | hypothetical protein MGC5244 |
| AF044954 | Hs.513266 | "NADH dehydrogenase (ubiquinone) 1 beta subcomplex, 10, 22 kDa" |
| BE671663 | Hs.592102 | epidermodysplasia verruciformis 2 |
| NM_007237 | Hs.632549 | SP140 nuclear body protein |
| AI003777 | Hs.632176 | septin 1 |
| AI421559 | Hs.106185 | ral guanine nucleotide dissociation stimulator |
| NM_020886 | Hs.503891 | ubiquitin specific protease 28 |
| AI042377 | Hs.470457 | Transcribed sequences |
| AA742584 | Hs.125914 | chromosome 8 open reading frame 5 |
| BG231773 | Hs.371680 | "CDNA FLJ46579 fis, clone THYMU3042758" |
| BE788984 | | "601481076F1 NIH_MGC_68 *Homo sapiens* cDNA clone IMAGE: 3883818 5', mRNA sequence." |
| AA135722 | Hs.597962 | Transcribed sequences |
| NM_014349 | Hs.474737 | "apolipoprotein L, 3" |
| AW268594 | Hs.374421 | chromosome 9 open reading frame 81 |
| NM_018641 | Hs.213088 | carbohydrate (chondroitin 4) sulfotransferase 12 |
| BF678830 | | hypothetical protein LOC152485 |
| NM_006117 | Hs.15250 | "peroxisomal D3,D2-enoyl-CoA isomerase" |
| AW977516 | Hs.592755 | Transcribed sequences |
| BF984830 | Hs.190284 | retinoic acid induced 1 |
| NM_005263 | Hs.73172 | growth factor independent 1 |
| AI347139 | Hs.8162 | hypothetical protein MGC39372 |
| NM_002832 | Hs.402773 | "protein tyrosine phosphatase, non-receptor type 7" |
| NM_003362 | Hs.191334 | uracil-DNA glycosylase |
| AA679705 | Hs.535464 | "eukaryotic translation initiation factor 3, subunit 8, 110 kDa" |
| AY007128 | Hs.469728 | "CDNA FLJ26765 fis, clone PRS02774" |
| AK074465 | Hs.462833 | hypothetical protein FLJ31952 |
| NM_001504 | Hs.198252 | chemokine (C-X-C motif) receptor 3 |
| NM_005715 | Hs.557541 | uronyl-2-sulfotransferase |
| AA683481 | Hs.22546 | hypothetical protein MGC20446 |
| AI829961 | Hs.36972 | CD7 antigen (p41) |
| AI609285 | Hs.503891 | "tw83h09.x1 NCI_CGAP_HN5 *Homo sapiens* cDNA clone IMAGE: 2266337 3' similar to contains Alu repetitive element; contains element MER29 repetitive element;, mRNA sequence." |
| AL582804 | Hs.403857 | lymphocyte antigen 9 |
| NM_000107 | Hs.643521 | "damage-specific DNA binding protein 2, 48 kDa" |
| AL833685 | Hs.440508 | MRNA; cDNA DKFZp667O0522 (from clone DKFZp667O0522) |
| BE568184 | | cytochrome c oxidase subunit VIa polypeptide 1 |
| BG250907 | Hs.591503 | "Clone IMAGE: 5178133, mRNA" |
| NM_018281 | Hs.476319 | hypothetical protein FLJ10948 |
| BG542955 | Hs.133916 | hypothetical protein LOC152485 |
| AK024386 | Hs.155742 | glyoxylate reductase/hydroxypyruvate reductase |
| NM_024070 | Hs.521075 | stromal antigen 3 |
| AB014719 | Hs.618112 | "amyloid beta (A4) precursor protein-binding, family A, member 2 (X11-like)" |
| D42043 | Hs.98910 | raft-linking protein |
| AY043466 | Hs.292449 | Fc receptor-like protein 3 |
| AI017564 | Hs.492716 | unknown MGC21654 product |
| NM_005317 | Hs.465511 | granzyme M (lymphocyte met-ase 1) |
| AL527430 | Hs.2006 | glutathione S-transferase M3 (brain) |
| NM_014767 | Hs.523009 | "synonym: testican-2; go_component: extracellular matrix [goid 0005578] [evidence NAS] [pmid 10386950]; go_function: calcium ion binding [goid 0005509] [evidence IDA] [pmid 10386950]; go_process: synaptogenesis [goid 0007416] [evidence NAS] [pmid 10386950]; go_process: extracellular matrix organization and biogenesis [goid 0030198] [evidence NAS] [pmid 10386950]; go_process: regulation of cell differentiation [goid 0045595] [evidence NAS] [pmid 10386950]; *Homo sapiens* sparc/osteonectin, cwcv and kazal-like domains proteoglycan (testican) 2 (SPOCK2), mRNA." |
| BC040914 | Hs.322462 | "Clone IMAGE: 5745627, mRNA" |
| AK001164 | Hs.599785 | "CDNA FLJ10302 fis, clone NT2RM2000042" |
| AK097515 | Hs.120250 | hypothetical protein FLJ40597 |

TABLE 7-continued

| GenBank ID | Unigene ID | Gene Description |
|---|---|---|
| NM_005608 | Hs.155975 | "protein tyrosine phosphatase, receptor type, C-associated protein" |
| AI457120 | Hs.331420 | phosphoribosyl pyrophosphate amidotransferase |
| AA541630 | Hs.170019 | runt-related transcription factor 3 |
| NM_024709 | Hs.519839 | hypothetical protein FLJ14146 |
| NM_013330 | Hs.642710 | "non-metastatic cells 7, protein expressed in (nucleoside-diphosphate kinase)" |
| AL520200 | Hs.420796 | hypothetical protein MGC15429 |
| NM_003752 | Hs.567374 | "eukaryotic translation initiation factor 3, subunit 8, 110 kDa" |
| BE259729 | Hs.438429 | ribosomal protein S19 |
| AW043830 | Hs.471441 | Transcribed sequences |
| R12665 | Hs.11594 | "CDNA FLJ27273 fis, clone TMS00761" |
| BC006428 | Hs.189119 | CXXC finger 5 |
| AI354636 | Hs.586401 | "qu95c03.x1 NCI_CGAP_Gas4 Homo sapiens cDNA clone IMAGE: 1979812 3', mRNA sequence." |
| AK025248 | Hs.546419 | hypothetical protein FLJ13220 |
| BE675549 | Hs.79170 | tetratricopeptide repeat domain 9 |
| NM_000579 | Hs.450802 | chemokine (C-C motif) receptor 5 |
| AB020630 | Hs.45719 | "protein phosphatase 1, regulatory (inhibitor) subunit 16B" |
| NM_002985 | Hs.514821 | chemokine (C-C motif) ligand 5 |
| NM_014392 | Hs.518595 | DNA segment on chromosome 4 (unique) 234 expressed sequence |
| AI821566 | Hs.642748 | "torsin family 2, member A" |
| AA771779 | Hs.461074 | zinc finger protein 90 homolog (mouse) |
| AI084226 | Hs.58831 | regulator of Fas-induced apoptosis |
| AF057557 | Hs.58831 | regulator of Fas-induced apoptosis |
| NM_005356 | Hs.470627 | lymphocyte-specific protein tyrosine kinase |
| BC041468 | Hs.434746 | "Hypothetical protein LOC339988 (LOC339988), mRNA" |
| BC002556 | | |
| NM_002002 | Hs.465778 | "Fc fragment of IgE, low affinity II, receptor for (CD23A)" |
| NM_018556 | Hs.590883 | signal-regulatory protein beta 2 |
| AB020630 | Hs.45719 | "protein phosphatase 1, regulatory (inhibitor) subunit 16B" |
| AF298547 | Hs.369279 | "NACHT, leucine rich repeat and PYD containing 2" |
| AW157571 | Hs.479066 | multiple coiled-coil GABABR1-binding protein |
| AA767131 | Hs.121432 | KIAA0073 protein |
| M21121 | Hs.514821 | chemokine (C-C motif) ligand 5 |
| NM_004356 | Hs.54457 | CD81 antigen (target of antiproliferative antibody 1) |
| BF432238 | Hs.585799 | "CDNA FLJ31089 fis, clone IMR321000092" |
| NM_004310 | Hs.160673 | "ras homolog gene family, member H" |
| BC000533 | Hs.567374 | "eukaryotic translation initiation factor 3, subunit 8, 110 kDa" |
| U07236 | Hs.470627 | lymphocyte-specific protein tyrosine kinase |
| AI702465 | Hs.23606 | Transcribed sequences |
| AU155091 | Hs.633678 | "Clone IMAGE: 4814008, mRNA" |
| U90339 | Hs.584739 | adenosine kinase |
| AW575245 | Hs.266331 | Fc receptor homolog expressed in B cells |
| NM_030915 | Hs.567598 | likely ortholog of mouse limb-bud and heart gene |
| AI524095 | Hs.403857 | lymphocyte antigen 9 |
| AW204712 | Hs.385493 | hypothetical protein LOC170371 |
| U49396 | Hs.408615 | "purinergic receptor P2X, ligand-gated ion channel, 5" |
| AA781795 | Hs.546467 | epithelial stromal interaction 1 (breast) |
| BF433219 | | Transcribed sequences |
| BC003574 | Hs.2484 | T-cell leukemia/lymphoma 1A |
| AB051458 | Hs.419171 | KIAA1671 protein |
| NM_004114 | Hs.6540 | fibroblast growth factor 13 |
| BF446578 | Hs.125293 | "RasGEF domain family, member 1A" |
| AA931562 | Hs.444049 | Transcribed sequence with weak similarity to protein ref: NP_060312.1 (H. sapiens) hypothetical protein FLJ20489 [Homo sapiens] |
| BF514552 | Hs.292449 | Fc receptor-like protein 3 |
| X82240 | Hs.2484 | T-cell leukemia/lymphoma 1A |
| AW296309 | Hs.405667 | "CD8 antigen, beta polypeptide 1 (p37)" |
| M85256 | Hs.554197 | "Isolate donor Z clone Z55K immunoglobulin kappa light chain variable region mRNA, partial cds" |
| AF439512 | Hs.387787 | "killer cell lectin-like receptor subfamily K, member 1" |
| NM_005442 | Hs.591663 | eomesodermin homolog (Xenopus laevis) |
| AI424825 | Hs.435052 | "ATPase, aminophospholipid transporter (APLT), Class I, type 8A, member 1" |
| NM_006159 | Hs.505326 | NEL-like 2 (chicken) |
| BI547087 | | "603190322F1 NIH_MGC_95 Homo sapiens cDNA clone IMAGE: 5261717 5', mRNA sequence." |
| BC001872 | Hs.510635 | "synonym: MU; Homo sapiens immunoglobulin heavy constant mu, mRNA (cDNA clone MGC: 1228 IMAGE: 3544448), complete cds." |
| AW006735 | Hs.85258 | "CD8 antigen, alpha polypeptide (p32)" |
| NM_007360 | Hs.387787 | "killer cell lectin-like receptor subfamily K, member 1" |
| NM_002261 | Hs.74082 | "synonyms: NKG2E, NKG2-E; isoform NKG2-E is encoded by transcript variant NKG2-E; go_component: integral to membrane [goid 0016021] [evidence IEA]; go_function: transmembrane receptor activity [goid 0004888] [evidence TAS] [pmid 9683661]; go_function: lectin [goid 0005530] [evidence IEA]; go_function: sugar binding [goid 0005529] [evidence IEA]; go_process: cellular defense response [goid 0006968] [evidence TAS] [pmid 9683661]; go_process: heterophilic cell adhesion [goid 0007157] [evidence IEA]; Homo sapiens killer cell lectin-like receptor subfamily C, member 3 (KLRC3), transcript variant NKG2-E, mRNA." |
| M13231 | Hs.534032 | T cell receptor gamma locus |
| AI753792 | Hs.502004 | related RAS viral (r-ras) oncogene homolog 2 |
| M16768 | Hs.534032 | "T-cell receptor (V-J-C) precursor; Human T-cell receptor gamma chain VJCI-CII-CIII region mRNA, complete cds." |

TABLE 7-continued

| GenBank ID | Unigene ID | Gene Description |
|---|---|---|
| NM_003175 | Hs.458346 | chemokine (C motif) ligand 2 |
| U96394 | Hs.449601 | "Clone P2-147 anti-oxidized LDL immunoglobulin light chain Fab mRNA, partial cds" |
| M27331 | Hs.534032 | T cell receptor gamma locus |
| U23772 | Hs.546295 | chemokine (C motif) ligand 1 |
| NM_004931 | Hs.405667 | "CD8 antigen, beta polypeptide 1 (p37)" |
| NM_006275 | Hs.6891 | "splicing factor, arginine/serine-rich 6" |
| BC020552 | Hs.379186 | programmed cell death 6 |
| NM_001548 | Hs.20315 | interferon-induced protein with tetratricopeptide repeats 1 |
| BC005248 | Hs.461178 | "eukaryotic translation initiation factor 1A, Y-linked" |
| NM_004660 | Hs.99120 | "DEAD (Asp-Glu-Ala-Asp) box polypeptide 3, Y-linked" |
| NM_001008 | Hs.282376 | "ribosomal protein S4, Y-linked" |

TABLE 8

| Common Name | Atheroembolic/ control | Cardioembolic/ control | Cardioembolic/ Atheroembolic |
|---|---|---|---|
| DAB2 | −1.754 | −1.21 | 1.449 |
| DAB2 | −1.751 | −1.142 | 1.531 |
| ZNF185 | −1.416 | 1.09 | 1.544 |
| ITGA2B | −2.32 | −1.081 | 2.146 |
| JAM3 | −1.694 | −1.19 | 1.424 |
| PPBP | −1.886 | −1.077 | 1.75 |
| C21orf7 | −2.293 | −1.503 | 1.527 |
| SLC25A37 | −1.326 | 1.089 | 1.444 |
| C7orf41 | −1.324 | 1.125 | 1.489 |
| SYNJ2 | −1.331 | 1.083 | 1.443 |

TABLE 9

| Common Name | Atheroembolic/ control | Cardioembolic/ control | Cardioembolic/ Atheroembolic |
|---|---|---|---|
| LAK | 1.42 | −1.375 | 1.952 |
| PVRL2 | 1.357 | −1.15 | 1.561 |
| PVRL2 | 1.432 | −1.145 | 1.64 |
| PCGF3 | 1.323 | −1.129 | 1.495 |
| PPP3R1 | 1.34 | −1.122 | 1.503 |
| LEPROT | 1.314 | −1.114 | 1.464 |
| INSR | 1.369 | −1.096 | 1.501 |
| PVRL2 | 1.859 | −1.09 | 2.028 |
| NUMB | 1.821 | −1.041 | 1.896 |
| FBN2 | 1.622 | −1.011 | 1.64 |
| BIRC1 | 1.426 | 1.007 | 1.417 |
| TSHZ3 | 1.457 | 1.013 | 1.439 |
| DF | 1.595 | 1.034 | 1.542 |
| IER3 | 1.701 | 1.197 | 1.421 |
| RRAS2 | −1.449 | 1.198 | −1.736 |
| CD8B1 | −1.259 | 1.213 | −1.526 |
| CD8B1 | −1.447 | 1.234 | −1.785 |

TABLE 10

| Gene Symbol | Fold (Cardioembolic/ Atheroembolic) | Fold (Cardioembolic/ healthy control) | Fold (Atheroembolic/ healthy control) | GenBank ID | Human UniGene ID | Gene description |
|---|---|---|---|---|---|---|
| PVRL2 | 2.028 | 1.859 | −1.09 | BE867789 | 110675 | poliovirus receptor-related 2 (herpesvirus entry mediator B) |
| NUMB | 1.896 | 1.821 | −1.041 | AW167424 | 585653 | Numb homolog (*Drosophila*) |
| IER3 | 1.421 | 1.701 | 1.197 | NM_003897 | 591785 | immediate early response 3 |
| FBN2 | 1.64 | 1.622 | −1.011 | NM_001999 | 519294 | fibrillin 2 (congenital contractural arachnodactyly) |
| CFD | 1.542 | 1.595 | 1.034 | NM_001928 | 155597 | complement factor D (adipsin) |
| TSHZ3 | 1.439 | 1.457 | 1.013 | AL136805 | 278436 | teashirt family zinc finger 3 |
| PVRL2 | 1.64 | 1.432 | −1.145 | AI520949 | 110675 | poliovirus receptor-related 2 (herpesvirus entry mediator B) |
| NAIP /// LOC728519 | 1.417 | 1.426 | 1.007 | NM_004536 | 191356 | "NLR family, apoptosis inhibitory protein /// similar to Baculoviral IAP repeat-containing protein 1 (Neuronal apoptosis inhibitory protein)" |
| ALPK1 | 1.952 | 1.42 | −1.375 | AA521086 | 99691 | alpha-kinase 1 |
| INSR | 1.501 | 1.369 | −1.096 | AI215106 | 591381 | Insulin receptor |
| PVRL2 | 1.561 | 1.357 | −1.15 | BE867789 | 110675 | poliovirus receptor-related 2 (herpesvirus entry mediator B) |
| PPP3R1 | 1.503 | 1.34 | −1.122 | NM_000945 | 280604 | "protein phosphatase 3 (formerly 2B), regulatory subunit B, 19 kDa, alpha isoform (calcineurin B, type I)" |
| PCGF3 | 1.495 | 1.323 | −1.129 | AW270105 | 144309 | Polycomb group ring finger 3 |
| LEPROT | 1.464 | 1.314 | −1.114 | NM_017526 | 23581 | leptin receptor overlapping transcript |
| C7orf41 | 1.489 | 1.125 | −1.324 | W73230 | 200100 | chromosome 7 open reading frame 41 |
| ZNF185 | 1.544 | 1.09 | −1.416 | NM_007150 | 16622 | zinc finger protein 185 (LIM domain) |
| SLC25A37 | 1.444 | 1.089 | −1.326 | BG251467 | 122514 | "solute carrier family 25, member 37" |
| SYNJ2 | 1.443 | 1.083 | −1.331 | AI971212 | 434494 | synaptojanin 2 |
| PPBP | 1.75 | −1.077 | −1.886 | R64130 | 2164 | pro-platelet basic protein (chemokine (C-X-C motif) ligand 7) |

TABLE 10-continued

| Gene Symbol | Fold (Cardioembolic/ Atheroembolic) | Fold (Cardioembolic/ healthy control) | Fold (Atheroembolic/ healthy control) | GenBank ID | Human UniGene ID | Gene description |
| --- | --- | --- | --- | --- | --- | --- |
| ITGA2B | 2.146 | −1.081 | −2.32 | NM_000419 | 411312 | "integrin, alpha 2b (platelet glycoprotein IIb of IIb/IIIa complex, antigen CD41)" |
| DAB2 | 1.531 | −1.142 | −1.751 | NM_001343 | 481980 | "disabled homolog 2, mitogen-responsive phosphoprotein (*Drosophila*)" |
| JAM3 | 1.424 | −1.19 | −1.694 | AA149644 | 150718 | junctional adhesion molecule 3 |
| DAB2 | 1.449 | −1.21 | −1.754 | BC003064 | 481980 | "disabled homolog 2, mitogen-responsive phosphoprotein (*Drosophila*)" |
| CD8B | −1.526 | −1.259 | 1.213 | AW296309 | 405667 | CD8b molecule |
| CD8B | −1.785 | −1.447 | 1.234 | NM_004931 | 405667 | CD8b molecule |
| RRAS2 | −1.736 | −1.449 | 1.198 | AI753792 | 502004 | related RAS viral (r-ras) oncogene homolog 2 |
| C21orf7 | 1.527 | −1.503 | −2.293 | NM_020152 | 222802 | chromosome 21 open reading frame 7 |

What is claimed is:

1. A method for detecting the expression of a plurality of ischemia-associated genes in a human subject having experienced or at risk for a cardioembolic stroke, the method comprising: determining a level of RNA expression of the plurality of ischemia-associated genes in a blood sample obtained from the human subject, wherein the plurality of ischemia-associated genes consists of leptin receptor overlapping transcript (LEPROT), Polycomb group ring finger 3 (PCGF3), protein phosphatase 3 regulatory subunit B, alpha (PPP3R1), poliovirus receptor-related 2 (PVRL2), insulin receptor (INSR), baculoviral IAP repeat-containing 1 (BIRC1), teashirt family zinc finger 3 (TSHZ3), complement factor D (DF), fibrillin 2 (FBN2), immediate early response 3 (IER3), numb homolog (NUMB), lymphocyte alpha-kinase (LAK), CD8 antigen, beta polypeptide 1 (CD8B1), and related RAS viral (r-ras) oncogene homolog 2 (RRAS2).

2. The method of claim 1, wherein the level of RNA expression is determined by detecting hybridization of probes that are complementary to transcripts of the plurality of ischemia-associated genes in the blood sample.

3. The method of claim 2, wherein said hybridization step is carried out on a nucleic acid array.

* * * * *